(12) United States Patent
Kamatani et al.

(10) Patent No.: US 8,963,813 B2
(45) Date of Patent: Feb. 24, 2015

(54) ORGANIC COMPOUND AND ORGANIC LIGHT EMITTING DEVICE HAVING THE SAME

(75) Inventors: Jun Kamatani, Tokyo (JP); Naoki Yamada, Inagi (JP); Tetsuya Kosuge, Yokohama (JP); Takayuki Horiuchi, Tokyo (JP); Yosuke Nishide, Kawasaki (JP); Hirokazu Miyashita, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 384 days.

(21) Appl. No.: 13/564,614

(22) Filed: Aug. 1, 2012

(65) Prior Publication Data

US 2013/0033416 A1 Feb. 7, 2013

(30) Foreign Application Priority Data

Aug. 4, 2011 (JP) .................................. 2011-171131
May 31, 2012 (JP) .................................. 2012-124503

(51) Int. Cl.
| | | |
|---|---|---|
| *G09G 3/30* | (2006.01) | |
| *C07C 25/22* | (2006.01) | |
| *H01L 51/00* | (2006.01) | |
| *C07C 49/657* | (2006.01) | |
| *C07C 49/697* | (2006.01) | |
| *C07C 13/62* | (2006.01) | |
| *C07D 215/06* | (2006.01) | |
| *C07D 333/76* | (2006.01) | |
| *C07D 209/82* | (2006.01) | |
| *C07F 7/08* | (2006.01) | |
| *C07D 213/06* | (2006.01) | |
| *H01L 51/50* | (2006.01) | |
| *H01L 27/32* | (2006.01) | |

(52) U.S. Cl.
CPC ............ *C07C 25/22* (2013.01); *H01L 51/0056* (2013.01); *C07C 49/657* (2013.01); *C07C 49/697* (2013.01); *C07C 13/62* (2013.01); *C07D 215/06* (2013.01); *C07D 333/76* (2013.01); *C07D 209/82* (2013.01); *C07F 7/0809* (2013.01); *C07D 213/06* (2013.01); *G03G 2215/0407* (2013.01); *H01L 51/5012* (2013.01); *H01L 27/3244* (2013.01); *C07C 2103/54* (2013.01)
USPC ........................................................... 345/76

(58) Field of Classification Search
None
See application file for complete search history.

(56) References Cited

FOREIGN PATENT DOCUMENTS

| JP | 2001-267076 A | | 9/2001 | |
|---|---|---|---|---|
| JP | 2001-319782 A | | 11/2001 | |
| JP | 2002-25777 | * | 1/2002 | ............. C07C 13/62 |
| JP | 3792097 B2 | | 6/2006 | |
| JP | 3998398 B2 | | 10/2007 | |
| JP | 2009-033069 A | | 2/2009 | |

* cited by examiner

*Primary Examiner* — Tony N Ngo
(74) *Attorney, Agent, or Firm* — Canon U.S.A., Inc. IP Division

(57) ABSTRACT

An organic compound contains indacenodiperylene as the basic skeleton.

13 Claims, 2 Drawing Sheets

ORGANIC COMPOUND AND ORGANIC LIGHT EMITTING DEVICE HAVING THE SAME

BACKGROUND OF THE INVENTION

1. Field of the Invention

The present invention relates to an organic compound and an organic light emitting device having the same.

2. Description of the Related Art

An organic light emitting device (referred to as an organic electroluminescence device or an organic EL device) is an electronic device having a pair of electrodes and an organic compound layer disposed between these electrodes. By injecting electrons and holes from the pair of electrodes, excitons of a luminescent organic compound in the organic compound layer are generated. When the excitons return to the ground state, the organic light emitting device emits light.

Recent progress of the organic light emitting device is remarkable, and, for example, a low drive voltage, various light emission wavelengths, high-speed responsiveness, and a reduction in thickness and weight of a light emitting device can be achieved.

The creation of the luminescent organic compound has been actively performed so far. This is because, in providing a high-performance organic light emitting device, the creation of compounds having excellent light emitting properties is important.

As the compounds which have been created so far, the following compound 1-A disclosed in Japanese Patent Laid-Open Nos. 2001-319782 and 2009-033069 is mentioned, for example.

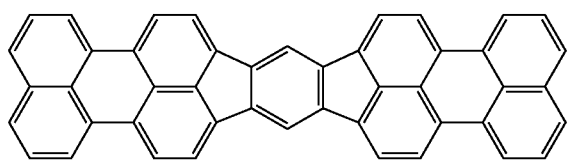
1-A

The compound 1-A has s-indaceno[1,2,3-cd:5,6,7-c'd']diperylene as the basic skeleton. Herein, according to the analysis of the present inventors, the light emitted from the s-indaceno[1,2,3-cd:5,6,7-c'd']diperylene skeleton itself is orange light as described later.

Japanese Patent Laid-Open No. 2001-267076 has proposed the following compound 1-B.

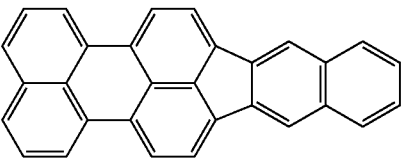
1-B

The compound 1-B has benzo[5,6]indeno[1,2,3-cd]perylene as the basic skeleton. Herein, according to the analysis of the present inventors, the light emitted from the benzo[5,6]indeno[1,2,3-cd]perylene skeleton itself is yellow light as described later.

However, the basic skeleton of each of the compounds described in Japanese Patent Laid-Open Nos. 2001-319782, 2009-033069, and 2001-267076 can emit only orange or bluish green light as described above, and light emission in the pure red region is not obtained.

SUMMARY OF THE INVENTION

The present invention has been made in order to solve the above-described problems. Aspects of the invention provide an organic compound which emits light in the pure red region. Aspects of the invention also provide an organic light emitting device having high luminous efficiency.

The organic compound according to aspects of the invention is represented by the following Formula (1).

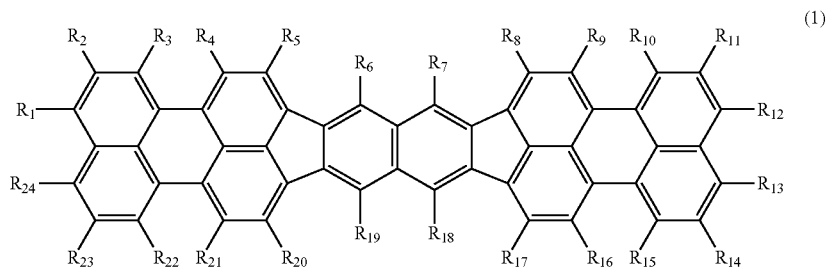
(1)

In Formula (1), $R_1$ to $R_{24}$ each are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted arylocxy group, a silyl group, and a cyano group.

Further features of the present invention will become apparent from the following description of exemplary embodiments with reference to the attached drawings.

DESCRIPTION OF THE EMBODIMENTS

Figure 1:
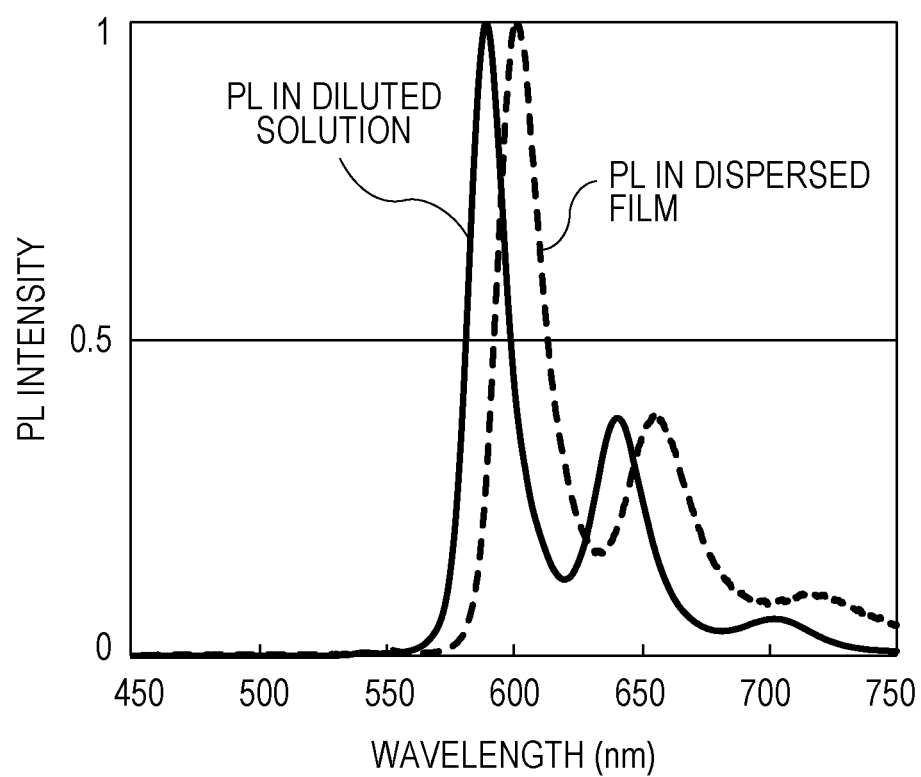
FIG. 1 illustrates the emission spectrum of each of the photoluminescence in a diluted solution and the photoluminescence in a film of a compound A7.

First, an organic compound according to aspects of the invention is described. A novel organic compound according to aspects of the invention is an organic compound having the basic skeleton represented by the following Formula (1).

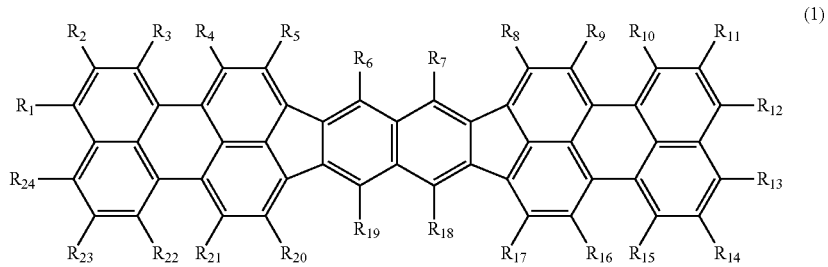

In Formula (1), $R_1$ to $R_{24}$ shown in the basic skeleton each are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted arylocxy group, a silyl group, and a cyano group.

In this embodiment, $R_1$ to $R_{24}$ in Formula (1) each are suitably independently selected from a hydrogen atom, a substituted or unsubstituted alkyl group, and a substituted or unsubstituted aryl group.

Mentioned as the halogen atom represented by $R_1$ to $R_{24}$ are fluorine, chlorine, bromine, iodine, and the like but the halogen atom is not limited thereto.

Mentioned as the alkyl group represented by $R_1$ to $R_{24}$ are a methyl group, an ethyl group, a normal propyl group, an isopropyl group, a normal butyl group, a tertiary butyl group, a secondary butyl group, an octyl group, a cyclohexyl group, a 1-adamantyl group, a 2-adamantyl group, and the like but the alkyl group is not limited thereto.

Mentioned as the alkoxy group represented by $R_1$ to $R_{24}$ are a methoxy group, an ethoxy group, a propoxy group, a 2-ethyl-octyloxy group, a benzyloxy group, and the like but the alyoxy group is not limited thereto.

Mentioned as the amino group represented by $R_1$ to $R_{24}$ are an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-didiphenylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary butylphenyl)amino group, an N-phenyl-N-(4-trifluoromethylphenyl)amino group, and an N-piperidyl group, and the like but the amino group is not limited thereto.

Mentioned as the aryl group represented by $R_1$ to $R_{24}$ are a phenyl group, a naphthyl group, an indenyl group, a biphenyl group, a terphenyl group, a fluorenyl group, and the like but the aryl group is not limited thereto.

Mentioned as the heterocyclic group represented by $R_1$ to $R_{24}$ are a pyridyl group, an oxazolyl group, an oxadiazolyl group, a thiazolyl group, a thiadiazolyl group, a carbazolyl group, an acridinyl group, and a phenanthrolyl group, and the like but the heterocyclic group is not limited thereto.

Mentioned as the aryloxy group represented by $R_1$ to $R_{24}$ are a phenoxy group, a thienyloxy group, and the like but the aryloxy group is not limited thereto.

Mentioned as the silyl group represented by $R_1$ to $R_{24}$ are a triphenylsilyl group and the like but the silyl group is not limited thereto.

Mentioned as a substituent which the alkyl group, the alkoxy group, the amino group, the aryl group, the heterocyclic group, and the aryloxy group mentioned above may have are alkyl groups, such as a methyl group, an ethyl group, a normal propyl group, an isopropyl group, a normal butyl group, and a tertiary butyl group, aralkyl groups, such as a benzyl group, aryl groups, such as a phenyl group and a biphenyl group, heterocyclic groups, such as a pyridyl group and a pyrrolyl group, amino groups, such as a dimethylamino group, a diethylamino group, a dibenzylamino group, a diphenylamino group, and a ditolylamino group, alkoxy groups, such as a methoxy group, an ethoxy group, and a propoxy group, aryloxy groups, such as a phenoxy group, halogen atoms, such as fluorine, chlorine, bromine, and iodine, a cyano group, and the like but the substituent is not limited thereto.

In this embodiment, $R_1$ to $R_{24}$ in Formula (1) each are suitably independently selected from a hydrogen atom or a substituted or unsubstituted aryl group.

When a substituent is introduced into the basic skeleton in the organic compound according to this embodiment, a compound can be obtained in which the concentration quenching is suppressed, the sublimation properties are improved in sublimation, and the solvent solubility is improved when used in application.

It is suitable from the viewpoint of the suppression of the concentration quenching that at least any one of $R_1$ to $R_{24}$ in Formula (1) is substituted with an alkyl group.

Next, a method for synthesizing the organic compound according to this embodiment is described. The organic compound according to this embodiment is synthesized according to the reaction schemes shown below, for example.

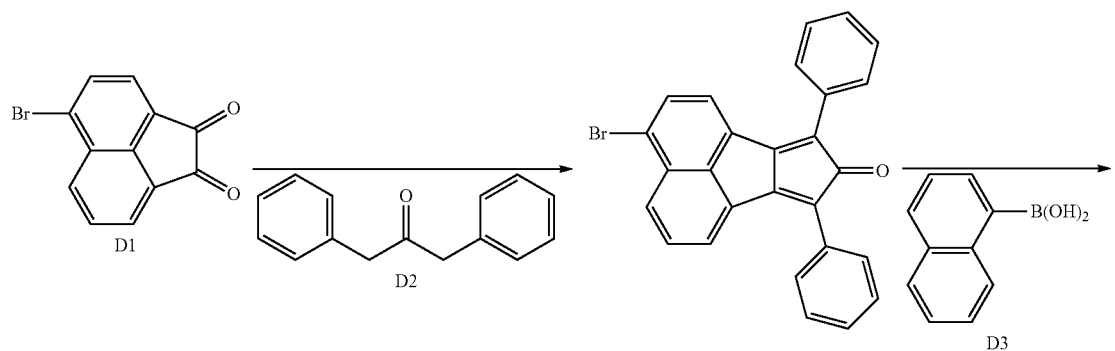
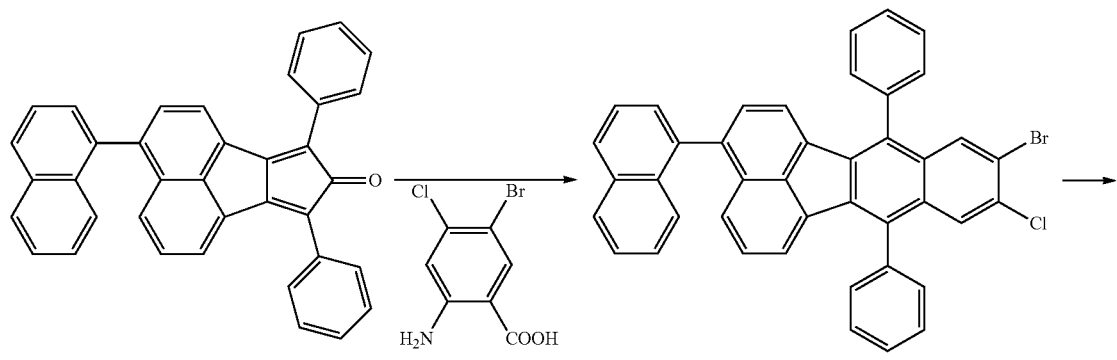
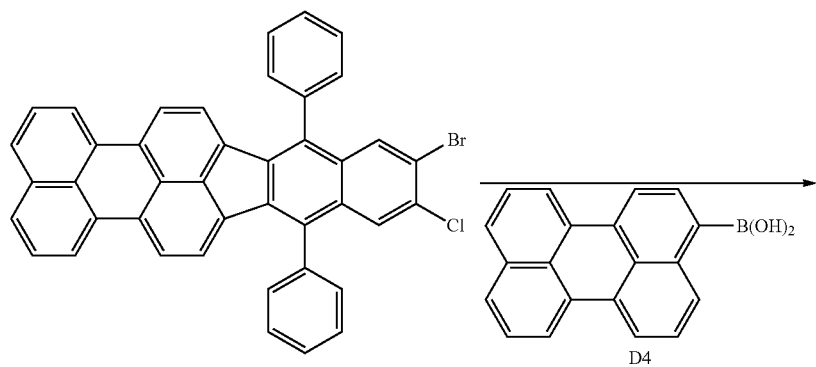
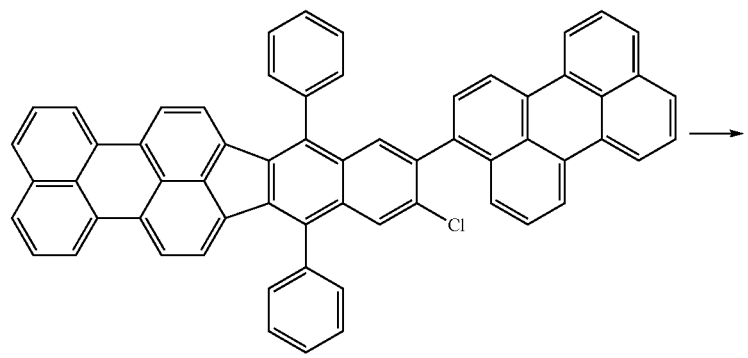

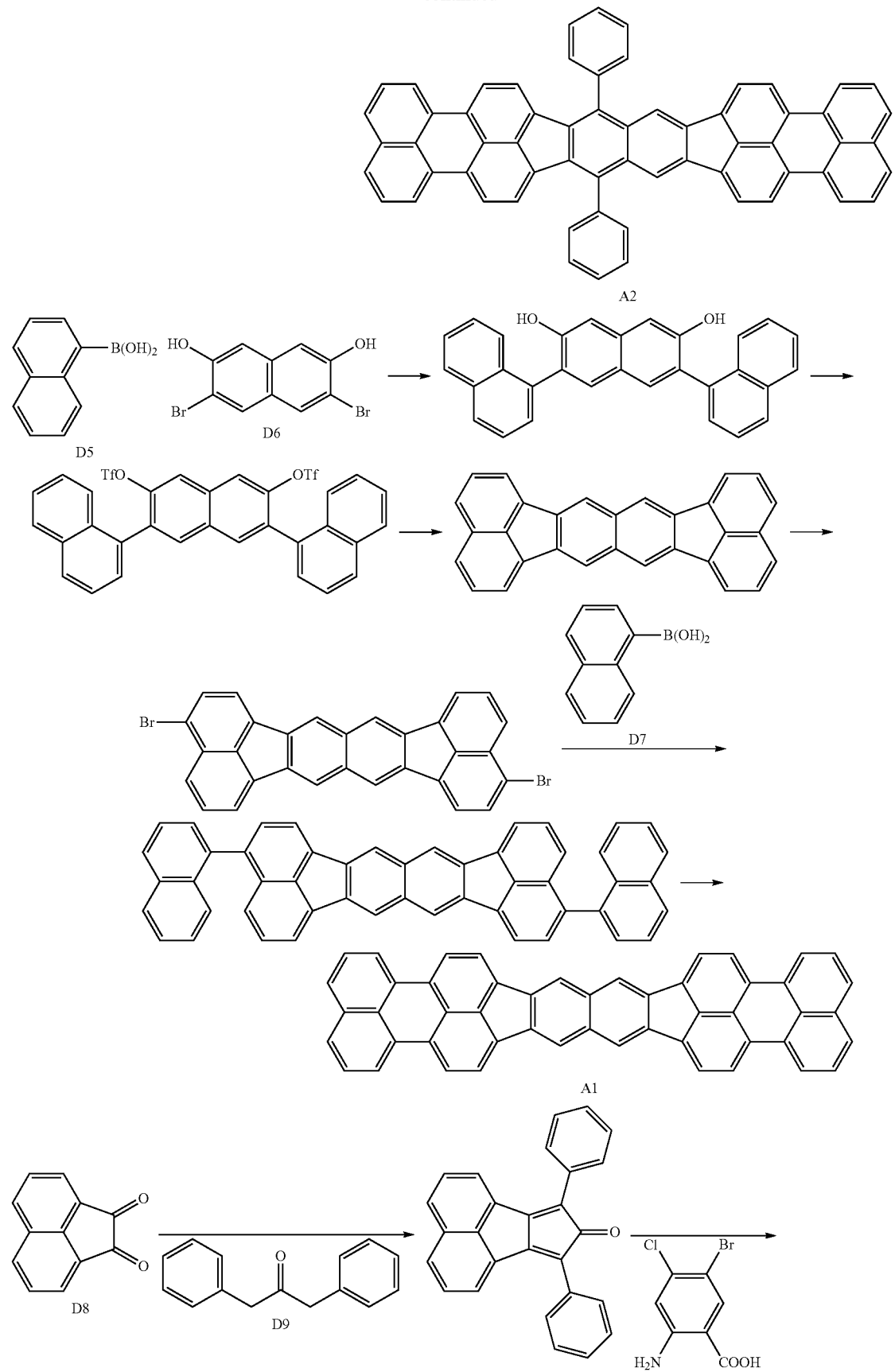

-continued
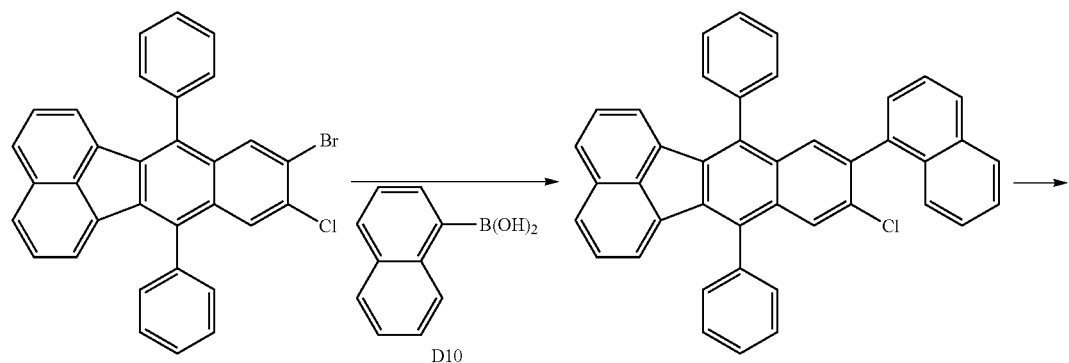
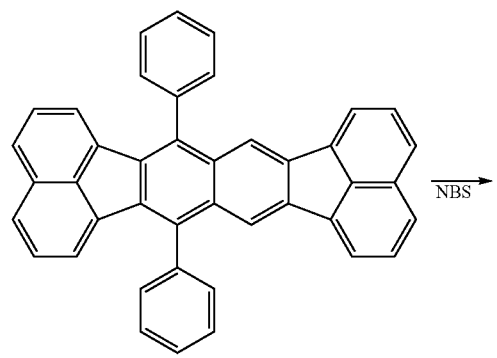
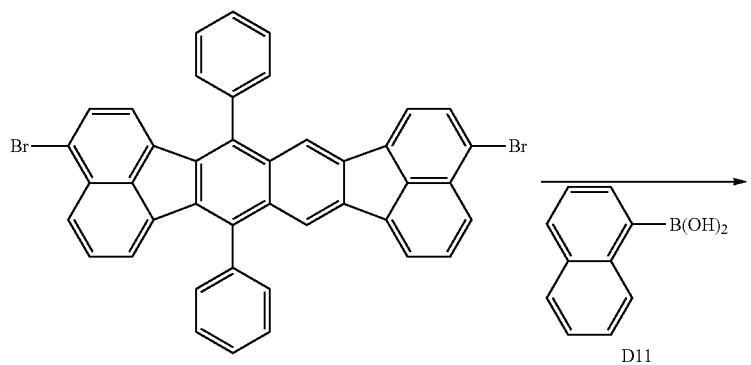
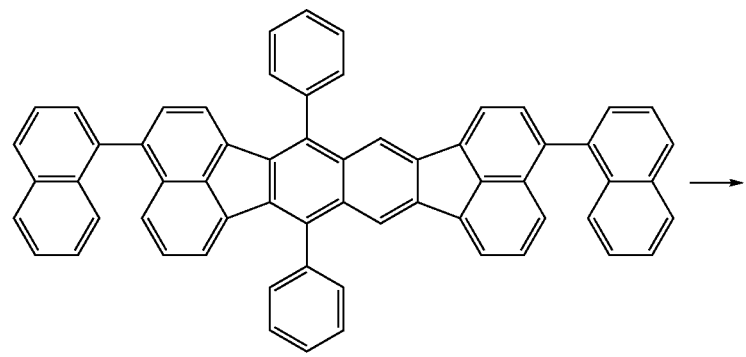

-continued

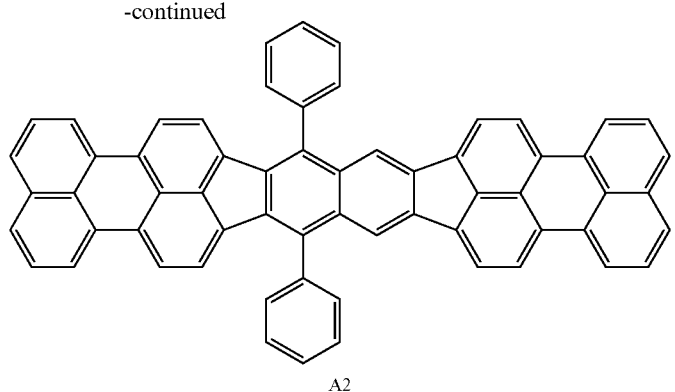

A2

As represented by the synthetic schemes, the organic compound according to this embodiment is synthesized using the following compounds represented by (a) to (f) as the raw materials.

(a) Diketone derivative (D1)
(b) Dibenzylketone derivative (D2)
(c) Naphthalene derivative (D3)
(d) Binaphthyl derivative (D4)
(e) Naphthalene derivative (D5)
(f) 3,6-dibromonaphthalene derivative (D6)
(g) Naphthalene derivative (D7)
(h) Diketone derivative (D8)
(i) Dibenzylketone derivative (D9)
(j) Naphthalene derivative (D10)
(k) Naphthalene derivative (D11)

Herein, by introducing a substituent into the compounds represented by (a) to (k) above as appropriate, the hydrogen atom is substituted with a predetermined substituent in any one of $R_1$ to $R_{24}$ in Formula (1). Mentioned as the substituent to be introduced herein are an alkyl group, a halogen atom, a phenyl group, a methoxy group, a cyano group, and the like.

By individually changing D1 to D11 in the synthetic schemes above, various organic compounds can be synthesized.

Next, the characteristics of the basic skeleton of the organic compound according to this embodiment are described.

When the present inventors devise the organic compound represented by Formula (1), the present inventors have focused on the basic skeleton itself. Specifically, the present inventors have attempted to provide one in which the light emission wavelength of the molecules of only the basic skeleton is in a desired light emission wavelength region.

In this embodiment, a desired light emission wavelength region is the pure red region. Specifically, the maximum light emission wavelength in a diluted solution is 590 nm or more and 620 nm or lower.

Compounds are different in the light emission wavelength between in a diluted solution and in a dispersed film, i.e., a solid film. An organic light emitting device has a dispersed film among them. In the dispersed film, the maximum light emission wavelength (the maximum peak among the peaks of the emission spectrum) increases by about 10 to 15 nm, for example. As an example, FIG. 1 shows the emission spectrum of each of the photoluminescence (PL) in a diluted solution and the photoluminescence in a film (dispersed film) of the compound A7. The concentration of the compound A7 in the diluted solution is $1 \times 10^{-5}$ mol/L. The compound A7 in the dispersed film is dispersed in a proportion of 0.1% in polyvinyl carbazole which is the dispersed film.

The compound used herein refers to a compound in which the basic skeleton is formed with only carbon.

Therefore, when the wavelength is 590 nm or more in the diluted solution, the wavelength is 600 nm or more in the dispersed film or in a light emitting device, so that pure red light emission with high color purity can be obtained.

Next, the characteristics of the basic skeleton of the organic compound according to aspects of the invention are described in comparison with comparative compounds having structures similar to that of the organic compound according to aspects of the invention. Specifically, the compounds represented by the following formulae (2), (3), and (4) are mentioned as the comparative compounds.

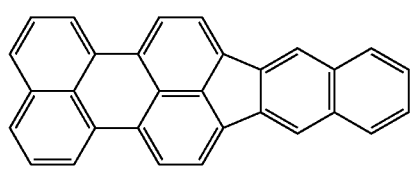

(2)

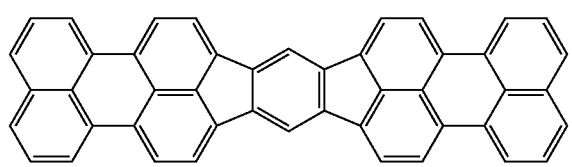

(3)

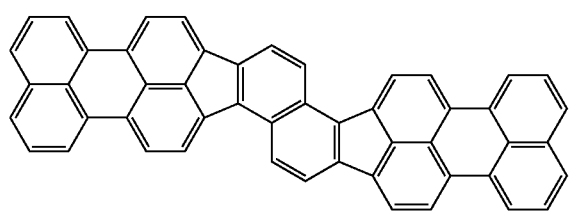

(4)

Herein, one of the organic compounds according to aspects of the invention is a compound which has the basic skeleton represented by Formula (1) and is represented by the following Formula (5) in which $R_1$ to $R_{24}$ are all hydrogen atoms.

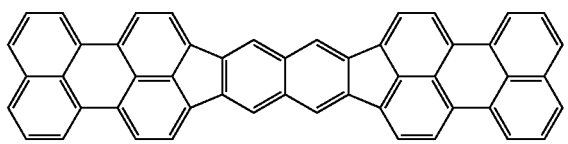

(5)

Herein, the preset inventors compared the light emission wavelength and the quantum yield in a toluene diluted solution and the chromaticity in a film dispersed in a proportion of 0.1% in polyvinyl carbazole between the organic compound represented by Formula (5) and the organic compounds of Formulae (2), (3), and (4). The results are shown in Table 1.

the conditions, with respect to the shape of the emission spectrum in a dispersed film, the intensity at 570 nm or lower needs to be 0.1 or lower. To that end, the maximum light emission wavelength may be longer. However, when the wavelength is excessively long, not a pure red color but a dark red color is produced. Therefore, in order to emit a pure red color, the maximum light emission wavelength in a dispersed film is suitably 600 nm or more and 630 nm or lower and in order for the intensity at 570 nm or lower to be 0.1 or lower, the half width is suitably 30 nm or lower.

The value of the compound 3 is quite smaller than the value of the red color of the NTSC standard or the red color of the sRGB standard. Therefore, the compound 3 is not suitable as a light emitting material of a pure red color demanded in this embodiment.

TABLE 1

| Chemical compound No. | Structural formula | Maximum light emission wavelength (nm) | Quantum yield | Chromaticity (X, Y) | Chromaticity of dispersed film (X, Y) |
|---|---|---|---|---|---|
| 2 | | 532 | 0.79 | (0.38, 0.60) | (0.45, 0.54) |
| 3 | | 585 | 0.78 | (0.59, 0.40) | (0.61, 0.38) |
| 4 | | 596 | <0.1 | (0.63, 0.37) | (0.65, 0.37) |
| 5 | | 593 | 0.88 | (0.63, 0.38) | (0.65, 0.36) |

The color of the light emitted from the compound 2 of Table 1 is yellow and is not red.

The color of the light emitted from the compound 3 of Table 1 is orange and is not red. The light emitted from the organic compound has a large number of orange light emission components which reduce the purity of a red color.

As the index of the color of emitted light, CIE colorimetric (X, Y) coordinates are mentioned. In order to produce a pure red color to a red color with NTSC chromaticity coordinates (0.68, 0.32) or a red color with sRGB chromaticity coordinates (0.64, 0.33), the X coordinate needs to be larger than the values. When the X coordinate is smaller than the values, yellow color is mixed with the color of emitted light, so that the color is not suitable as a pure red color. In order to satisfy The color of the light emitted from the compound 4 of Table 1 is a pure red color. However, the quantum yield thereof is 0.1 or lower, which is 10 or more times lower than that of the other compounds (Compound 1, Compound 2, and Compound 4). This means that the energy produced when holes and electrons are re-joined cannot be efficiently converted to light.

The color of the light emitted from the compound 5 which is the compound of this embodiment of Table 1 is suitable for a pure red color of the standard of a display as compared with the other materials mentioned above. Moreover, FIG. 1 shows that the half width of the waveshape of the maximum light emission wavelength of the organic compound having this basic skeleton is as narrow as 15 to 20 nm. The band gap of the basic skeleton is as narrow as 2.0 eV or more and 2.1 eV or lower. Moreover, the compound is a material having a quantum yield as high as 0.7 or more. Therefore, it can be said that the basic skeleton is an excellent skeleton as a red light emitting material which can contribute to a reduction in the power consumption of an organic light emitting device.

Moreover, in the organic compound according to this embodiment, the crystallinity of the molecules themselves can be suppressed to some extent by further introducing a substituent. The suppression of crystallinity leads to control of the concentration quenching between molecules or improvement of sublimation properties. Specifically, in the case of an alkyl group, a methyl group, an ethyl group, a propyl group, a butyl group, a hexyl group, an octyl group, and the like are suitable, and particularly an isopropyl group or a tertiary butyl group which is three dimensionally large is suitable. Also in the case of an aryl group, an aryl group, such as a phenyl group having substituents, such as a methyl group, a xylyl group, a mesityl group, an isopropyl group, and a tertiary butylphenyl group, is suitable. Moreover, fluorine is also suitable in this respect. Moreover, when using the same for a method including compounding the same in liquid to dispose the same at a predetermined position (application), and then removing a solvent, the film properties are improved, and therefore it is suitable to introduce the substituent.

Since the organic compound according to this embodiment has two 5-membered ring structures in the skeleton, the LUMO energy level is low as described above. This means that the oxidation potential of the compound is low. Therefore, the organic compound according to this embodiment is stable to oxidization.

The basic skeleton of the organic compound according to this embodiment is constituted by only carbon and does not have a hetero atom, such as a nitrogen atom. This also contributes to the fact that the oxidation potential of the compound itself is low and is one of the reasons why the organic compound according to this embodiment is stable to oxidization.

Specific examples of the organic compound according to aspects of the invention are shown below.

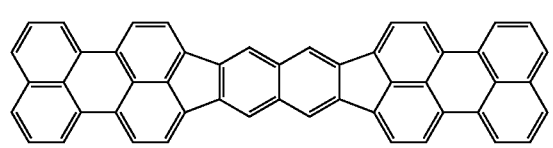

A1

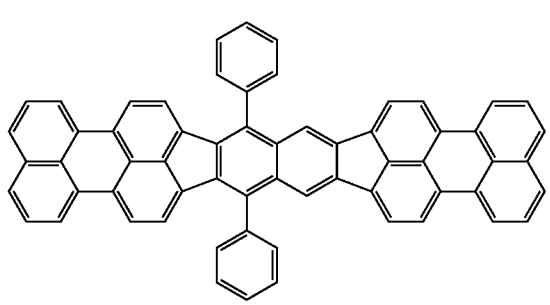

A2

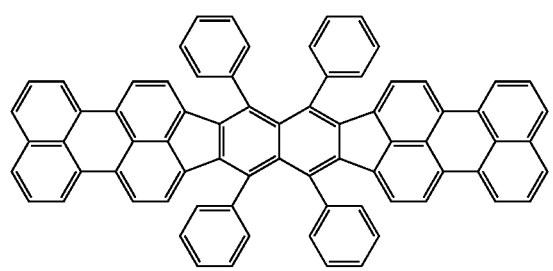

A3

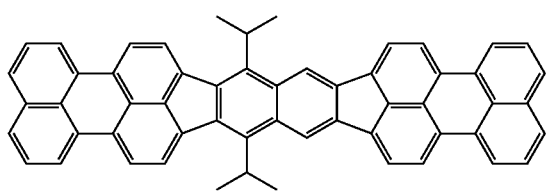

A4

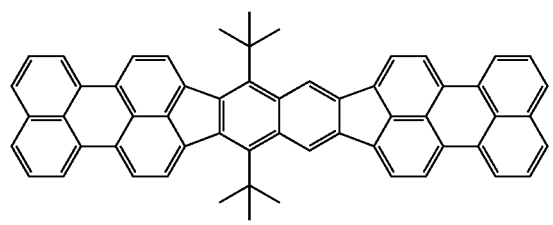

A5

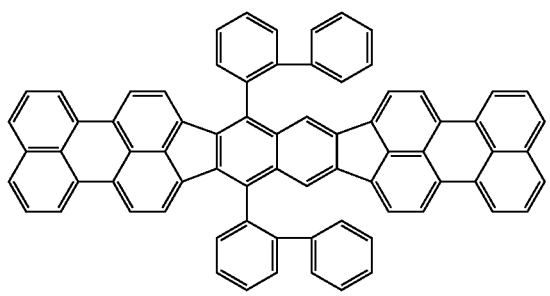

A6

-continued
A7
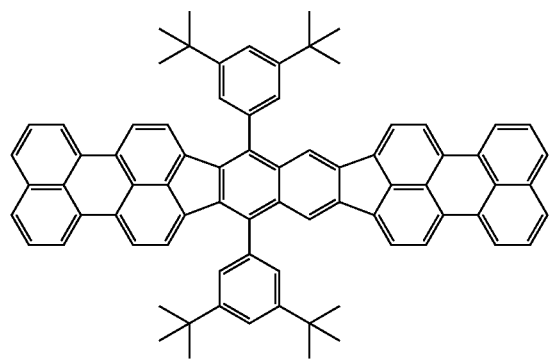
A8
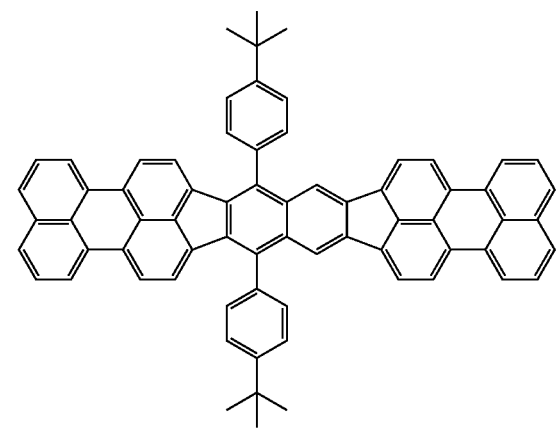
A9
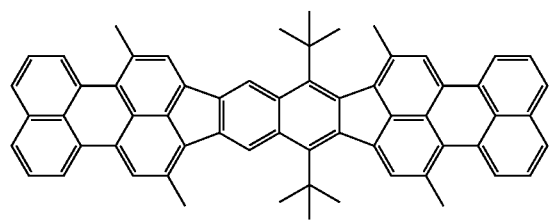
A10
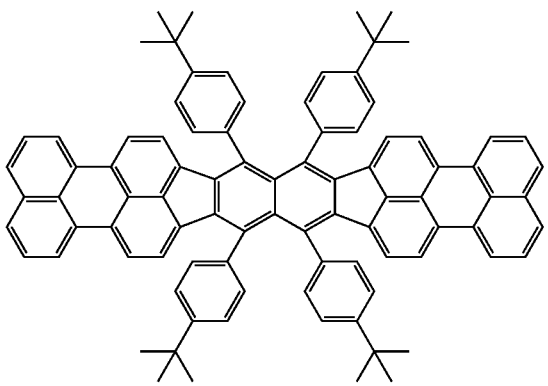
A11
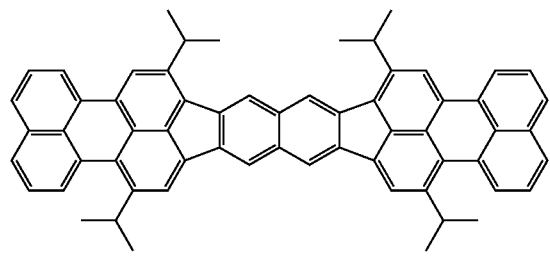
A12
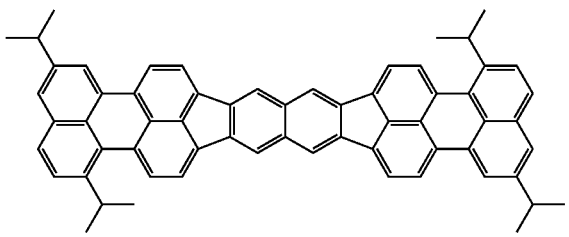
A13
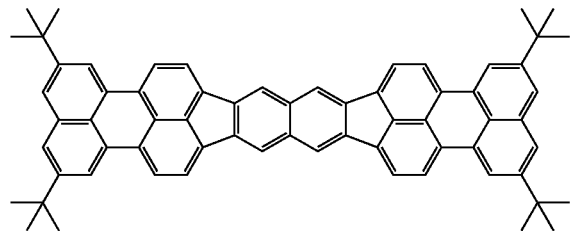
A14
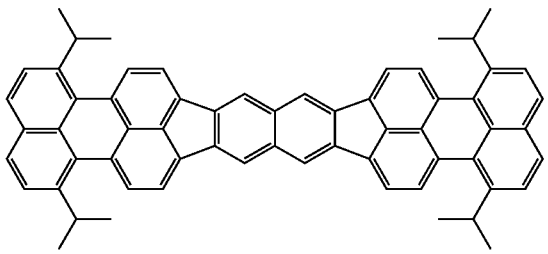

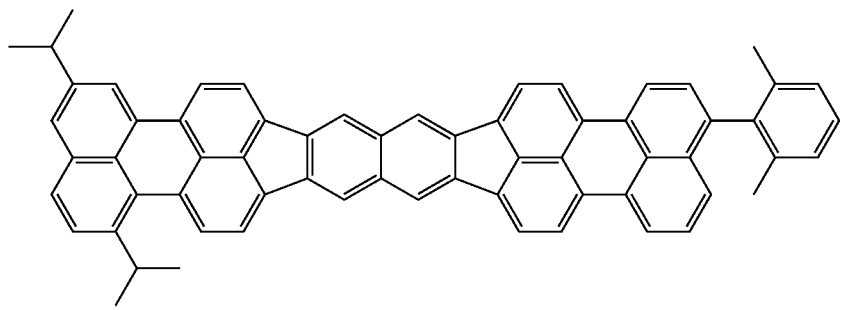
A15
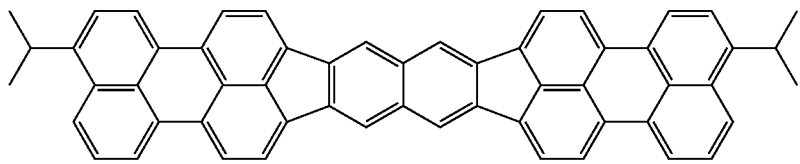
A16
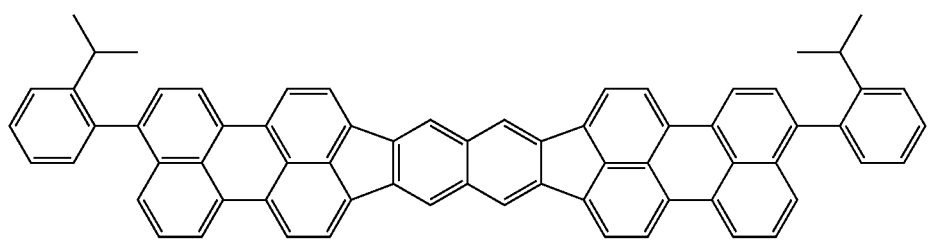
A17
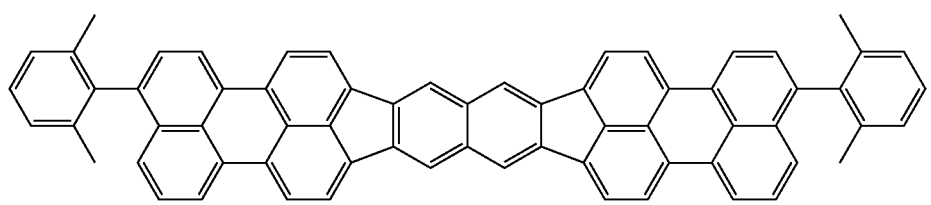
A18
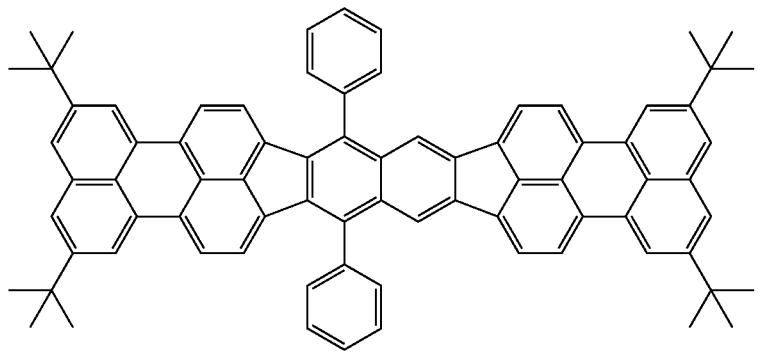
A19
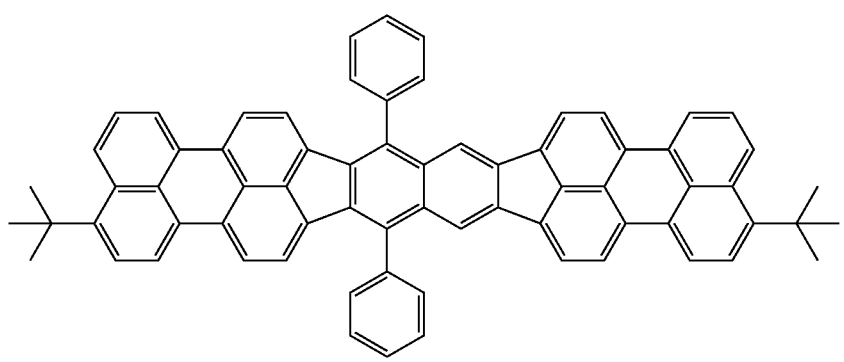
A20

-continued
A21
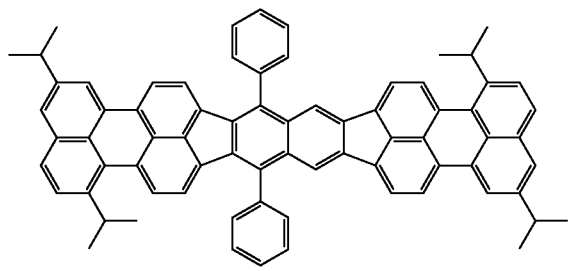
A22
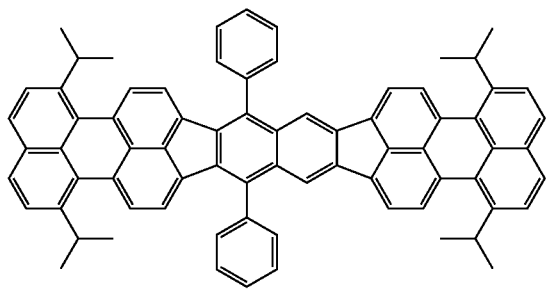
A23
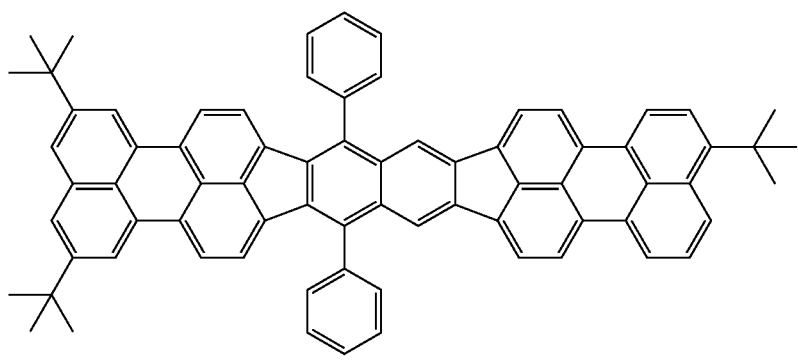
A24
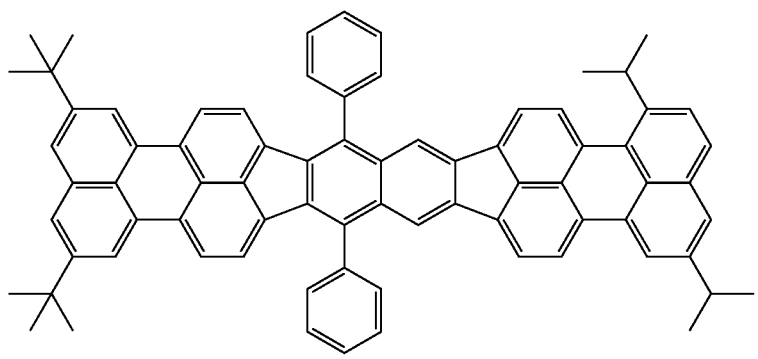
A25
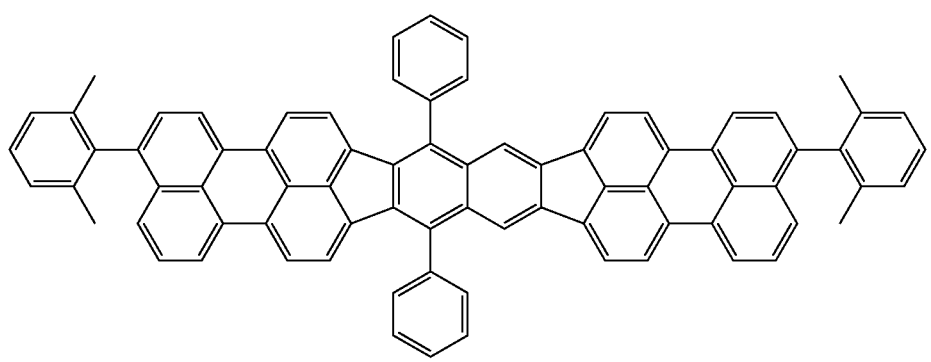

-continued
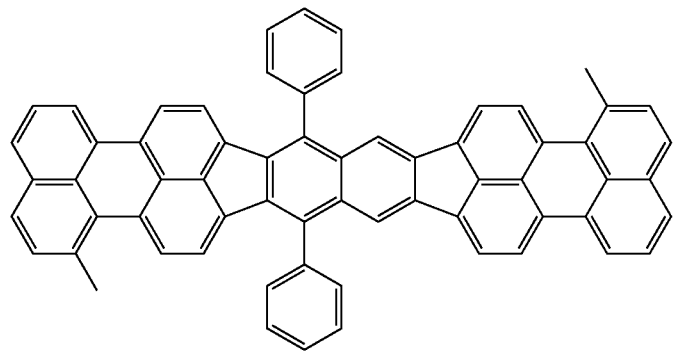
A26
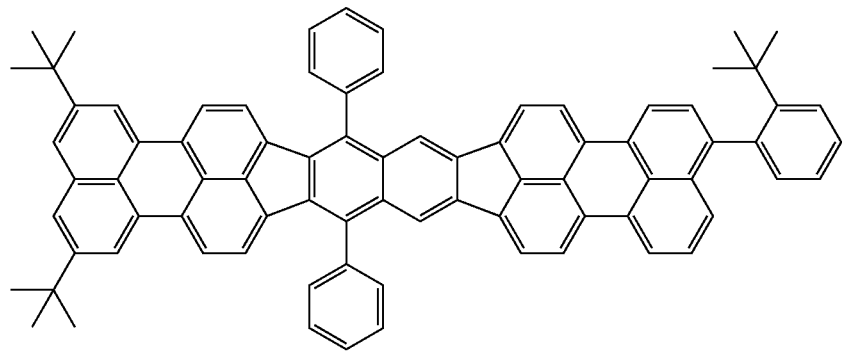
A27
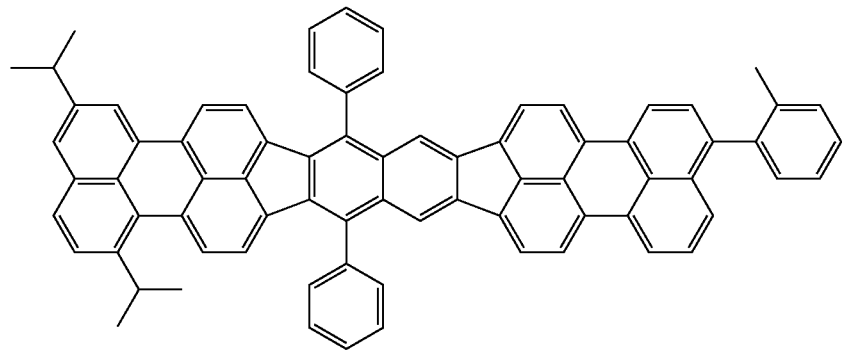
A28
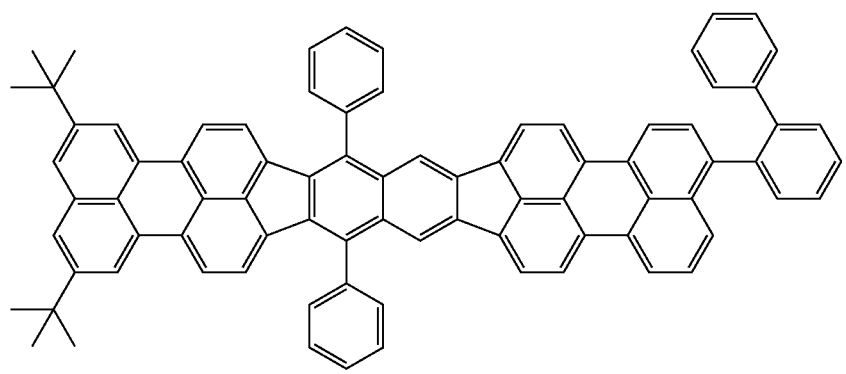
A29

A30
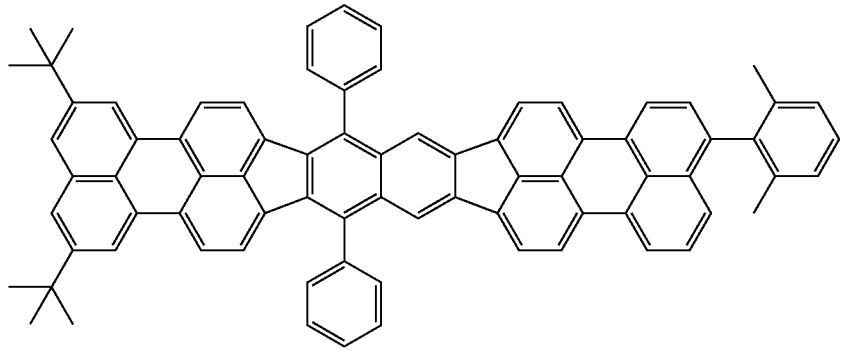
A31
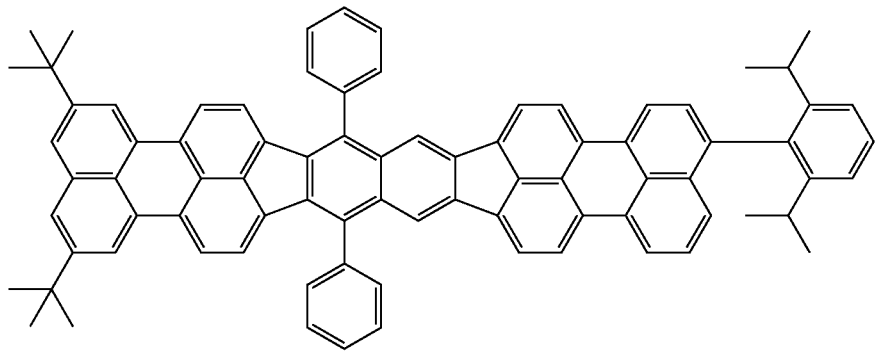
A32
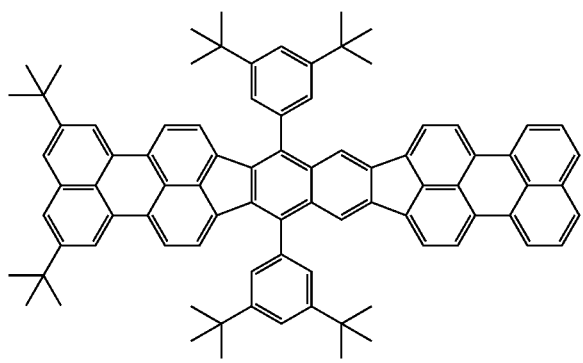
A33
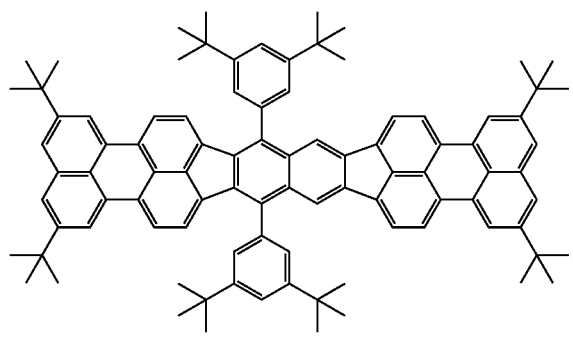
A34
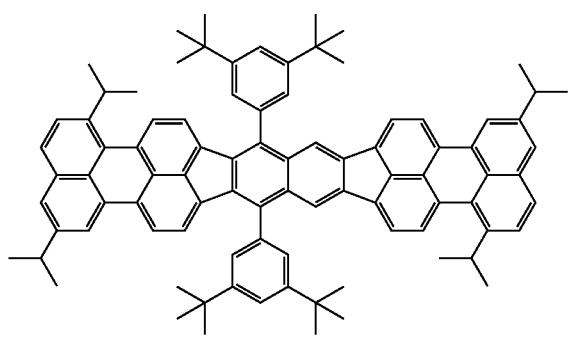
A35
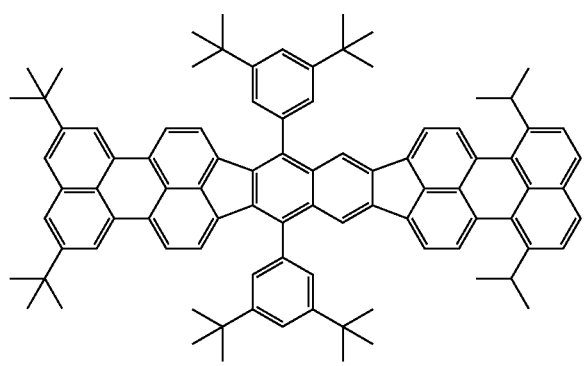

-continued
A36
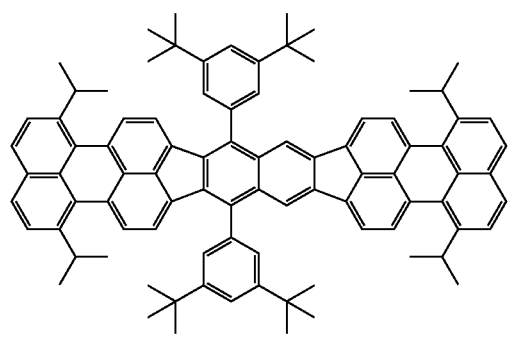
A37
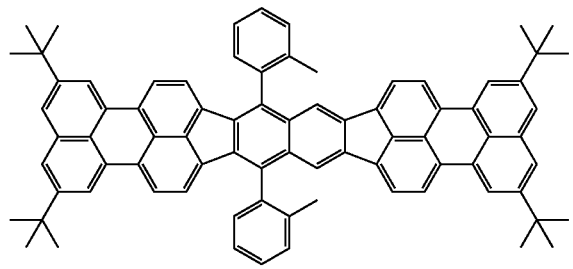
A38
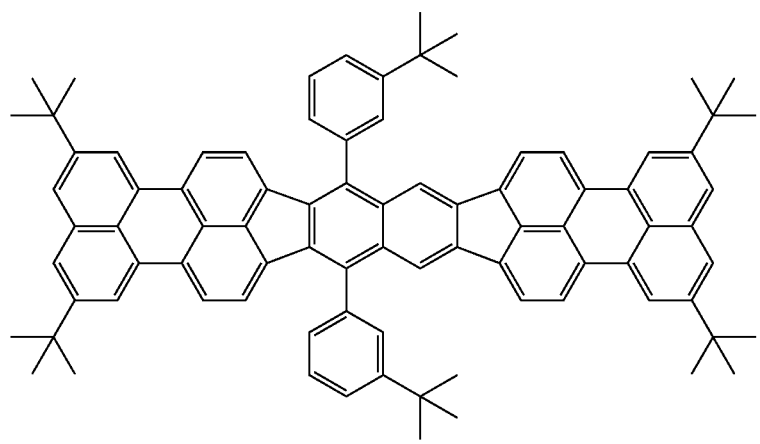
A39
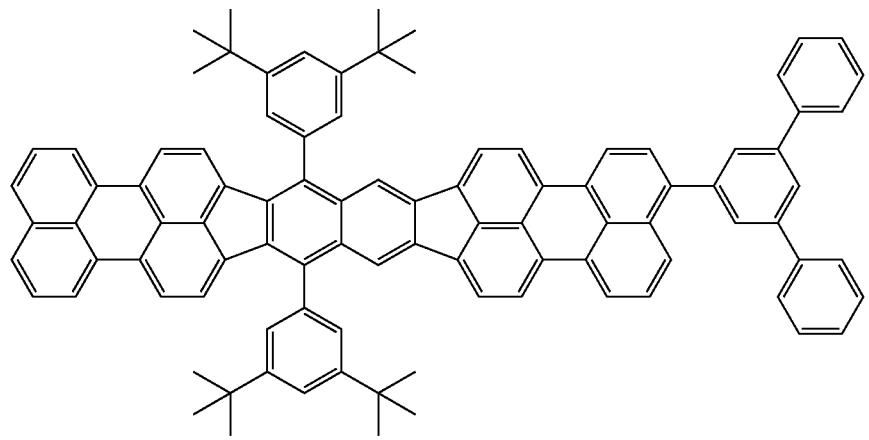
A40
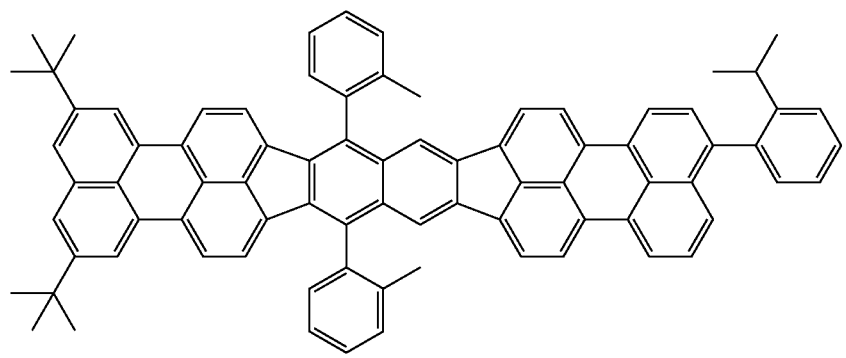

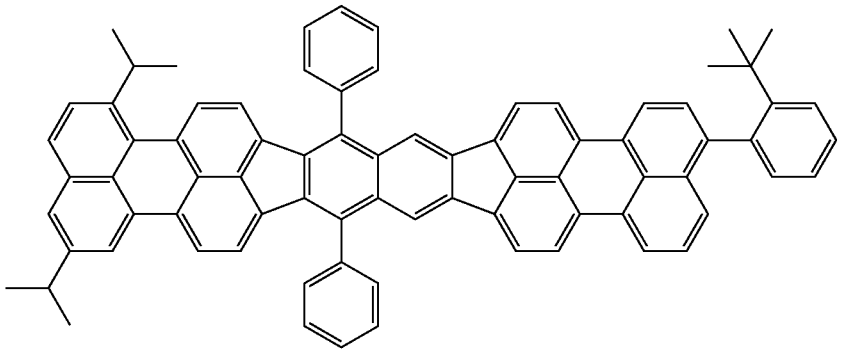
A41
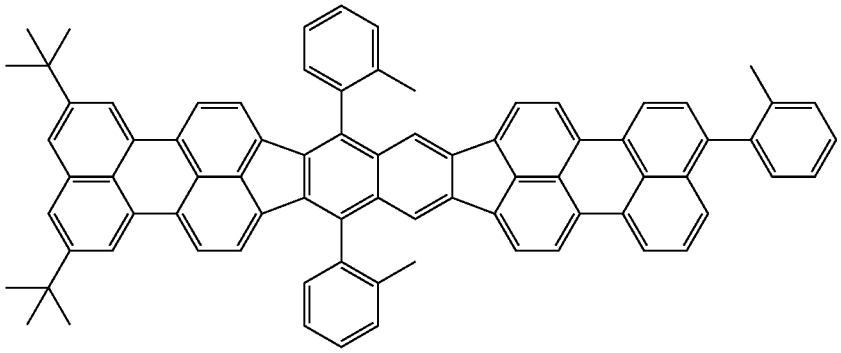
A42
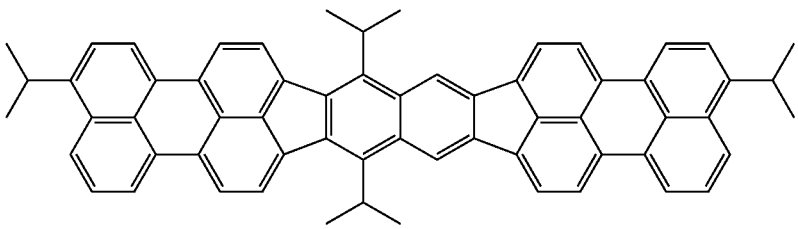
A43
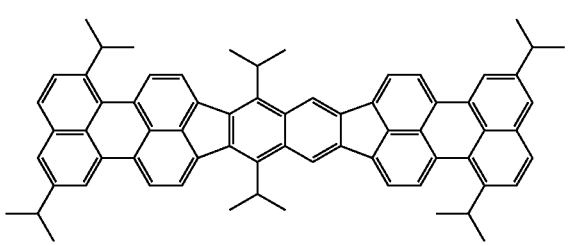
A44
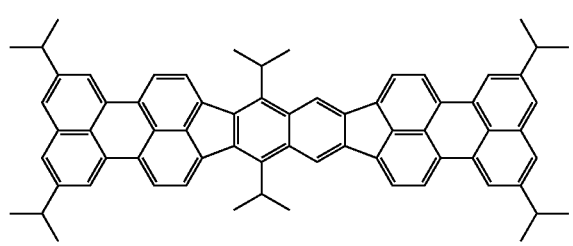
A45
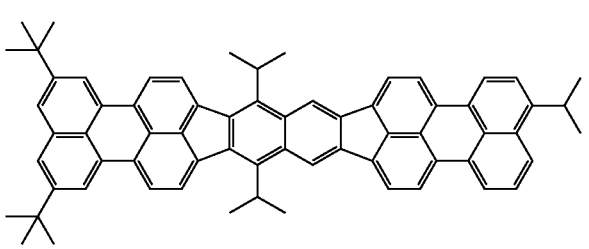
A46
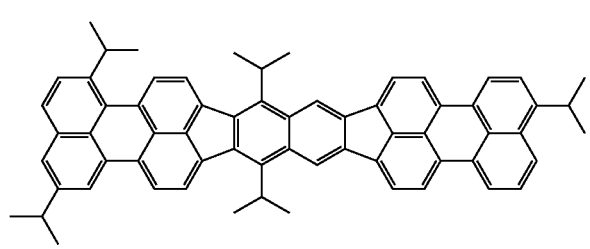
A47

-continued
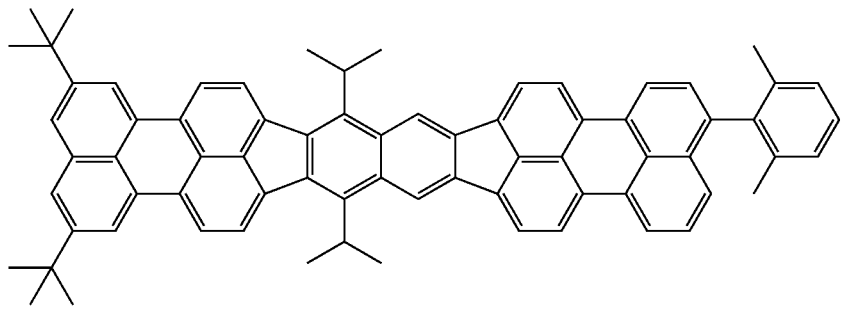
A48
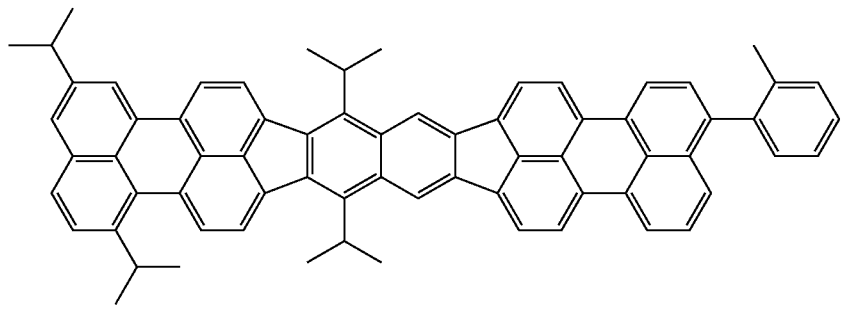
A49
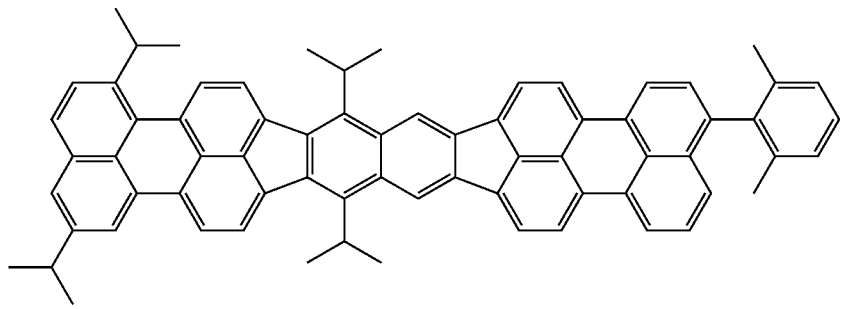
A50
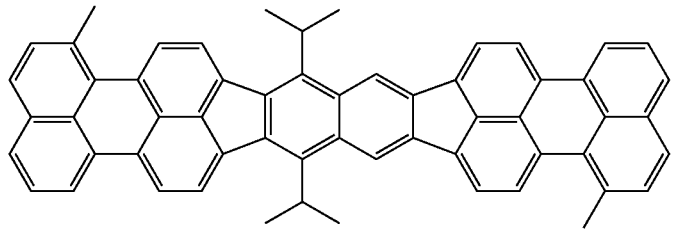
A51
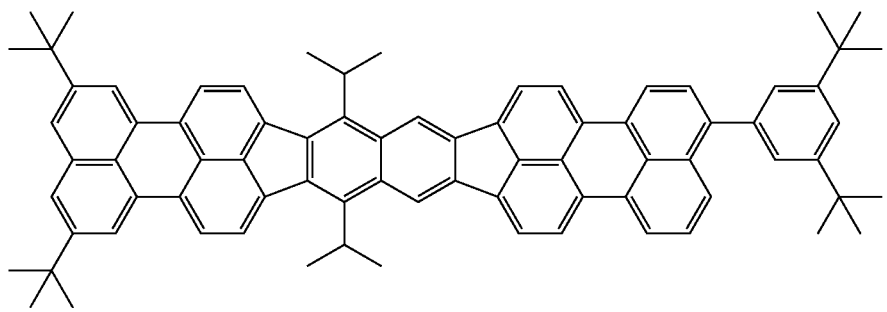
A52

-continued
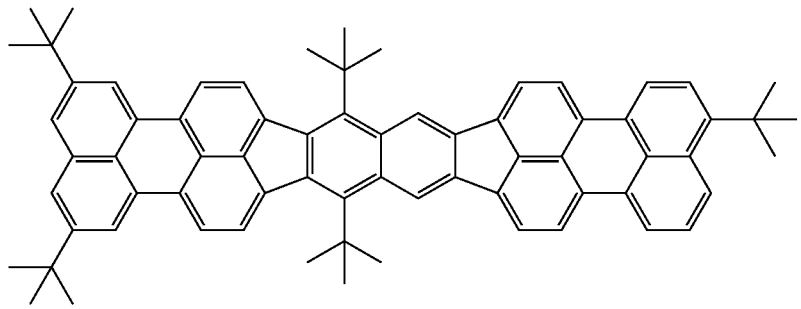
A53
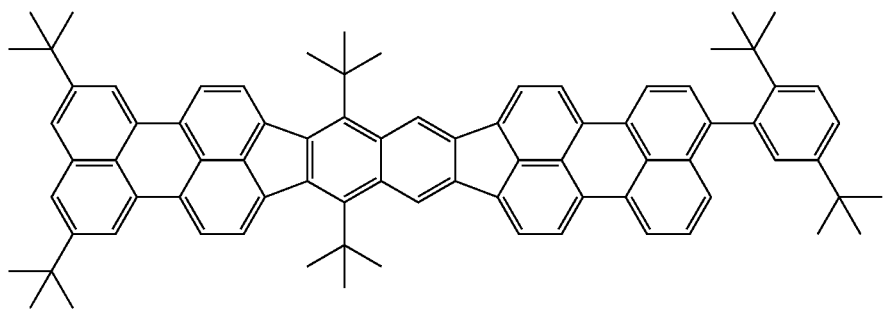
A54
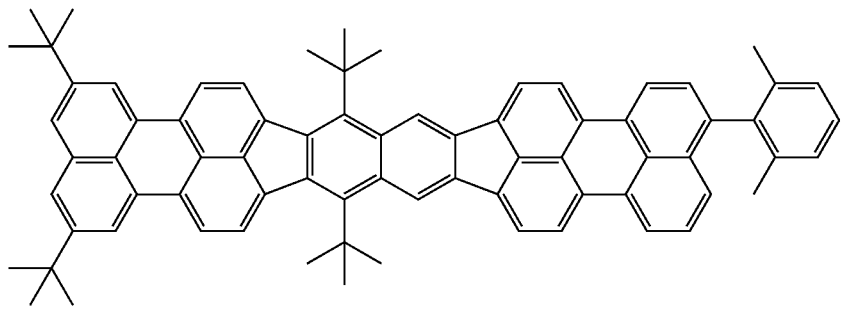
A55
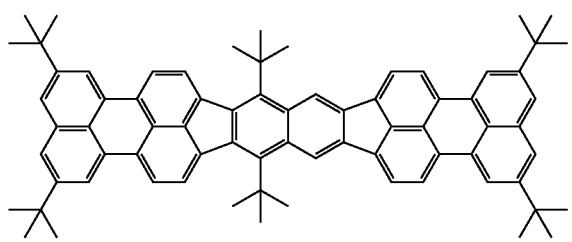
A56
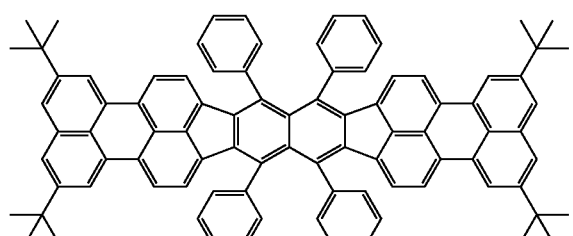
A56
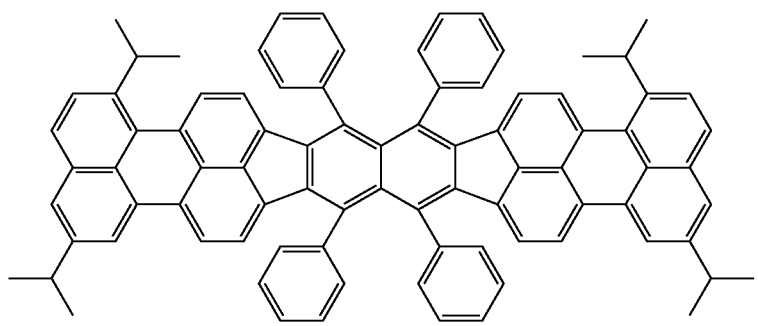
A57

A58
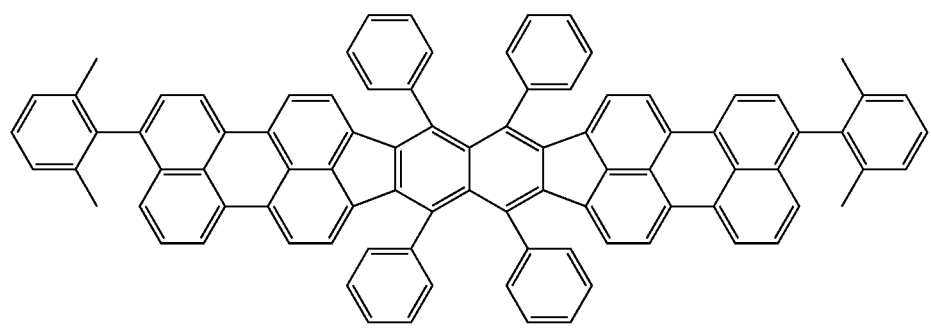
A59
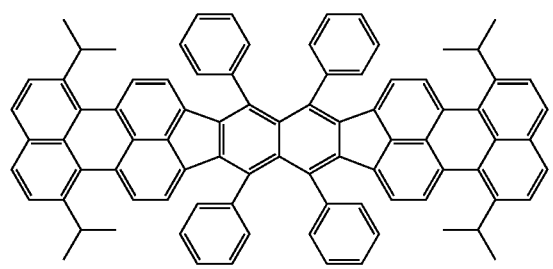
A60
A61
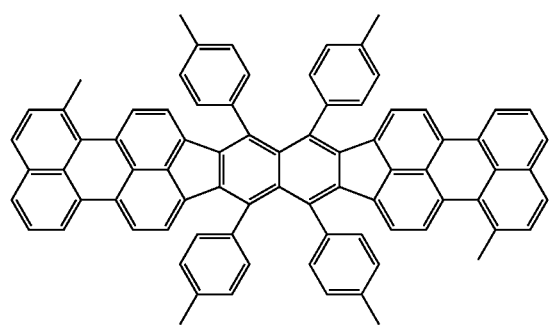
A62
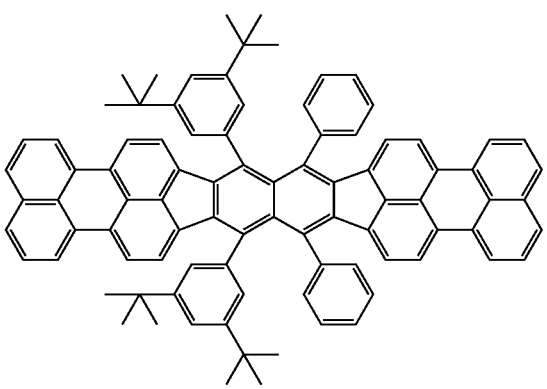
A63
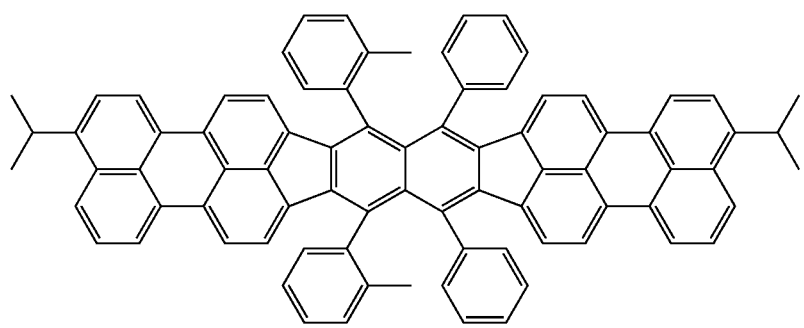

-continued
A64
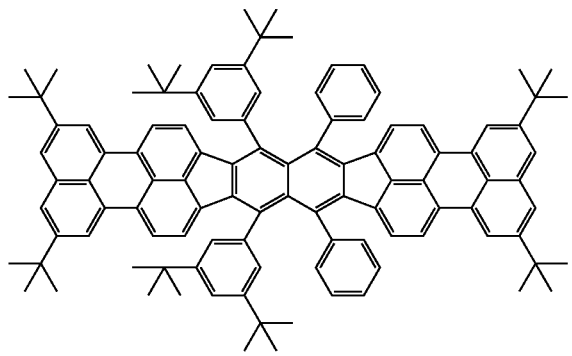
A65
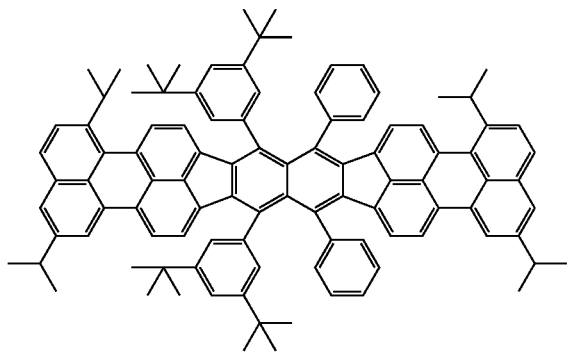
A66
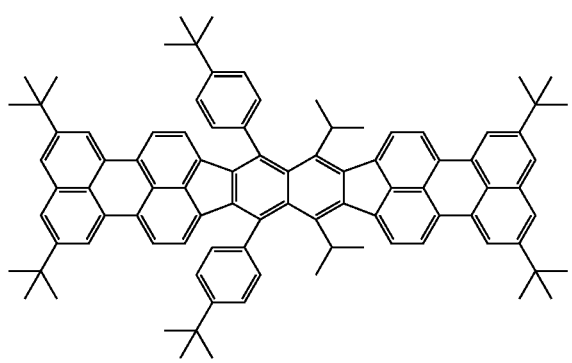
A67
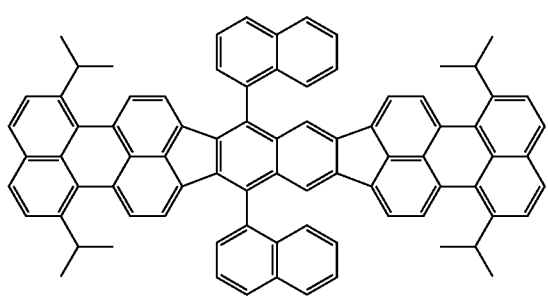
A68
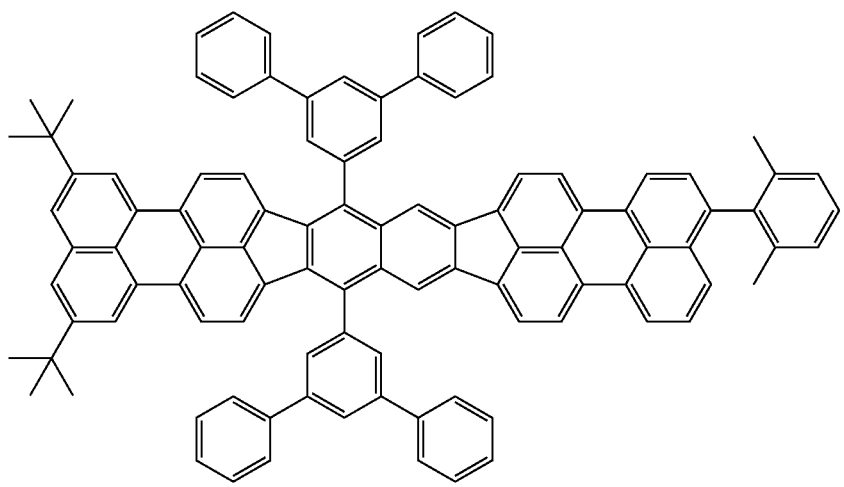
A69
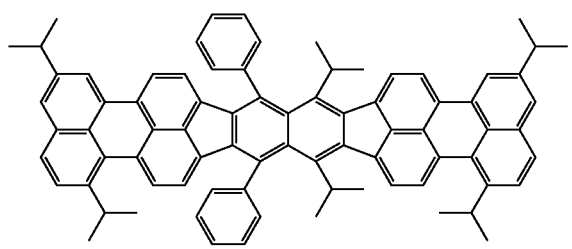
A70
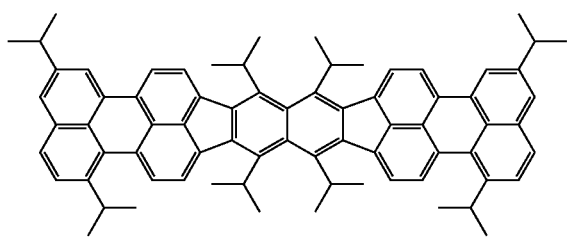

-continued
A71
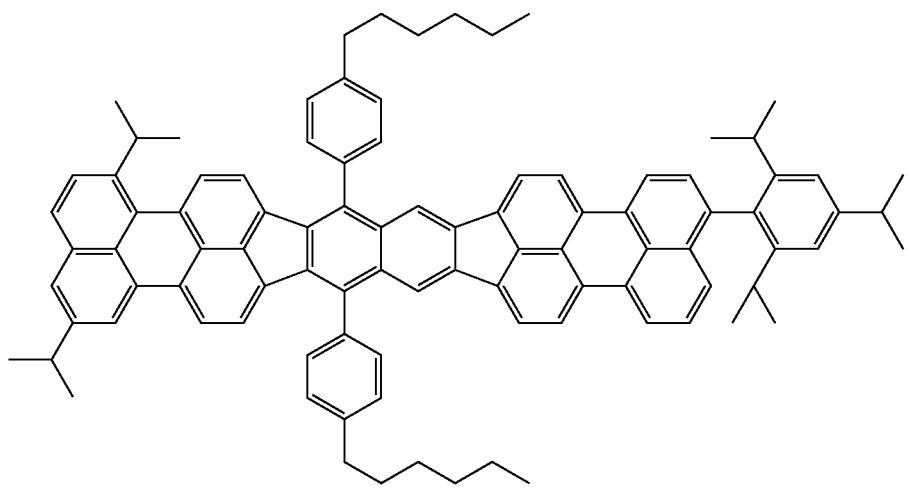
A72
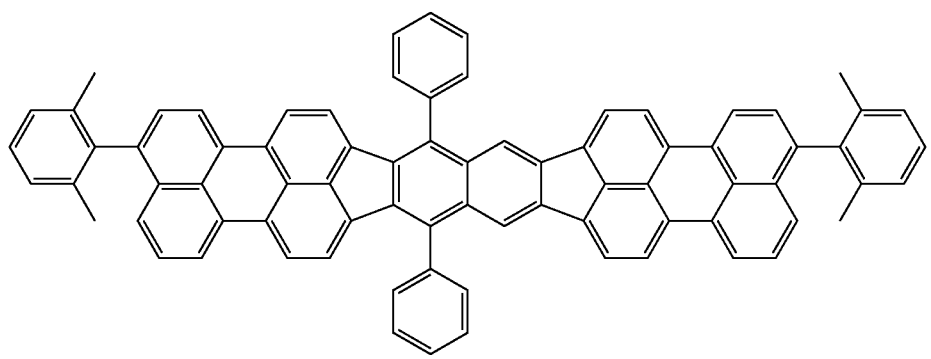
A73
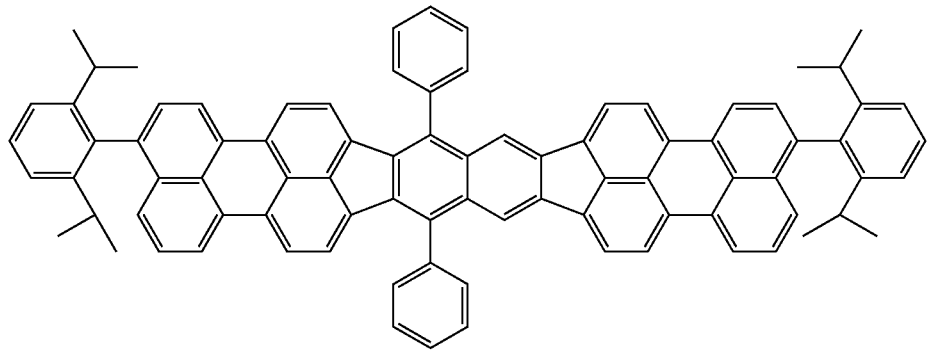
A74
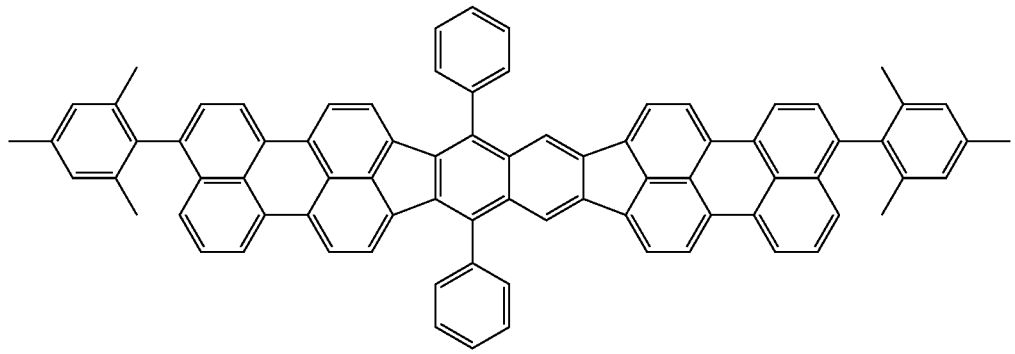

A75
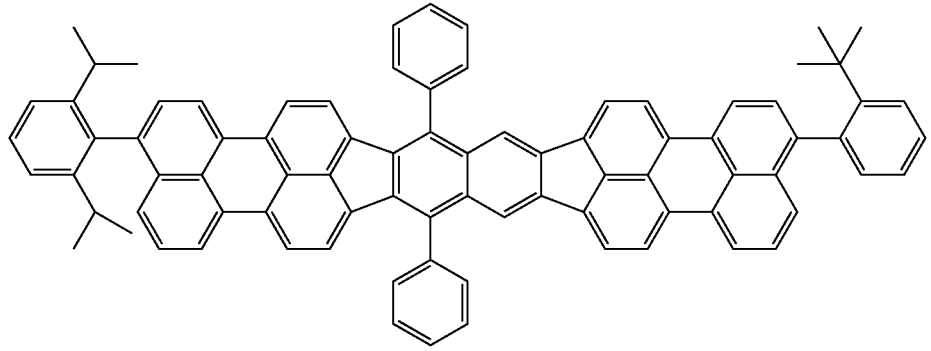
A76
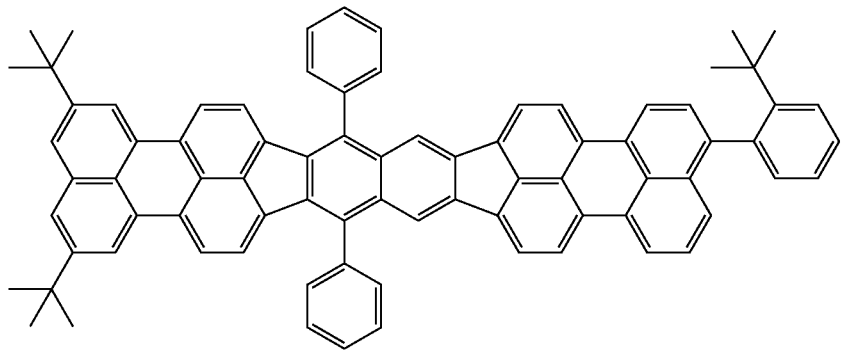
A77
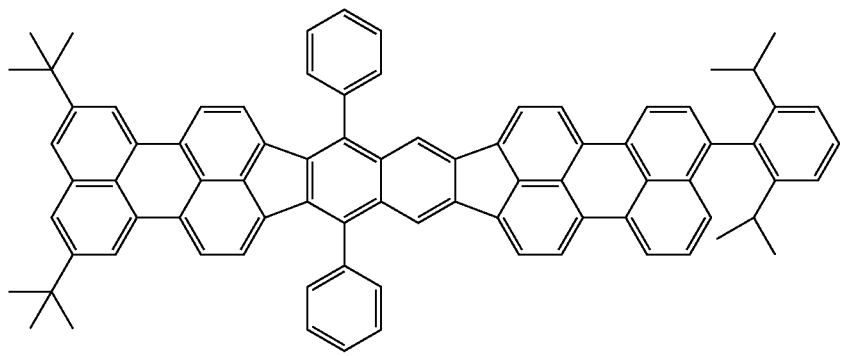
A78
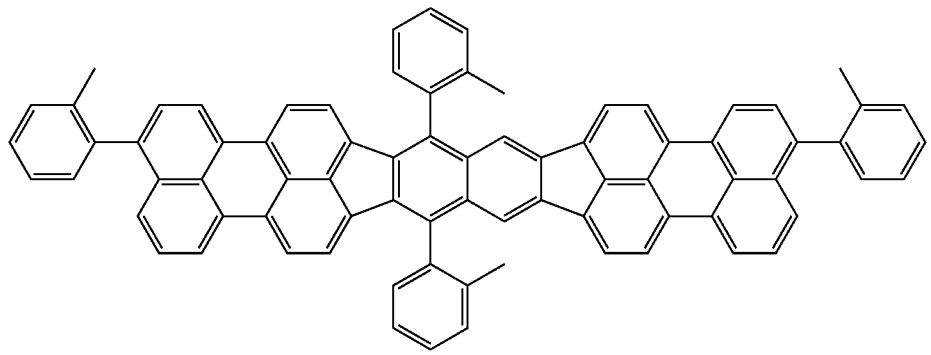

-continued
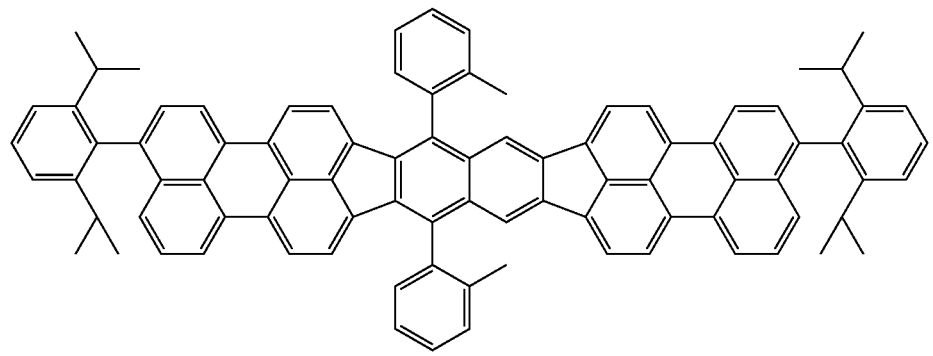
A79
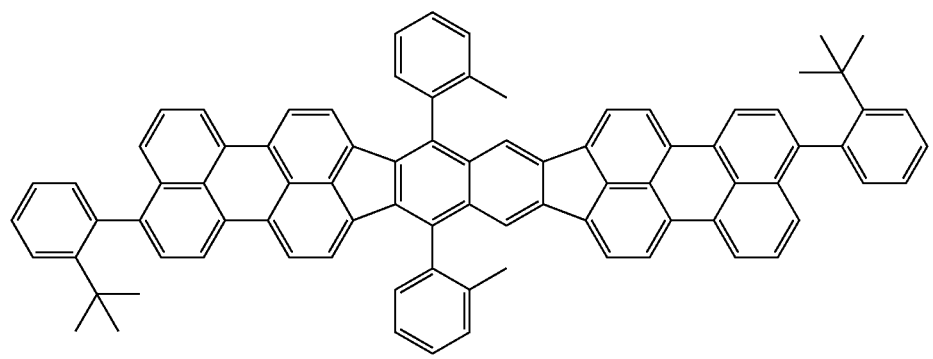
A80
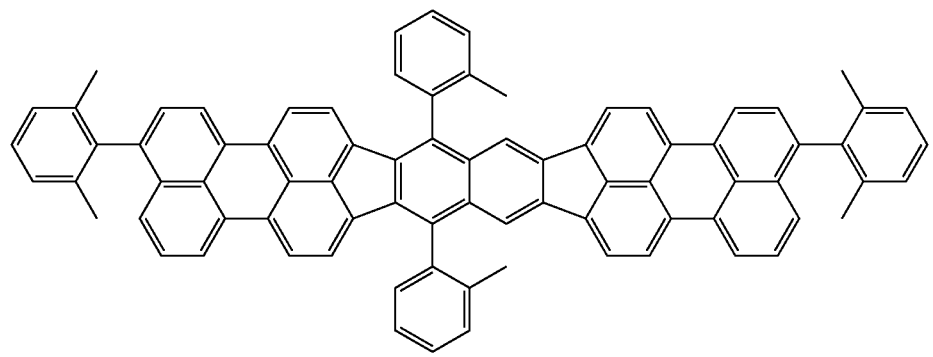
A81
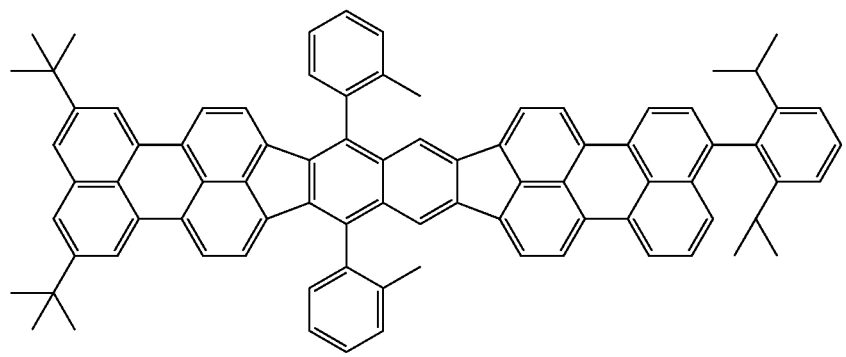
A82

-continued
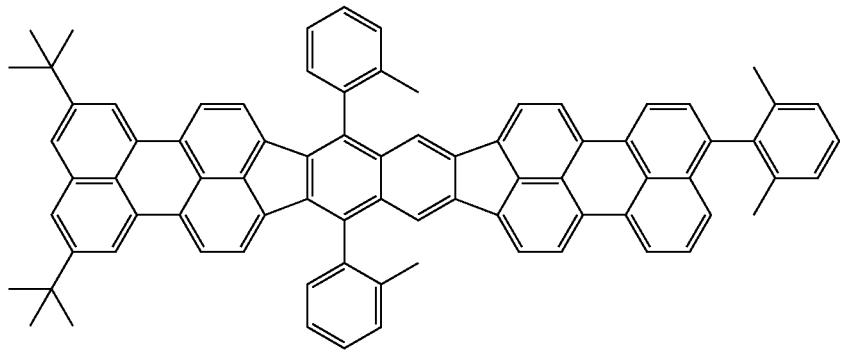
A83
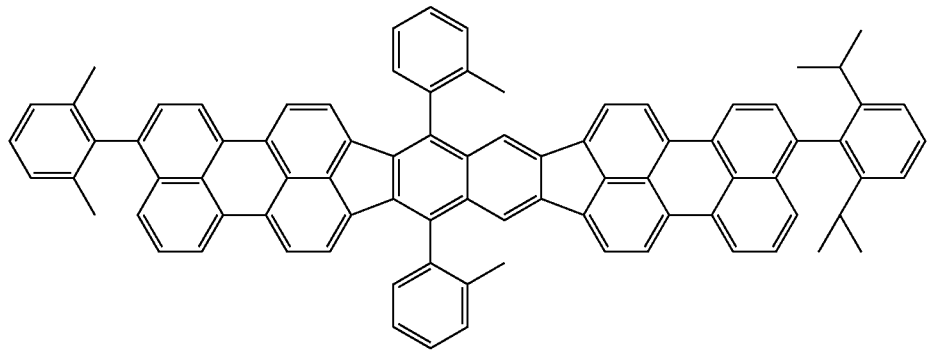
A84
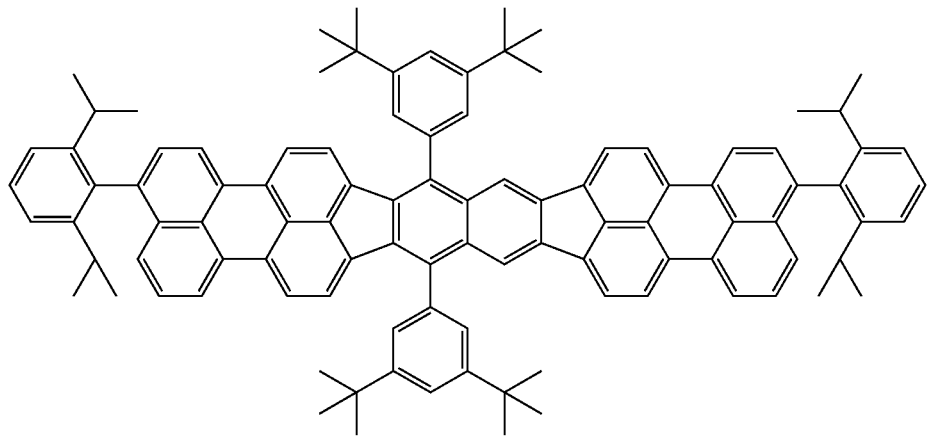
A85
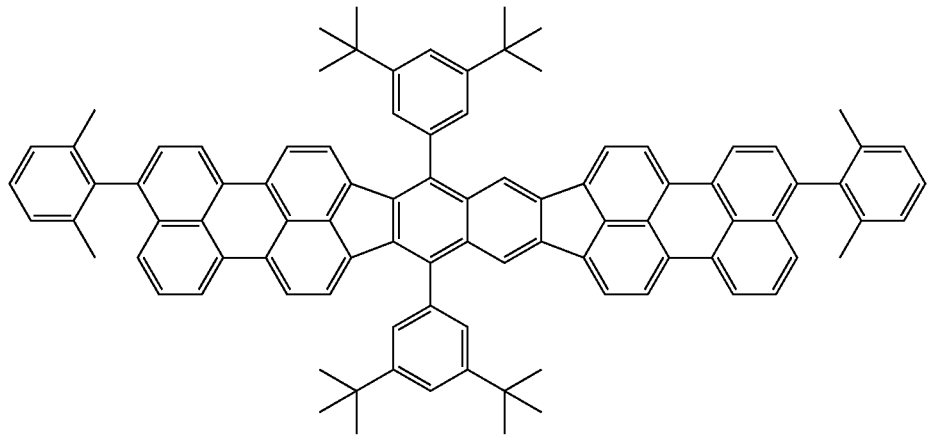
A86

-continued
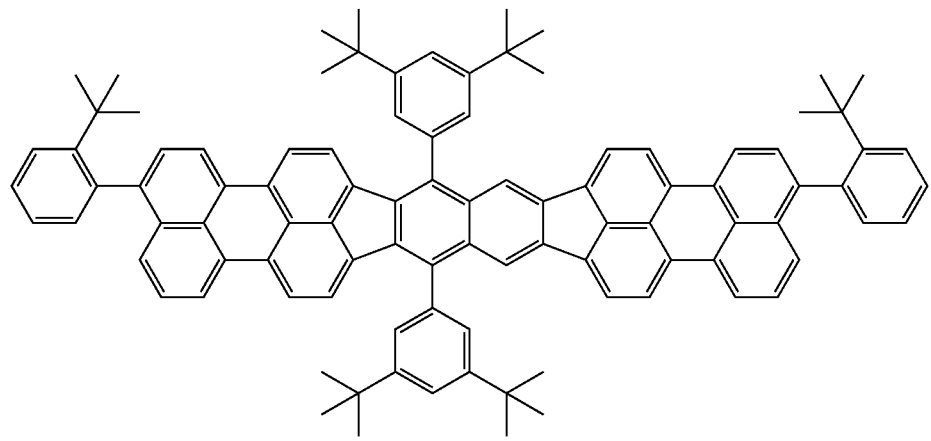
A87
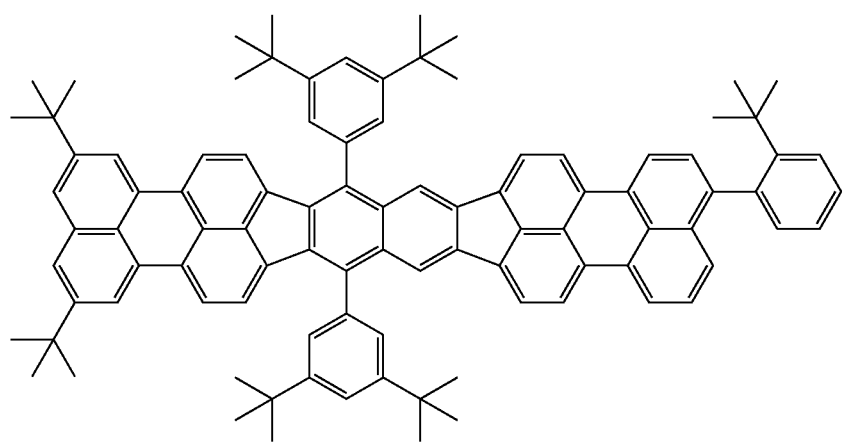
A88
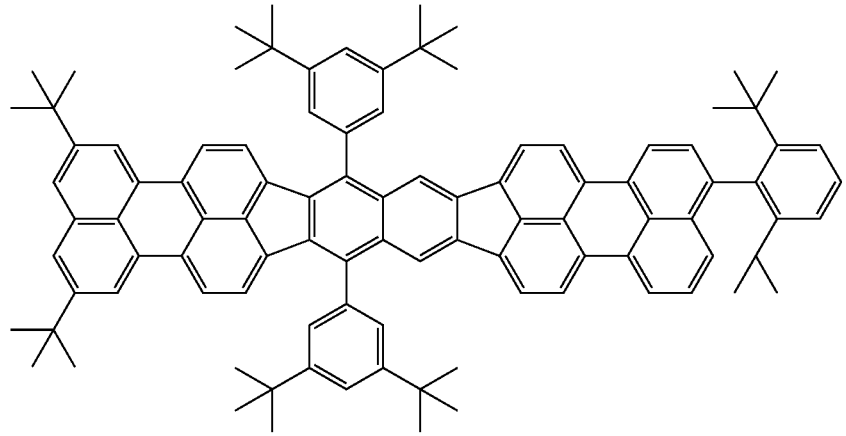
A89
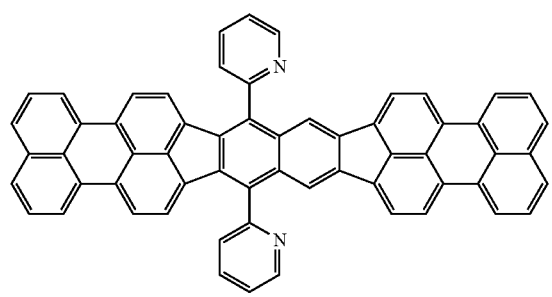
B1
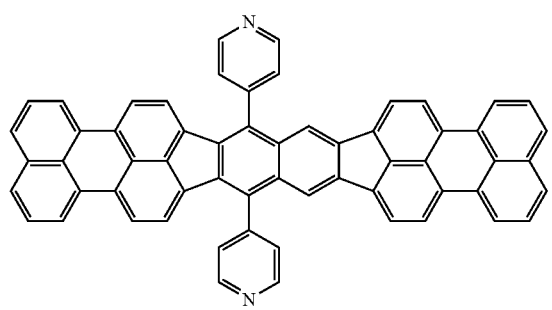
B2

-continued
B3
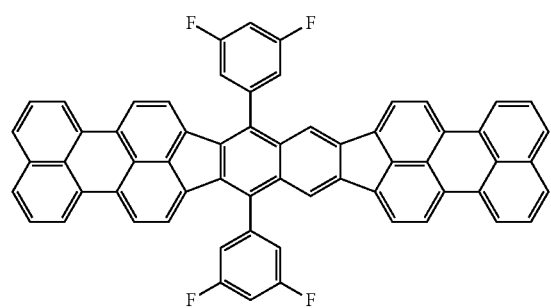
B4
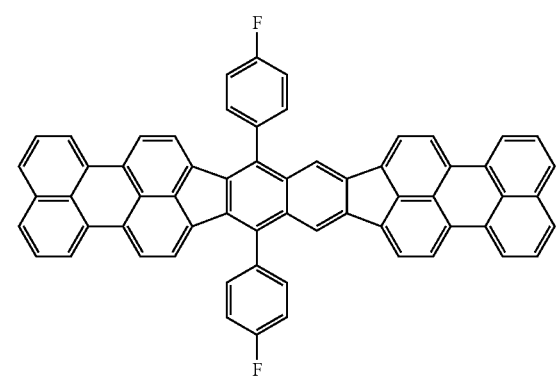
B5
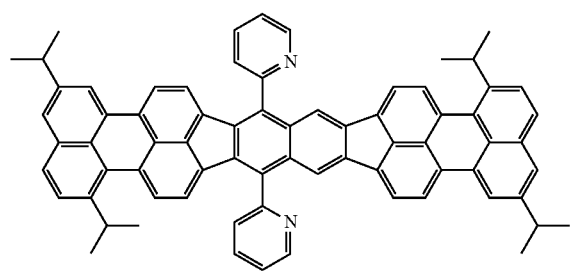
B6
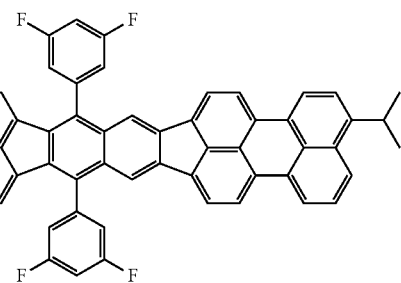
B7
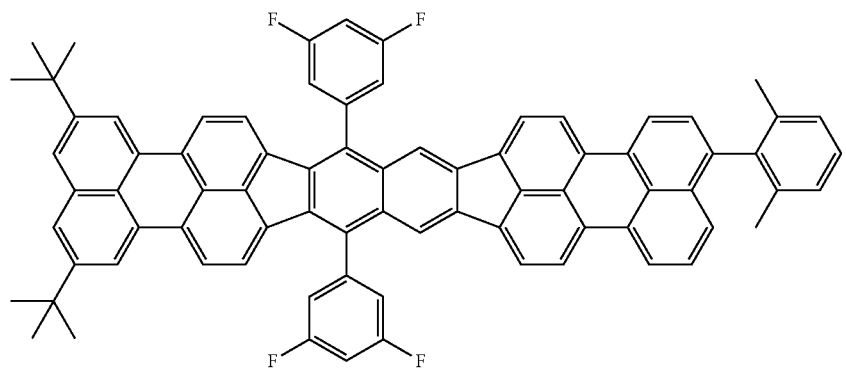
B8
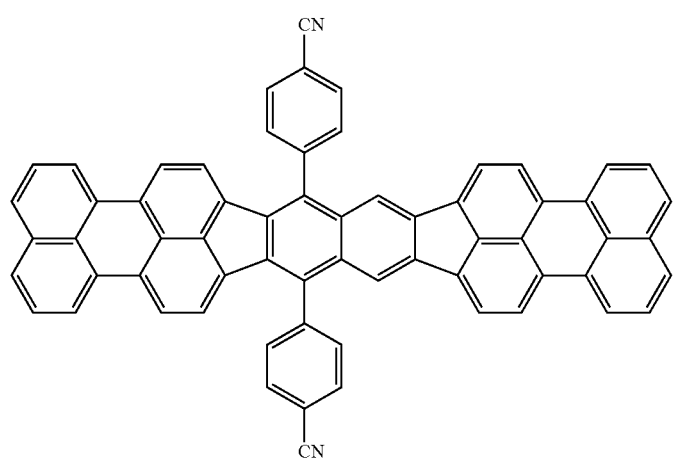

-continued
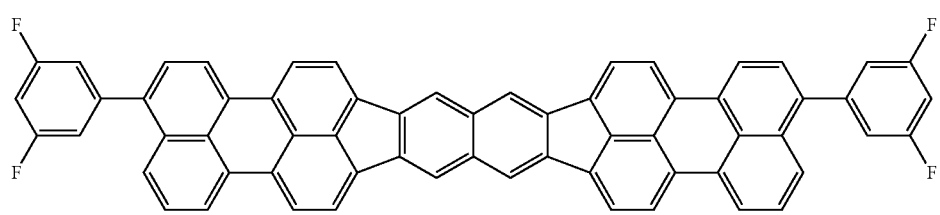
B9
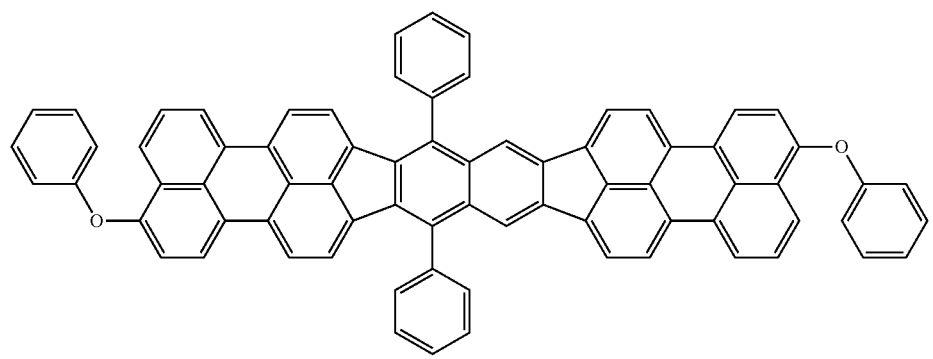
B10
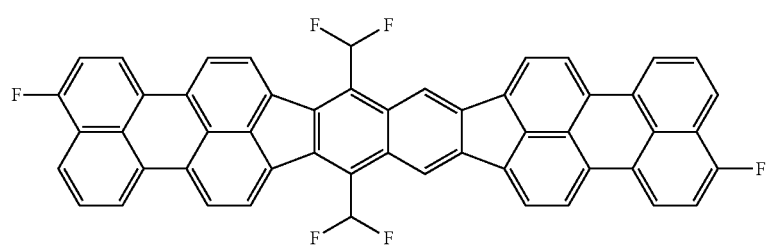
B11
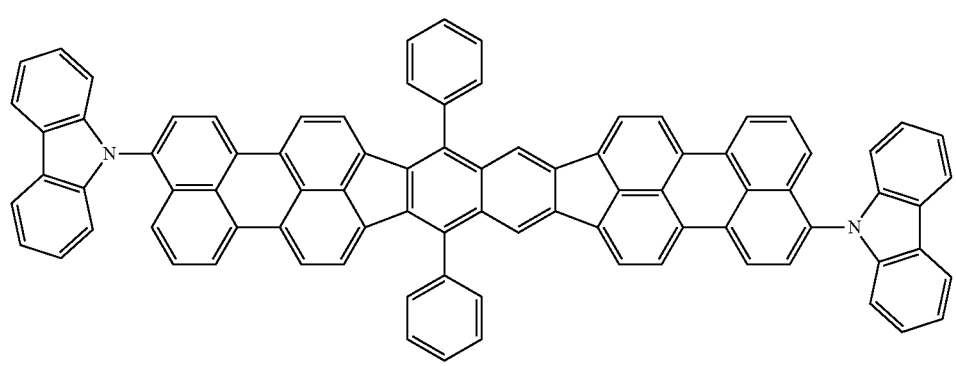
B12
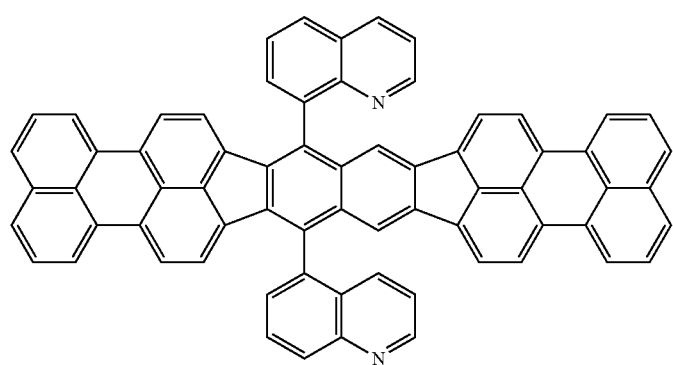
B13

-continued

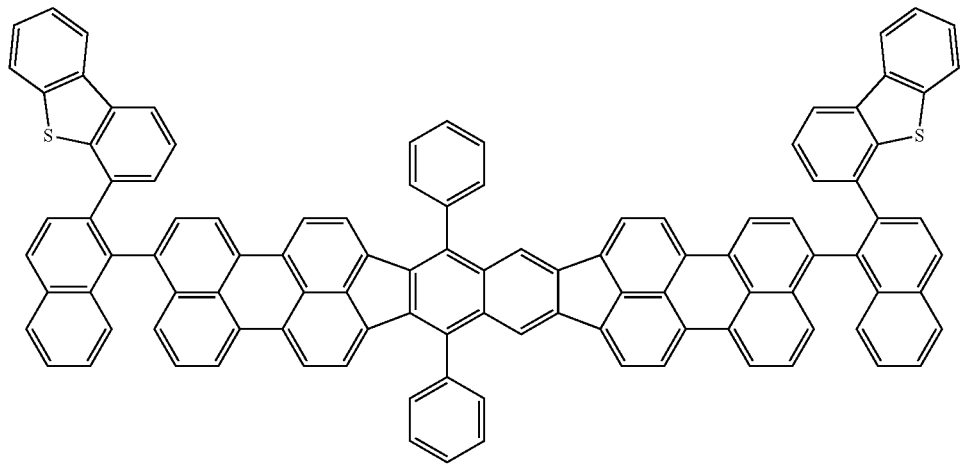
B14

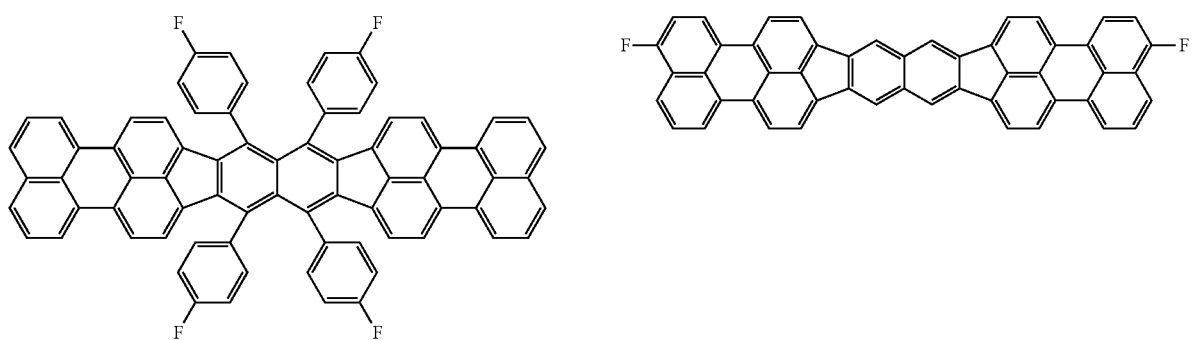
B15    B16

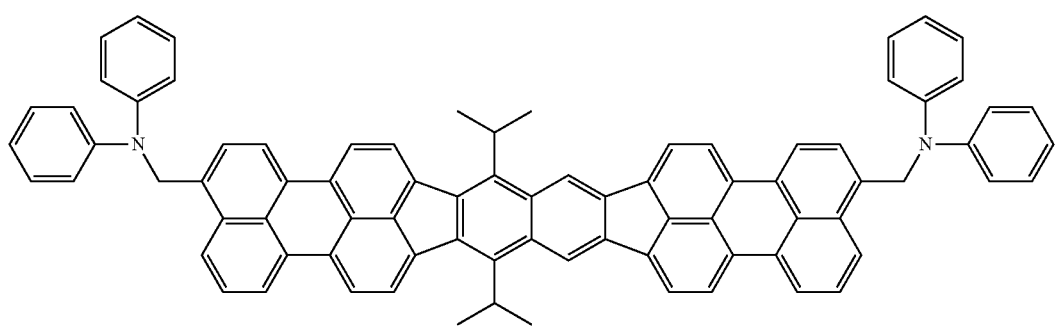
B17

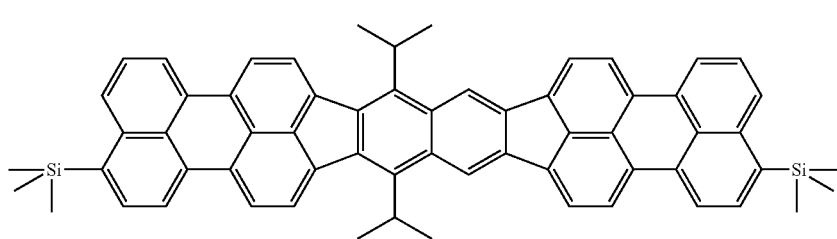
B18

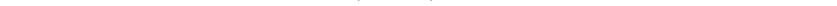

In the compounds belonging to Group A among the exemplary compounds shown above, the entire molecules of the compounds belonging to Group A are constituted by only hydrocarbon. Herein, the compounds constituted by only hydrocarbon generally have a low LUMO energy level. Therefore, this means that the compounds belonging to Group A are organic compounds having a low oxidation potential, i.e., stable to oxidization.

Therefore, the stability of the molecules of the organic compounds constituted by only hydrocarbon among the organic compounds according to this embodiment, i.e., the compounds belonging to Group A, is high, and thus are suitable.

In Group A, $R_1$, $R_2$, $R_{11}$, $R_{12}$, $R_{13}$, $R_{14}$, $R_{23}$, and $R_{24}$ of Formula (1) each are suitably independently selected from a hydrogen atom, an alkyl group, and an aryl group.

As the alkyl group, a methyl group, an isopropyl group, a tertiary butyl group, and the like are specifically mentioned but the alkyl group is not limited thereto.

As the aryl group, a phenyl group and the like are specifically mentioned but the aryl group is not limited thereto. The aryl group may have a substituent, and a methyl group, an isopropyl group, a tertiary butyl group, a phenyl group, and the like are specifically mentioned but it is not limited thereto.

In Group A, $R_6$, $R_7$, $R_{18}$, and $R_{19}$ of Formula (1) each are suitably independently selected from a hydrogen atom, an alkyl group, and an aryl group.

As the alkyl group, an isopropyl group, a tertiary butyl group, and the like are specifically mentioned but the alkyl group is not limited thereto.

As the aryl group, a phenyl group and the like are specifically mentioned but the aryl group is not limited thereto. The aryl group may have a substituent, and a methyl group, an isopropyl group, a tertiary butyl group, a phenyl group, and the like are specifically mentioned but it is not limited thereto.

In contrast, the compounds belonging to Group B among the exemplary compounds shown above, the substituent contains a hetero atom. In this case, the oxidation potential of the molecules themselves greatly changes. Or, the intermolecular interaction changes. The organic compounds of Group B in which the substituent contains a hetero atom are useful as an electron transporting, a hole transporting, or a hole trap type light emitting material. Particularly in fluorine-substituted compounds, the intermolecular interaction is suppressed, and therefore an improvement of sublimation properties can be expected. The organic compounds belonging to Group B can also be used at a high concentration of 100%.

Next, an organic light emitting device of this embodiment is described.

The organic light emitting device of this embodiment has at least an anode and a cathode which form a pair of electrodes and an organic compound layer disposed between these electrodes. In the organic light emitting device of this embodiment, the organic compound layer may be a single layer or a laminate containing a plurality of layers insofar as the organic light emitting device has a light emitting layer.

Herein, when the organic compound layer is a laminate containing a plurality of layers, the organic compound layer may have, in addition to the light emitting layer, a hole injecting layer, a hole transporting layer, an electron blocking layer, a hole/exciton blocking layer, an electron transporting layer, an electron injecting layer, and the like. The light emitting layer may be a single layer or a laminate containing a plurality of layers.

In the organic light emitting device of this embodiment, the organic compound according to this embodiment is contained at least one layer of the organic compound layer described above. Specifically, the organic compound according to this embodiment is contained in any one of the light emitting layer, the hole injecting layer, the hole transporting layer, the electron blocking layer, the light emitting layer, the hole/exciton blocking layer, the electron transporting layer, the electron injecting layer, and the like mentioned above. The organic compound according to this embodiment is suitably contained in the light emitting layer.

In the organic light emitting device of this embodiment, when the organic compound according to this embodiment is contained in the light emitting layer, the light emitting layer may be a layer containing only the organic compound according to this embodiment or may be a layer containing the organic compound according to this embodiment and other compounds. Herein, when the light emitting layer is a layer containing the organic compound according to this embodiment and other compounds, the organic compound according to this embodiment may be used as a host of the light emitting layer or may be used as a guest. Or, the organic compound according to this embodiment may be used as an assist material which can be contained in the light emitting layer.

Herein, the host is a compound with the highest weight ratio among the compounds constituting the light emitting layer. The guest is a compound whose weight ratio is lower than that of the host among the compounds constituting the light emitting layer and is a compound which performs main light emission. The assist material is a compound whose weight ratio is lower than that of the host among the compounds constituting the light emitting layer and is a compound which assists the light emission of the guest. The assist material is also referred to as a second host.

Herein, when the organic compound according to this embodiment is used as the guest of the light emitting layer, the concentration of the guest is suitably 0.01% by weight or more and 20% by weight or lower and more suitably 0.1% by weight or more and 5% by weight or lower based on the total weight of the light emitting layer.

When the organic compound according to this embodiment is used as the guest of the light emitting layer, it is suitable to use a material having a LUMO higher than that of the organic compound according to this embodiment (material in having a LUMO closer to the vacuum level) as the host. This is because the LUMO of the organic compound according to this embodiment is low, and therefore, the use of a material having a LUMO higher than that of the organic compound according to this embodiment as the host allows the organic compound according to this embodiment to receive a larger number of electrons to be supplied to the host of the light emitting layer.

The present inventors have conducted various examinations, and have found that when the organic compound according to this embodiment is used as the host or the guest of the light emitting layer, particularly as the guest of the light emitting layer, a device having an optical output with high efficiency and high luminance and extremely high durability is obtained. The light emitting layer may be a single layer or a multilayer. By compounding a light emitting material emitting another color of light, the color of the light can be mixed with a red light color which is the color of the light of this embodiment. The multilayer means a state where the light emitting layer and another light emitting layer are laminated. In this case, the color of the light emitted from the organic light emitting device is not limited to red. More specifically, white color may be acceptable or an intermediate color may be acceptable. In the case of white color, the other light emitting layer emits light of color other than red, i.e., blue light or green light. With respect to a film formation method, film formation is performed by vapor deposition or film formation by application. The details thereof are described in detail in Examples described later.

The organic compound according to this embodiment can be used as a constituent material of the organic compound layer other than the light emitting layer constituting the organic light emitting device of this embodiment. Specifically, the organic compound according to this embodiment may be used as a constituent material of the electron transporting layer, the electron injecting layer, the hole transporting layer, the hole injecting layer, the hole blocking layer, or the like. In this case, the color of the light emitted from the organic light emitting device is not limited to red. More specifically, white color may be acceptable or an intermediate color may be acceptable.

Herein, besides the organic compound according to this embodiment, known low molecular weight compounds or high molecular weight compounds can be used as required. Hole injecting compounds, hole transporting compounds, compounds serving as a host, light emitting compounds, electron injecting compounds, electron transporting compounds can be used irrespective of the molecular weight, i.e., low molecular weight or high molecular weight.

Examples of the compounds are shown below.

The hole injecting compounds and the hole transporting compounds are suitably materials having a high hole mobility. Mentioned as the low molecular weight compounds or the high molecular weight compounds having hole injecting properties or hole transporting properties are a triarylamine derivative, a phenylenediamine derivative, a stilbene derivative, a phthalocyanine derivative, a porphyrin derivative, poly (vinyl carbazole), poly(thiophene), and other conductive polymers but the compounds are not limited thereto.

As the host, the compounds shown in the following Table 2 are specifically mentioned.

TABLE 2

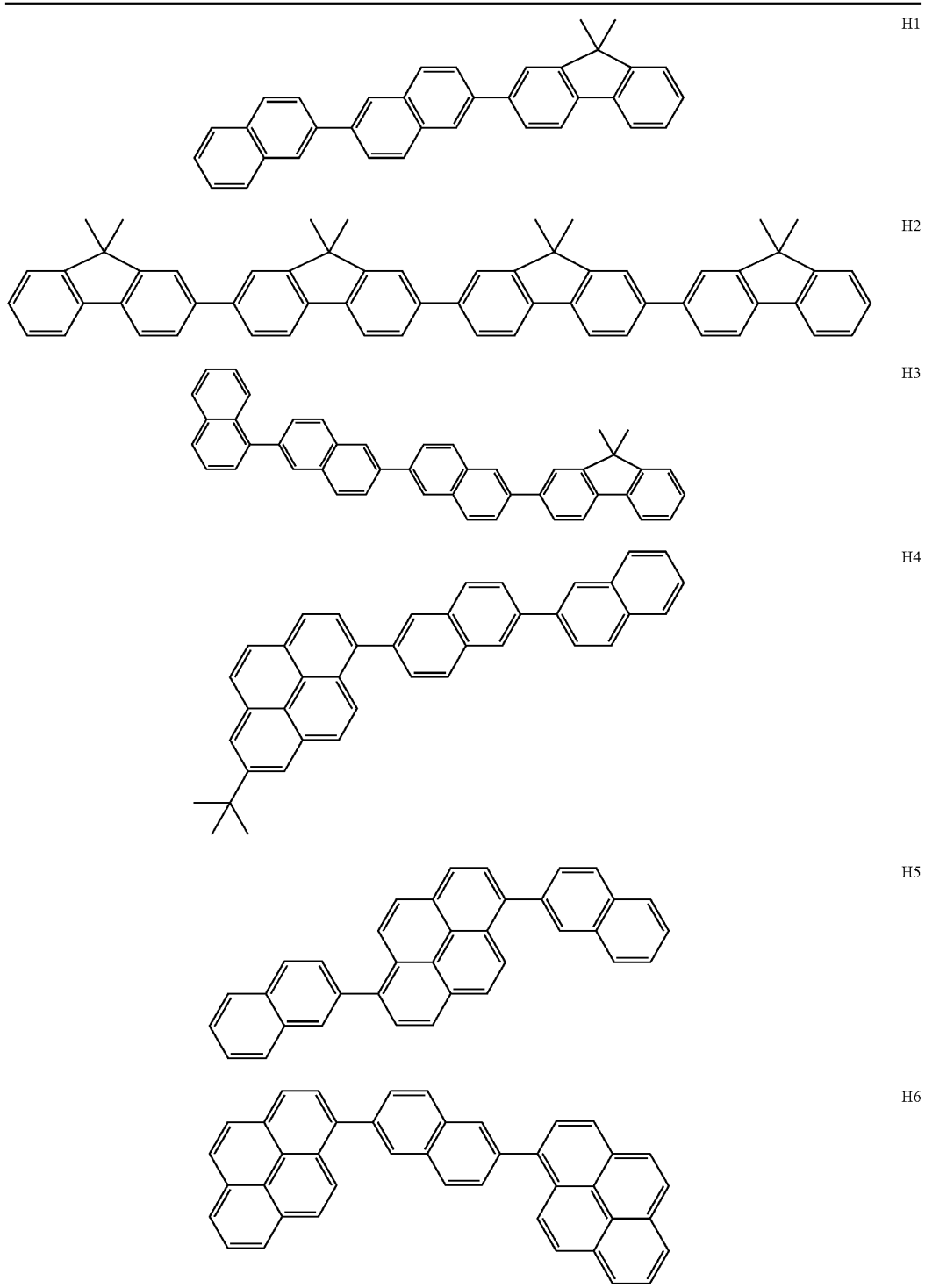

TABLE 2-continued
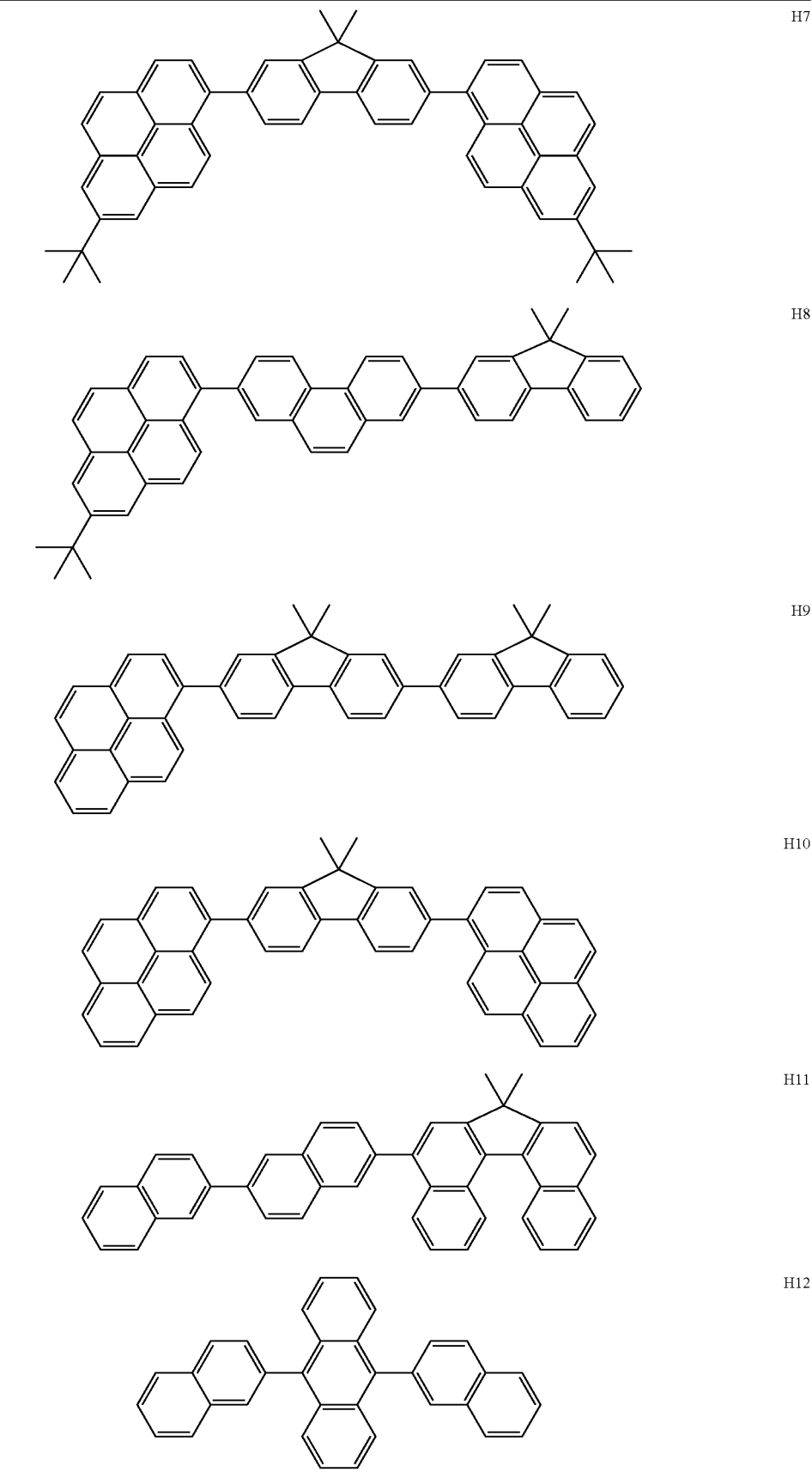

TABLE 2-continued
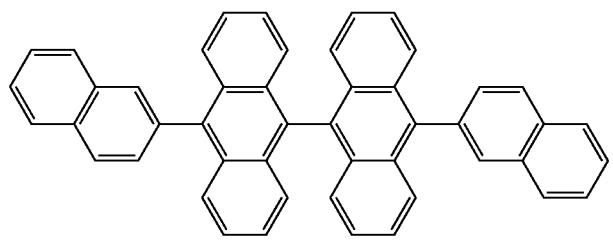 [SMILES: c1ccc2cc(-c3c4ccccc4c(-c4c5ccccc5c(-c5ccc6ccccc6c5)c5ccccc45)c4ccccc34)ccc2c1] H13
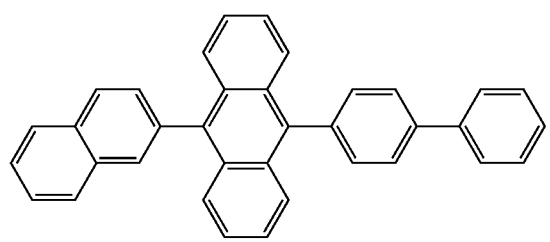 [SMILES: c1ccc(-c2ccc(-c3c4ccccc4c(-c4ccc5ccccc5c4)c4ccccc34)cc2)cc1] H14
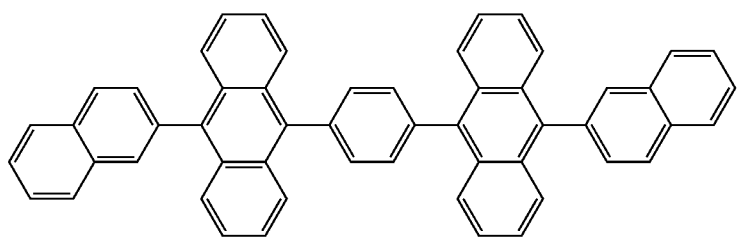 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H15
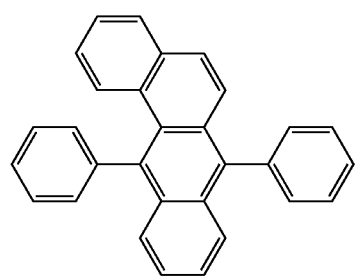 [SMILES: c1ccc(-c2c3ccccc3c(-c3ccccc3)c3c2ccc2ccccc23)cc1] H16
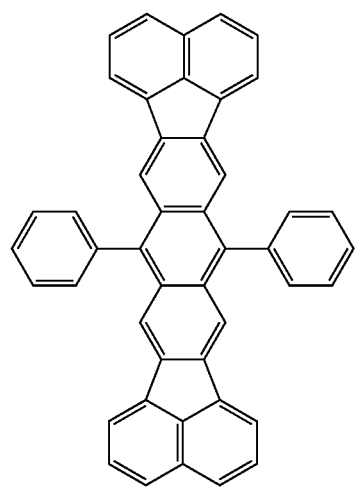 [SMILES: c1ccc(-c2c3cc4c(cc3c(-c3ccccc3)c3cc5c(cc23)-c2cccc3cccc-5c23)-c2cccc3cccc-4c23)cc1] H17

TABLE 2-continued
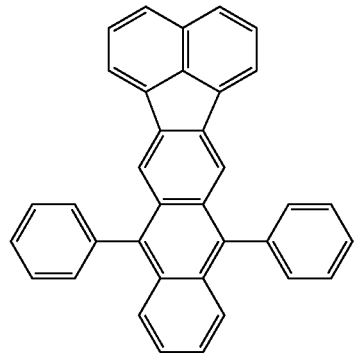 [SMILES: c1ccc(-c2c3ccccc3c(-c3ccccc3)c3cc4c(cc23)-c2cccc3cccc-4c23)cc1] H18
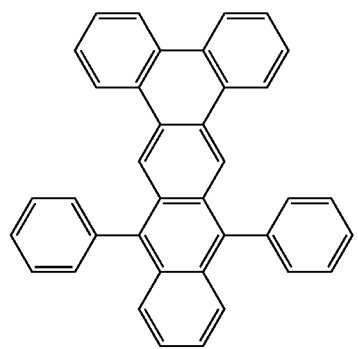 [SMILES: c1ccc(-c2c3ccccc3c(-c3ccccc3)c3cc4c5ccccc5c5ccccc5c4cc23)cc1] H19
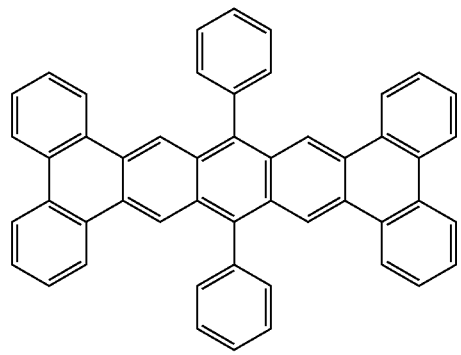 [SMILES: c1ccc(-c2c3cc4c5ccccc5c5ccccc5c4cc3c(-c3ccccc3)c3cc4c5ccccc5c5ccccc5c4cc23)cc1] H20
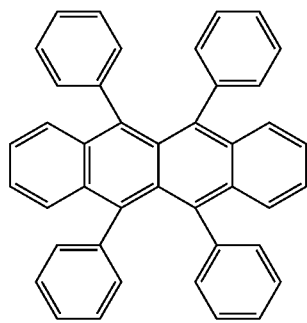 [SMILES: c1ccc(-c2c3ccccc3c(-c3ccccc3)c3c(-c4ccccc4)c4ccccc4c(-c4ccccc4)c23)cc1] H21

TABLE 2-continued
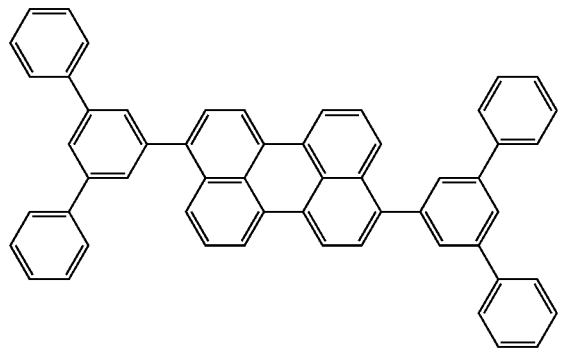 [SMILES: c1ccc(-c2cc(-c3ccccc3)cc(-c3ccc4c5cccc6c(-c7cc(-c8ccccc8)cc(-c8ccccc8)c7)ccc(c7cccc3c74)c65)c2)cc1] H22
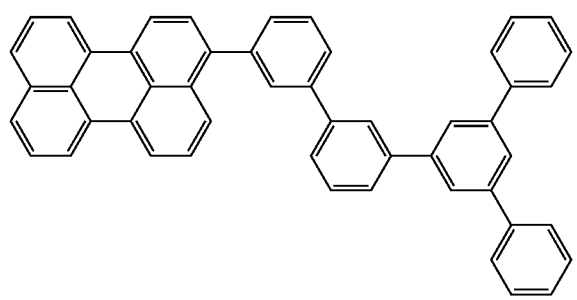 [SMILES: c1ccc(-c2cc(-c3ccccc3)cc(-c3cccc(-c4cccc(-c5ccc6c7cccc8cccc(c9cccc5c96)c87)c4)c3)c2)cc1] H23
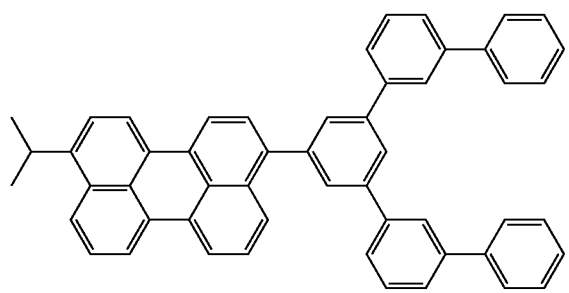 [SMILES: CC(C)c1ccc2c3ccc(-c4cc(-c5cccc(-c6ccccc6)c5)cc(-c5cccc(-c6ccccc6)c5)c4)c4cccc(c5cccc1c52)c43] H24
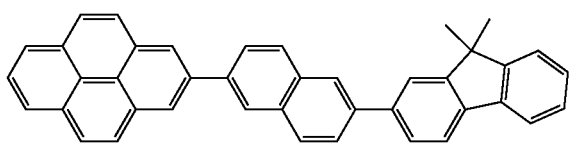 [SMILES: CC1(C)c2ccccc2-c2ccc(-c3ccc4cc(-c5cc6ccc7cccc8ccc(c5)c6c78)ccc4c3)cc21] H25
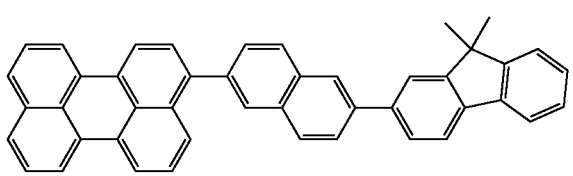 [SMILES: CC1(C)c2ccccc2-c2ccc(-c3ccc4cc(-c5ccc6c7cccc8cccc(c9cccc5c96)c87)ccc4c3)cc21] H26
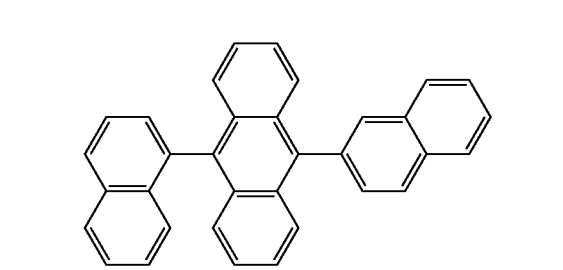 [SMILES: c1ccc2cc(-c3c4ccccc4c(-c4cccc5ccccc45)c4ccccc34)ccc2c1] H27

TABLE 2-continued

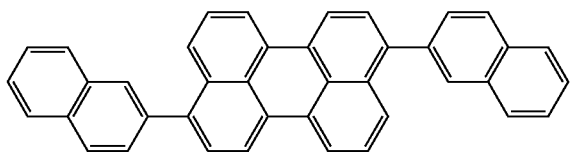 [SMILES: c1ccc2cc(-c3ccc4c5cccc6c(-c7ccc8ccccc8c7)ccc(c7cccc3c74)c65)ccc2c1]

H28

However, the invention is not limited thereto. Compounds which are derivatives of the compounds shown in Table 2 can also be used as the host. In addition to the compounds, condensed compounds (e.g., a fluorene derivative, a naphthalene derivative, an anthracene derivative, a pyrene derivative, a carbazole derivative, a quinoxaline derivative, and a quinoline derivative), organic aluminum complexes, such as tris(8-quinolinolato)aluminum, organic zinc complexes, and high molecular weight derivatives, such as a triphenylamine derivative, a poly(fluorene) derivative, and a poly(phenylene) derivative, are mentioned but the invention is not limited thereto.

The electron injecting compound and the electron transporting compound are selected as appropriate considering, for example, the balance with the hole mobility of the hole injecting compound and the hole transporting compound. Mentioned as compounds having electron injecting performance or electron transporting performance are an oxadiazole derivative, an oxazole derivative, a pyrazine derivative, a triazole derivative, a triazine derivative, a quinoline derivative, a quinoxaline derivative, a phenanthroline derivative, an organic aluminium complex, and the like but the compounds are not limited thereto.

As constituent materials of an anode, materials having as high a work function as possible are suitably used. For example, mentioned are simple metal substances, such as gold, platinum, silver, copper, nickel, palladium, cobalt, selenium, vanadium, and tungsten, alloys obtained by combining a plurality of the simple metal substances, and metal oxides, such as tin oxide, zinc oxide, indium oxide, indium tin oxide (ITO), and indium zinc oxide. Conductive polymers, such as polyaniline, polypyrrole, and polythiophene, may be acceptable. These electrode substances may be used singly or a plurality kinds of the substances may be used in combination. The anode may be a single layer structure or a multilayer structure.

In contrast, as constituent materials of a cathode, materials having a low work function are suitably used. For example, mentioned are simple metal substances, such as alkaline metals, such as lithium, alkaline earth metals, such as calcium, aluminum, titanium, manganese, silver, lead, and chromium. Or, alloys obtained by combining a plurality of these simple metal substances can also be used. For example, magnesium-silver, aluminum-lithium, aluminum-magnesium, and the like can be used. Metal oxides, such as indium tin oxide (ITO), can also be utilized. These electrode substances may be used singly or a plurality kinds of the substances may be used in combination. The cathode may be a single layer structure or a multilayer structure.

In the organic light emitting device of this embodiment, a layer containing the organic compound according to this embodiment and a layer containing the other organic compound are formed by the following methods. In general, a thin film is formed by a vacuum evaporation method, an ionization vapor deposition method, sputtering, plasma, or a known application method (e.g., spin coating, dipping, a cast method, an LB method, and an ink jet method) after dissolving in a suitable solvent. Herein, when the layer is formed by a vacuum evaporation method, a solution application method, or the like, crystallization is hard to occur and the stability over time is excellent. When the film formation is performed by an application method, the film can also be formed in combination with a suitable binder resin.

Mentioned as the above-mentioned binder resin are polyvinyl carbazole resin, polycarbonate resin, polyester resin, ABS resin, acrylic resin, polyimide resin, phenol resin, epoxy resin, silicone resin, urea resin, and the like but the binder resin is not limited thereto. The binder resin may be used singly as a homopolymer or a copolymer or as a mixture of two or more kinds thereof. Furthermore, additive agents, such as a known plasticizer, antioxidant, and UV absorber, may be used in combination as required.

The organic light emitting device according to aspects of the invention can be used as a constituent member of a display device or a lighting device. In addition thereto, the organic light emitting device according to aspects of the invention is applied to an exposure light source of an electrophotographic image forming device, a back light of a liquid crystal display, a white light source using a color filter, and the like. The color filter is a filter through which three colors of red, green, and blue penetrate, for example.

The display device has the organic light emitting device of this embodiment at a display portion. The display portion has a plurality of pixels. The pixel has the organic light emitting device of this embodiment and a TFT element which is an example of a switching element for controlling the light emission luminosity, and the anode or the cathode of the organic light emitting device and the drain electrode or the source electrode of the TFT element are electrically connected. Herein, the display device can be used as an image display device of PC.

The display device may be an image input device which has an input portion which inputs image information from an area CCD, a linear CCD, a memory card, or the like and which outputs the input image to the display portion. As the display portion of an imaging device or an ink jet printer, both an image output function for displaying image information input from the outside and an input function for inputting processing information to an image as an operation panel may be provided. The display device may also be used for the display portion of a multifunction printer.

The lighting device is a device which illuminates the interior of a room. The lighting device may be one which emits light of white color, natural white color, or any color of blue to red. The lighting device may have the organic light emitting device according to this embodiment and an inverter circuit to be connected thereto. The white color refers to one having a color temperature of 4200 K and the natural white color refers to one having a color temperature of 5000 K. In addition thereto, 3000 K, 3500 K, or the like may be acceptable. The lighting device may have a color filter.

The electrophotographic image forming device, such as a laser beam printer or a copying machine, may have an exposure unit having the organic light emitting device according to this embodiment. The exposure unit is a unit for exposing a photoconductor in order for a photoconductor drum to obtain an electrostatic latent image. The exposure unit may have one or two or more of the organic light emitting devices. When the exposure unit has two or more of the organic light emitting devices, a control unit capable of independently controlling light emission and non-light emission of each organic light emitting device is provided. The plurality of organic light emitting devices are disposed in one row along the longitudinal direction of the photoconductor drum. A lens may be provided between the organic light emitting device and the photoconductor drum.

Next, a display device employing the organic light emitting device of this embodiment is described with reference to FIG. 2.

Figure 2:
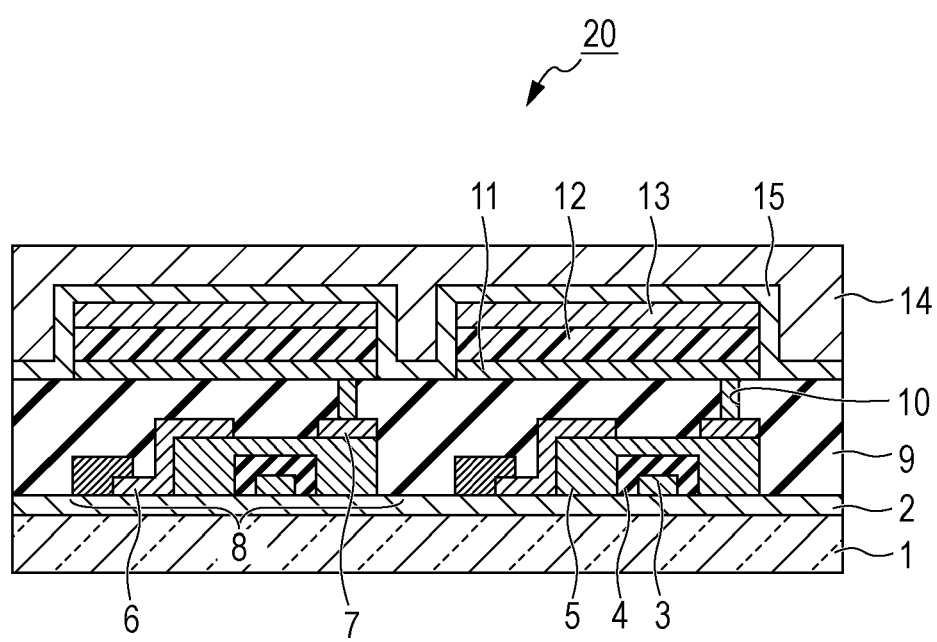
FIG. 2 is a cross-sectional schematic view illustrating an example of a display device having an organic light emitting device of the invention and a TFT element which is an example of a switching element which is electrically connected to the organic light emitting device.

FIG. 2 is a cross-sectional schematic view illustrating an example of a display device having the organic light emitting device of this embodiment and a TFT element which is an example of a switching element to be electrically connected to the organic light emitting device. In a display device 20 of FIG. 2, two pairs of the organic light emitting device and the TFT element are illustrated. The details of the configuration are described below.

The display device 20 of FIG. 2 is provided with a substrate 1, such as glass, and a moisture barrier film 2 for protecting the TFT element or the organic compound layer on the substrate 1. The reference numeral 3 denotes a metal gate electrode 3. The reference numeral 4 denotes a gate insulation film 4 and the reference numeral 5 denotes a semiconductor layer.

The TFT element 8 has a semiconductor layer 5, a drain electrode 6, and a source electrode 7. An insulation film 9 is provided on the TFT element 8. An anode 11 of the organic light emitting device and the source electrode 7 are connected through a contact hole 10. The configuration of the display device is not limited to the configuration and either one of the anode or the cathode may be connected to either one of the source electrode or the drain electrode of the TFT element.

In the display device 20 of FIG. 2, the organic compound layer 12 is illustrated in such a manner as to have a single organic compound layer or have a plurality of organic compound layers in the form of one layer. On a cathode 13, a first protective layer 14 or a second protective layer 15 for suppressing degradation of the organic light emitting device are provided.

In the display device according to this embodiment, the switching element is not particularly limited and a transistor or an MIM element may be used. As the transistor, a thin film transistor employing a single crystal silicon, an amorphous silicon type transistor element, or the like may be used. The thin film transistor is also referred to as a TFT element.

EXAMPLES

Hereinafter, aspects of the invention are described with reference to Examples. However, the invention is not limited thereto.

Example 1

Synthesis of Exemplary Compound A2

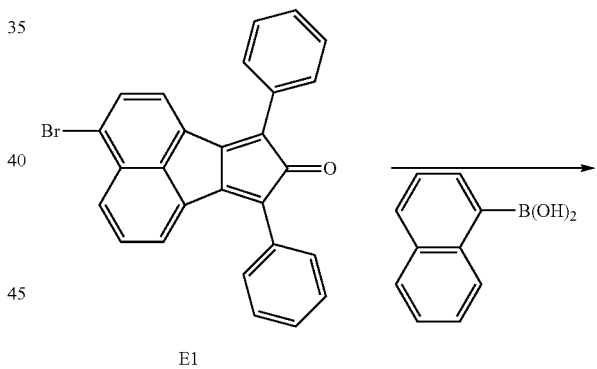

E1

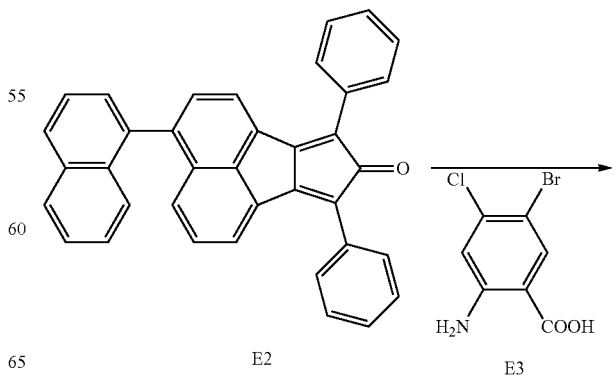

E2

E3

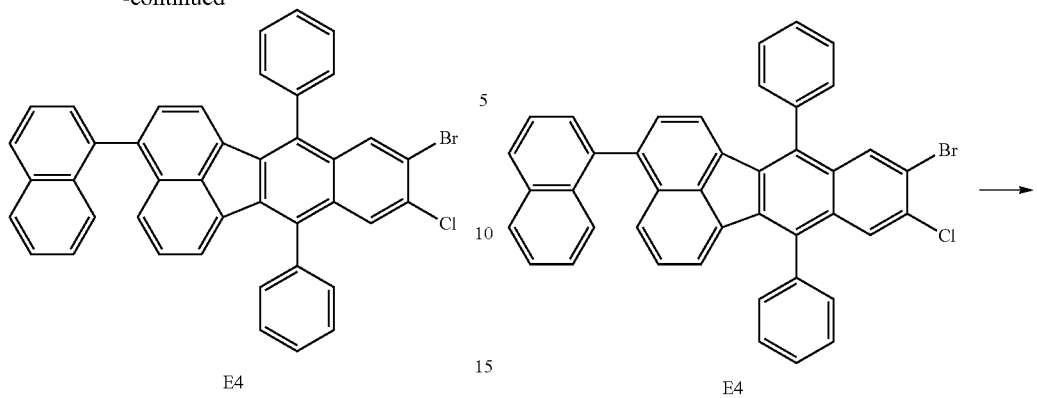

(1) Synthesis of Compound E2

The following reagents and solvent were charged in a 500 ml eggplant flask. The compound E1 described later is a compound synthesized according to Japanese Patent Laid-Open No. 2010-254610.

Compound E1: 4.35 g (10 mmol)

1-naphthalene boronic acid: 1.72 g (10 mmol)

$Pd(PPh_3)_4$: 0.2 g

Toluene: 100 ml

Ethanol: 50 ml

2 M aqueous sodium carbonate solution: 100 ml

Next, the reaction solution was heated to 80° C. under nitrogen flow, and stirred at this temperature (80° C.) for 8 hours. After the end of the reaction, ethanol was added to precipitate crystals, the crystals were filtered off, and then the crystals were successively washed with water, ethanol, and heptane. Next, the obtained crystals were dissolved in toluene by heating, purified by column chromatography (toluene/heptane=1:1), and then re-crystallized with chloroform/methanol, thereby obtaining 3.95 g (Yield: 82%) of a dark green compound E2.

(2) Synthesis of Compound E4

The following reagents and solvent were charged in a 100 ml eggplant flask.

Compound E2: 3.86 g (8 mmol)

Compound E3: 2.51 g (10 mmol)

Isoamyl nitrite: 1.17 g (10 mmol)

Toluene: 50 ml

Next, the reaction solution was heated to 110° C. under nitrogen flow, and stirred at this temperature (110° C.) for 3 hours. After the end of the reaction, the resultant substance was washed twice with 50 ml of water. The organic layer was washed with a saturated sodium chloride solution, and then dried over magnesium sulfate. The solution was filtered, and then the filtrate was condensed to thereby obtain a dark brown liquid. The liquid was purified by column chromatography (chloroform/heptane=1:4), and then re-crystallized with chloroform/methanol, thereby obtaining 4.1 g (Yield: 80%) of a yellow crystal E4.

(3) Synthesis of Compound E5

The following reagent and solvent were charged in a 500 ml reactor.

Compound E4: 3.22 g (5 mmol)

Trifluoroacetic acid: 250 ml

Next, the following reagent was put in the reactor under water bathing.

$BF_3$·OEt: 18 ml

Next, the reaction solution was stirred for about 10 minutes, and heated to 50° C. Then, 3.4 g (15 mmol) of DDQ was put in the solution. Next, the reaction solution was stirred for 20 minutes, and then 2.8 g (15 mmol) of ferrocene was put in the solution under 20° C. water bathing. After stirring for about 5 minutes, 200 ml of methanol was added. By filtering a red precipitate formed during this process, a red solid was obtained. Next, the solid was dissolved in toluene, purified by alumina column chromatography (toluene), and then re-crystallized twice with chlorobenzene/methanol, thereby obtaining 2.1 g (Yield: 67%) of a red crystalline exemplary compound E5.

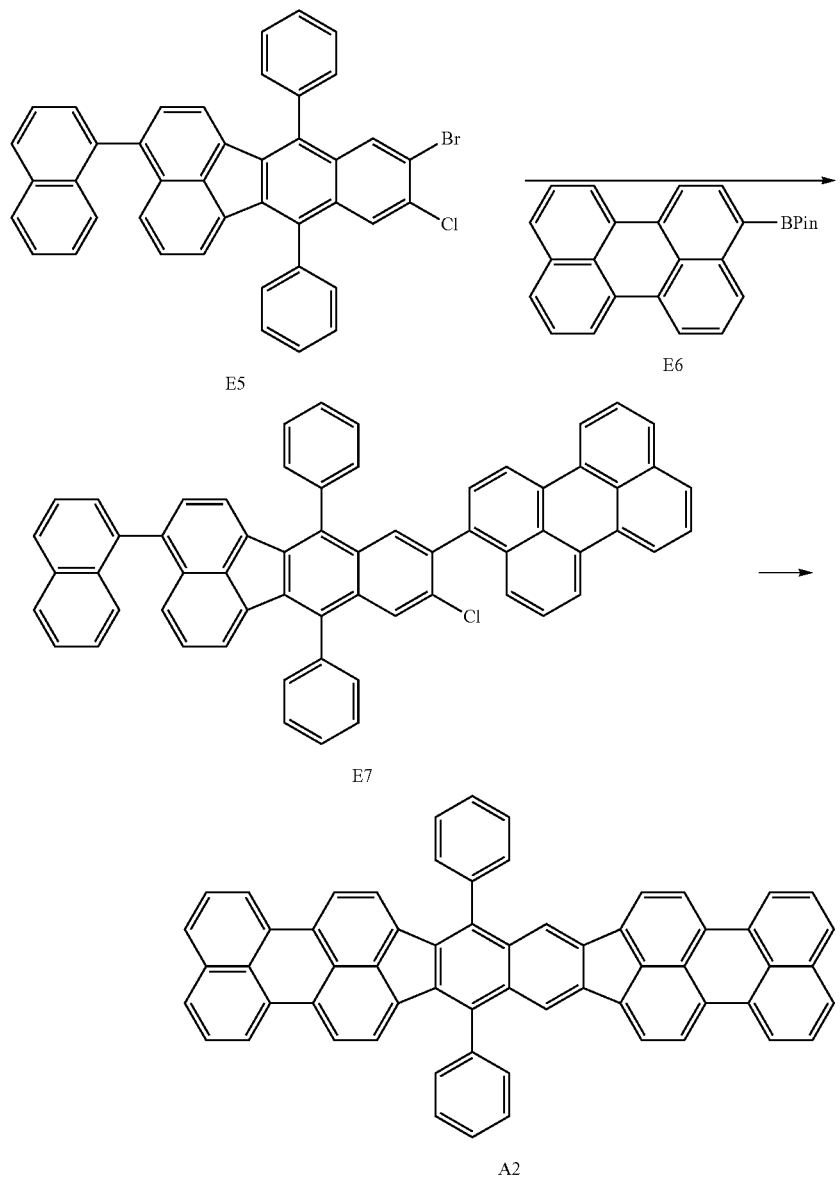

(4) Synthesis of Compound E7

The following reagents and solvent were charged in a 200 ml eggplant flask.
Compound E5: 1.28 g (2 mmol)
Compound E6: 0.52 g (2.1 mmol)
Pd(PPh$_3$)$_4$: 0.04 g
Toluene: 20 ml
Ethanol: 10 ml
2 M aqueous sodium carbonate solution: 20 ml Next, the reaction solution was heated to 80° C. under nitrogen flow, and stirred at this temperature (80° C.) for 8 hours. After the end of the reaction, ethanol was added to precipitate crystals, the crystals were filtered off, and then the crystals were successively washed with water, ethanol, and heptane. Next, the obtained crystals were dissolved in toluene by heating, purified by column chromatography (toluene/heptane=1:2), and then re-crystallized with chloroform/methanol, thereby obtaining 1.42 g (Yield: 87%) of a red compound E7.

(5) Synthesis of Exemplary Compound A2

The following reagents and solvent were charged in a 20 ml eggplant flask.
Compound E7: 815 mg (1 mmol)
Pd(dba)$_2$: 238 mg
P(Cy)$_3$(tricyclohexylphosphine): 280 mg
DBU (diazabicyclo undecene): 0.15 ml
DMF: 5 ml Next, the reaction solution was heated to 145° C. under nitrogen flow, and stirred at this temperature (145° C.) for 6 hours. After the end of the reaction, ethanol was added to precipitate crystals, the crystals were filtered off, and then the crystals were successively washed with water, ethanol, and heptane. Next, the obtained purple crystals were dissolved in toluene by heating, the hot solution was filtered, and then re-crystallization with chloroform/methanol was performed, thereby obtaining 0.62 g (Yield: 80%) of a purple exemplary compound A2.

The purity of this compound was confirmed to be 99% or more as evaluated by HPLC.

With respect to the emission spectrum in the toluene solution in $1\times10^{-5}$ mol/L of the exemplary compound A3, the photoluminescence at an excitation wavelength of 500 nm was measured using F-4500 manufactured by Hitachi. As a result, a spectrum having the maximum intensity at 590 nm was obtained.

The exemplary compound A2 had a low solubility in a solvent and the identification by NMR was difficult to perform. Therefore, the mass spectrometry was performed using MALDI-TOF-MS (Autoflex LRF manufactured by Bruker).

[MALDI-TOF-MS]

Actual measurement value: m/z=776.11, Calculated value: $C_{62}H_{32}$=776.25

Example 2

Synthesis of Exemplary Compound A3

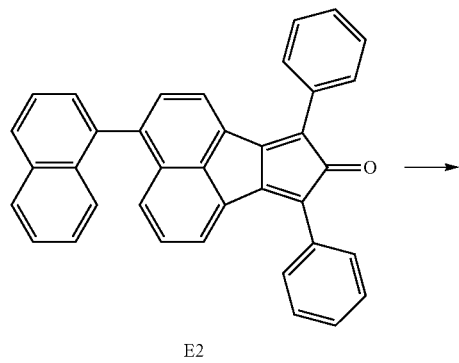

E2

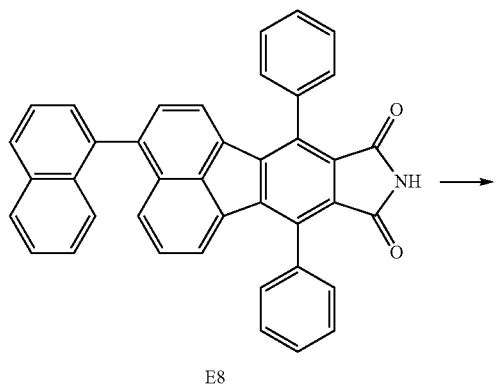

E8

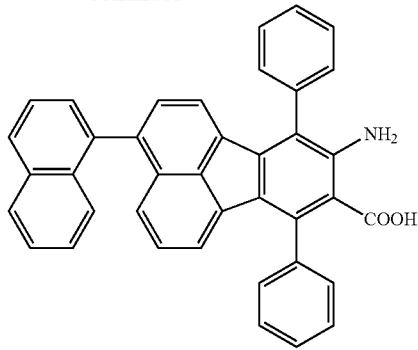

E9

(1) Synthesis of Compound E8

The following reagents and solvent were charged in a 300 ml eggplant flask.

Compound E2: 4.35 g (10 mmol)

Maleimide: 1.72 g (11 mmol)

Bromobenzene: 100 ml

Next, the reaction solution was heated to 130° C. under nitrogen flow, and stirred at this temperature (130° C.) for 6 hours. After the end of the reaction, 50 ml of a saturated aqueous sodium thiosulfate solution was added to separate the liquid. The aqueous layer was extracted 3 times with chloroform, and thereafter the solvent was distilled off with the organic layer. Next, the obtained crystals were dissolved in toluene by heating, purified by column chromatography (chloroform/heptane=2:1), and then re-crystallized with chloroform/methanol, thereby obtaining 4.1 g (Yield: 75%) of a yellow compound E8.

(2) Synthesis of Compound E9

The following reagents and solvent were charged in a 500 ml eggplant flask.

Compound E8: 3.84 g (7 mmol)

0.5 M aqueous sodium hydroxide solution: 3.5 ml

10% aqueous sodium hypochlorite solution: 17.5 ml

Methanol: 350 ml

Next, immediately after charging, the reaction solution was rapidly heated to 80° C. under nitrogen flow immediately, and then the solution was stirred at this temperature (80° C.) for 10 minutes. After the end of the reaction, the resultant solution was ice-cooled, and then supplied in diluted hydrochloric acid. The aqueous layer was extracted 3 times with 300 ml of chloroform, and then the solvent was distilled off with the organic layer. Next, the obtained crystals were mixed with 200 ml of propanol, 5 g of KOH was added, and then the mixture was stirred at 100° C. for 48 hours. After cooling, the resultant mixture was put in water, and then the pH was set to 6 from 5 using hydrochloric acid. The aqueous layer was extracted 3 times with 300 ml of chloroform, and then the solvent was distilled off with the organic layer. Next, the obtained crystals were dissolved in toluene by heating, purified by column chromatography (chloroform/heptane=3:1), and then re-crystallized with chloroform/methanol, thereby obtaining 2.3 g (Yield: 60%) of a yellow compound E9.

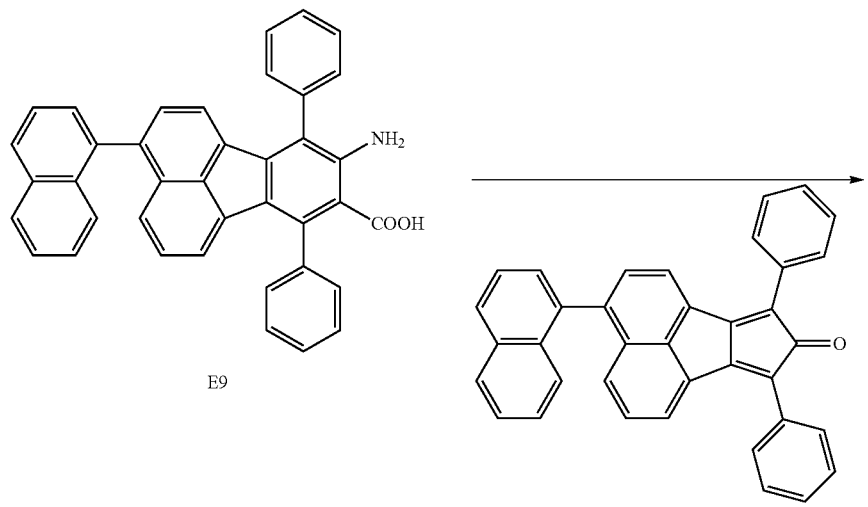

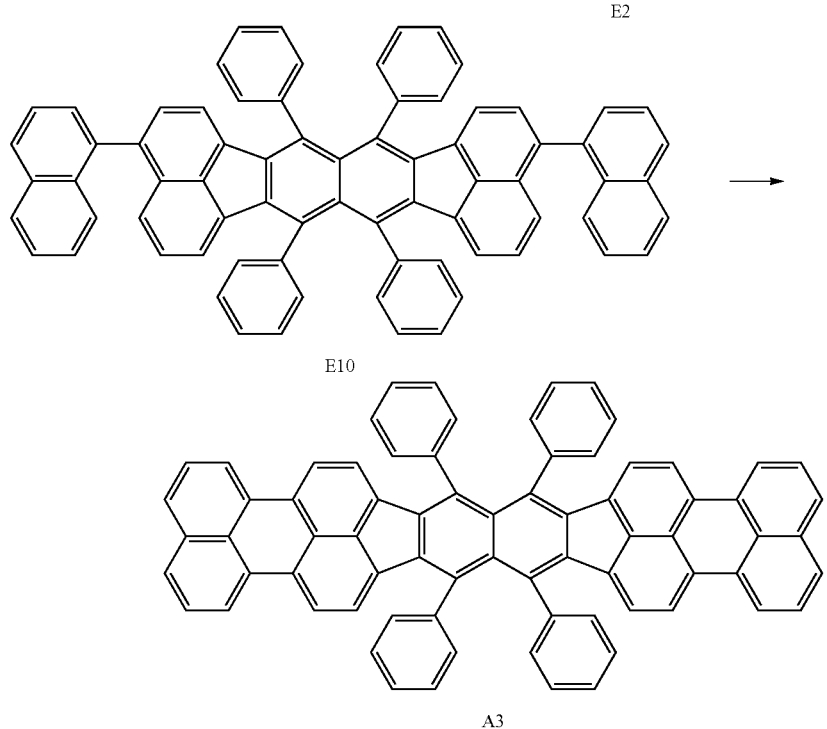

(3) Synthesis of Compound E10

The following reagents and solvent were charged in a 100 ml eggplant flask.
Compound E9: 2.69 g (5 mmol)
Compound E2: 2.41 g (5 mmol)
Isoamyl nitrite: 0.70 g (6 mmol)
Toluene: 30 ml Next, the reaction solution was heated to 110° C. under nitrogen flow, and stirred at this temperature (110° C.) for 3 hours. After the end of the reaction, washing with 30 ml of water was performed twice. The obtained organic layer was washed with a saturated aqueous sodium chloride solution, and then dried over magnesium sulfate. Thereafter, this solution was filtered, and then the filtrate was condensed to thereby obtain a dark brown liquid. The liquid was purified by column chromatography (chloroform/heptane=1:4), and then re-crystallized with chloroform/methanol to thereby obtain 3.9 g (Yield: 83%) of a yellow crystal E10.

(4) Synthesis of Compound A3

The following reagent and solvent were charged in a 500 ml reactor.
Compound E10: 3.73 g (4 mmol)
Trifluoroacetic acid: 200 ml Next, the following reagent was put in the reactor under water bathing.
BF$_3$.OEt: 15 ml Next, the reaction solution was stirred for about 10 minutes, and then 2.7 g (12 mmol) of DDQ was put in the solution under ice bathing. Next, the reaction solution was stirred for 20 minutes, and then 2.2 g (12 mmol) of ferrocene was put in the solution. After stirring for about 5 minutes, 200 ml of methanol was added. By filtering a red precipitate formed during this process, a red solid was obtained. Next, the solid was dissolved in toluene, purified by silica gel chromatography (toluene), and then condensed to thereby obtain red crystals. The red crystals were dispersed in 200 ml of trifluoroacetic acid. Next, the following reagent was put in the reactor under water bathing.

BF$_3$.OEt: 15 ml

Next, the reaction solution was stirred for about 10 minutes, heated to 50° C., and then 2.7 g (12 mmol) of DDQ was put in the solution. Next, the reaction solution was stirred for 20 minutes, and then 2.2 g (12 mmol) of ferrocene was put in the solution under 20° C. water bathing. After stirring for about 5 minutes, 200 ml of methanol was added. By filtering a red precipitate formed during this process, a red solid was obtained. Next, the solid was dissolved in toluene, purified by silica gel chromatography (toluene/heptane=1:2), and then re-crystallized with chloroform/methanol, thereby obtaining 0.37 g (Yield: 10%) of a purple exemplary compound A3.

The purity of the obtained compound was confirmed to be 99.5% or more as evaluated by HPLC.

The emission spectrum in the toluene solution (Concentration: 1×10$^{-5}$ mol/L) of the exemplary compound A3 was measured in the same manner as in Example 1. As a result, a spectrum having the maximum intensity at 598 nm was obtained.

The mass spectrometry was performed using MALDI-TOF-MS (Autoflex LRF manufactured by Bruker).

[MALDI-TOF-MS]

Actual measurement value: m/z=928.14, Calculated value: $C_{74}H_{40}$=928.31

Example 3

Synthesis of Exemplary Compound A4

An exemplary compound A4 was obtained in the same manner as in Example 1, except using the compound E11 shown below in place of the compound E1 in Example 1(1).

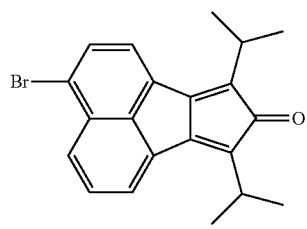

E11

The purity of the obtained compound was confirmed to be 99% or more as evaluated by HPLC.

The emission spectrum in the toluene solution (Concentration: 1×10$^{-5}$ mol/L) of the exemplary compound A4 was measured in the same manner as in Example 1. As a result, a spectrum having the maximum intensity at 593 nm was obtained.

The mass spectrometry was performed using MALDI-TOF-MS (Autoflex LRF manufactured by Bruker).

[MALDI-TOF-MS]

Actual measurement value: m/z=708.54, Calculated value: $C_{56}H_{36}$=708.28

Example 4

Synthesis of Exemplary Compound A6

An exemplary compound A6 was obtained in the same manner as in Example 1, except using the compound E12 shown below in place of the compound E1 in Example 1(1).

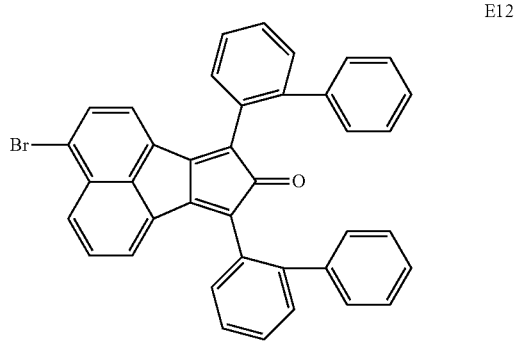 [SMILES: O=C1C(c2ccccc2-c2ccccc2)=C2C(=C1c1ccccc1-c1ccccc1)c1ccc(Br)c3cccc2c13]

E12

The purity of the obtained compound was confirmed to be 99% or more as evaluated by HPLC.

The emission spectrum in the toluene solution (Concentration: 1×10$^{-5}$ mol/L) of the exemplary compound A6 was measured in the same manner as in Example 1. As a result, a spectrum having the maximum intensity at 592 nm was obtained.

The mass spectrometry was performed using MALDI-TOF-MS (Autoflex LRF manufactured by Bruker).

[MALDI-TOF-MS]

Actual measurement value: m/z=928.02, Calculated value: $C_{74}H_{40}$=928.31

Example 5

Synthesis of Exemplary Compound A7

An exemplary compound A7 was obtained in the same manner as in Example 1, except using the compound E13 shown below in place of the compound E1 in Example 1(1).

81 82

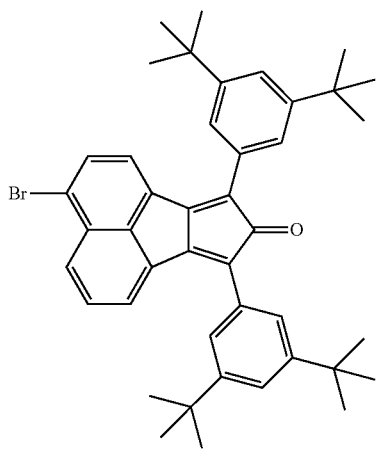

E13

The purity of the obtained compound was confirmed to be 99% or more as evaluated by HPLC.

The emission spectrum in the toluene solution (Concentration: $1\times10^{-5}$ mol/L) of the exemplary compound A7 was measured in the same manner as in Example 1. As a result, a spectrum having the maximum intensity at 592 nm was obtained.

The mass spectrometry was performed using MALDI-TOF-MS (Autoflex LRF manufactured by Bruker).

[MALDI-TOF-MS]

Actual measurement value: m/z=1000.44, Calculated value: Composition of $C_{78}H_{64}$=1000.50

Example 6

Synthesis of Exemplary Compound A13

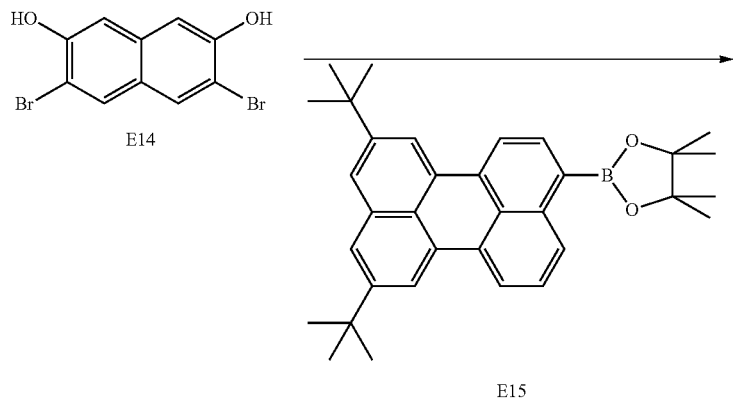

E14

E15

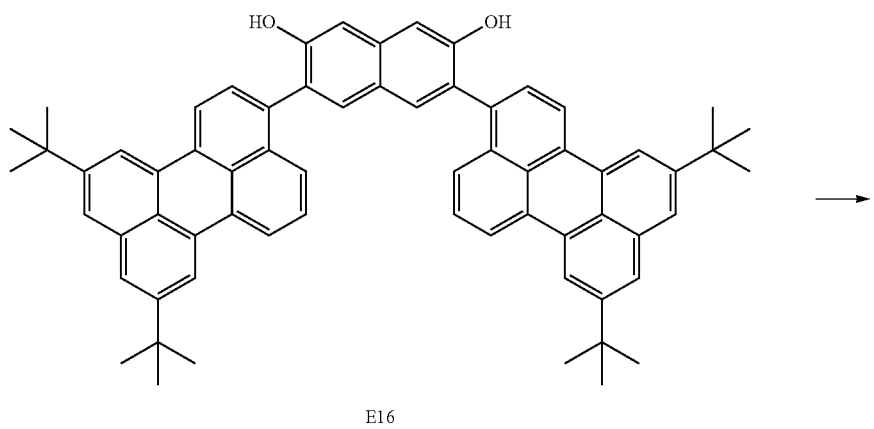

E16

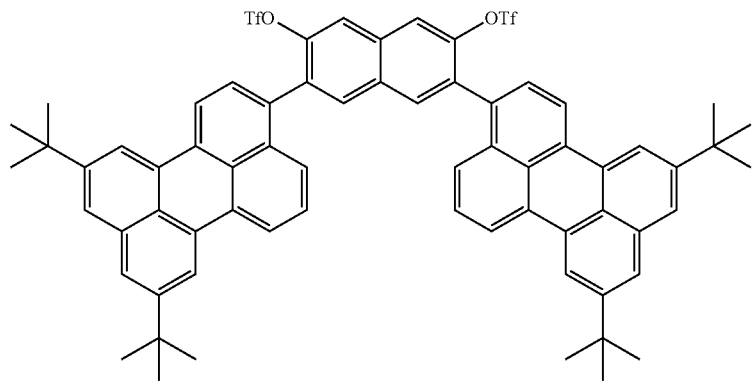

E17

(1) Synthesis of Compound E16

The following reagents and solvent were charged in a 200 ml eggplant flask.
Compound E14: 3.18 g (10 mmol)
Compound E15: 10.3 g (21 mmol)
Pd(PPh₃)₄: 0.4 g
DME: 200 ml
Sodium carbonate: 8.4 g Next, the reaction solution was heated to 80° C. under nitrogen flow, and stirred at this temperature (80° C.) for 8 hours. After the end of the reaction, ethanol was added to precipitate crystals, the crystals were filtered off, and then the crystals were dispersed and washed with heptane. Next, the obtained crystals were dissolved in toluene by heating, purified by column chromatography (toluene/heptane=2:1), and then re-crystallized with chloroform/heptane, thereby obtaining 6.2 g (Yield: 70%) of a compound E16.

(2) Synthesis of Compound E17

The following reagents and solvent were charged in a 300 ml eggplant flask.
Compound E16: 4.43 g (5.0 mmol)
Pyridine: 1.58 g (20.0 mmol)
Dehydrated dichloromethane: 200 mL The reaction solution was cooled to 0° C. under nitrogen while stirring. Then, a solution obtained by diluting 2.2 mL (13 mmol) of trifluoromethanesulfonic anhydride with 20 mL of dichloromethane was added dropwise from a dropping funnel over 20 minutes to be added to the reaction solution. After the end of the dropwise addition, the solution was further continuously stirred at 0° C. for 1 hour, and then water was added to stop the reaction. Then, chloroform was added to the reaction solution, an orange insoluble substance was removed by filtration, the filtrate was washed with water, dried over sodium sulfate, and condensed to thereby obtain a crude product. Next, the crude product was purified by silica gel column chromatography (Developing solvent: heptane/toluene=1/1) to thereby obtain 3.0 g (Yield: 52%) of a compound E16.

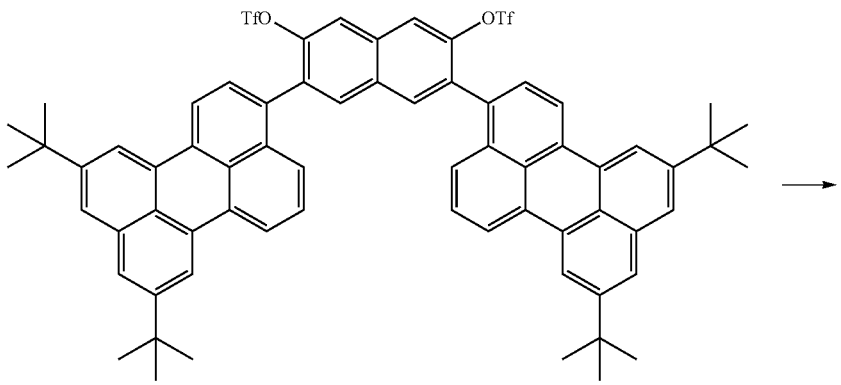

E17

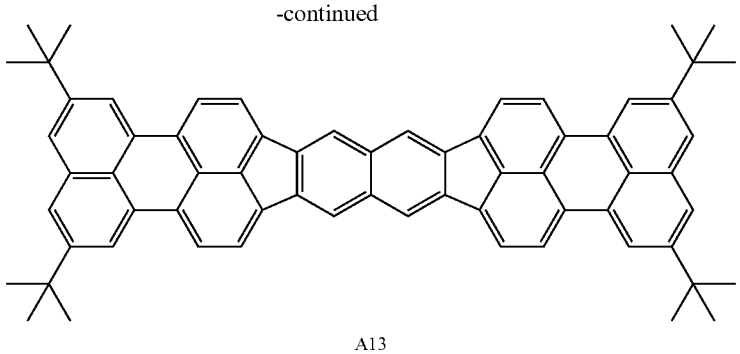

A13

(3) Synthesis of Exemplary Compound A13

The following reagents and solvent were charged in a 20 ml eggplant flask.
Compound E17: 1.15 g (1.0 mmol)
Pd(dba)$_2$: 238 mg
P(Cy)$_3$(tricyclohexylphosphine): 280 mg
DBU (diazabicycloundecene): 0.15 ml
DMF: 5 ml
Triethyl orthoformate: 0.1 ml
Sodium carbonate: 1 g The reaction solution was heated to 145° C. under nitrogen flow, and stirred at this temperature (145° C.) for 6 hours. After the end of the reaction, ethanol was added to precipitate crystals, the crystals were filtered off, and then the crystals were successively washed with water, ethanol, and heptane. Next, the obtained crude product was purified by silica gel chromatography (Developing solvent: heptane/toluene=1/1), and then re-crystallized with toluene/methanol, thereby obtaining 0.18 g (Yield: 21%) of a purple exemplary compound A13.

Further, the mass spectrometry was performed using MALDI-TOF-MS (Autoflex LRF manufactured by Bruker).
[MALDI-TOF-MS]
Actual measurement value: m/z=848.03, Calculated value: $C_{66}H_{56}$=848.44

Example 7

Synthesis of Exemplary Compound A16

An exemplary compound A16 was obtained in the same manner as in Example 1, except using the compound E18 shown below in place of the compound E15 in Example 6(1).

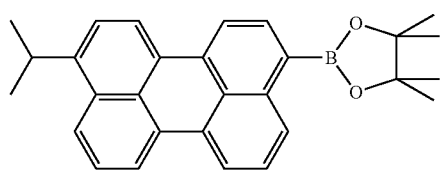

E18

The purity of the obtained compound was confirmed to be 99% or more as evaluated by HPLC.

The emission spectrum in the toluene solution (Concentration: $1\times10^{-5}$ mol/L) of the exemplary compound A16 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=708.65, Calculated value: $C_{56}H_{36}$=708.28

Example 8

Synthesis of Exemplary Compound A18

An exemplary compound A18 was obtained in the same manner as in Example 1, except using the compound E19 shown below in place of the compound E15 in Example 6(1).

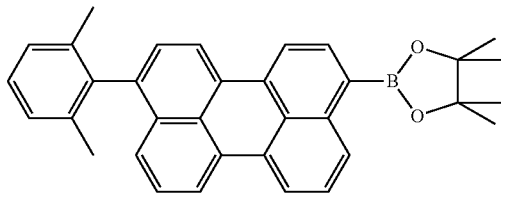

E19

The purity of the obtained compound was confirmed to be 99% or more as evaluated by HPLC.

The emission spectrum in the toluene solution (Concentration: $1\times10^{-5}$ mol/L) of the exemplary compound A18 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=832.55, Calculated value: $C_{66}H_{40}$=832.31

Example 9

Synthesis of Exemplary Compound A19

A compound E22 was synthesized using the compound E20 shown below in place of the compound E5 and the compound E21 shown below in place of the compound E6 in Example 1(4).

87          88
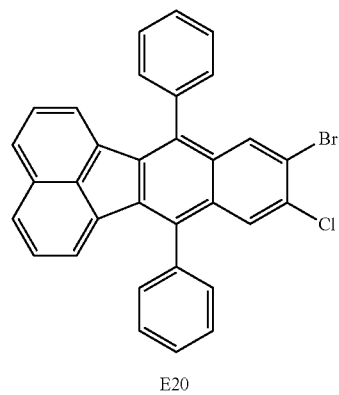 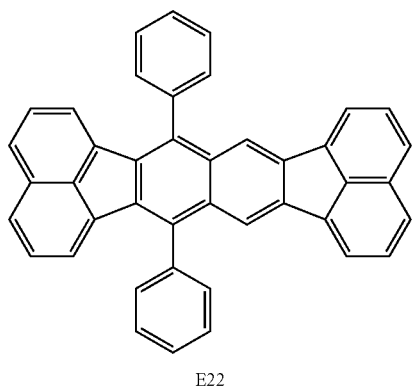
E20          E21          E22
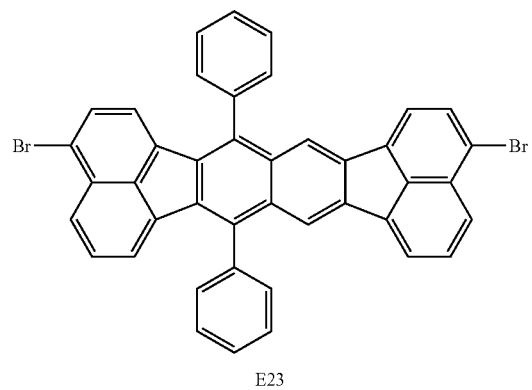 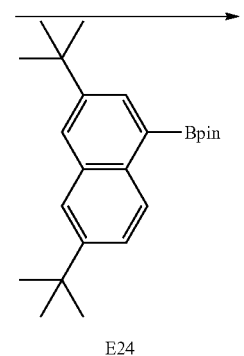
E23          E24
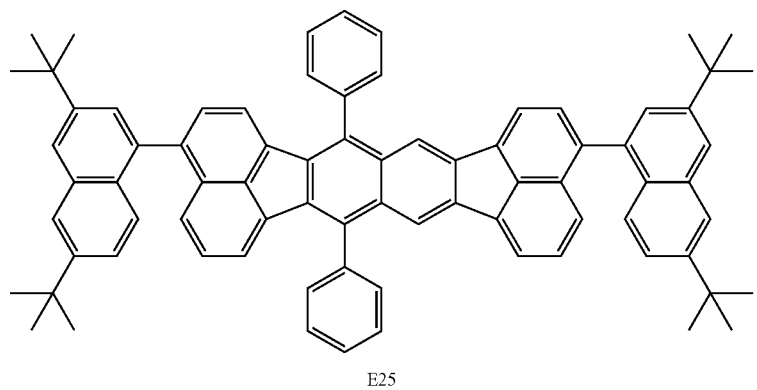
E25
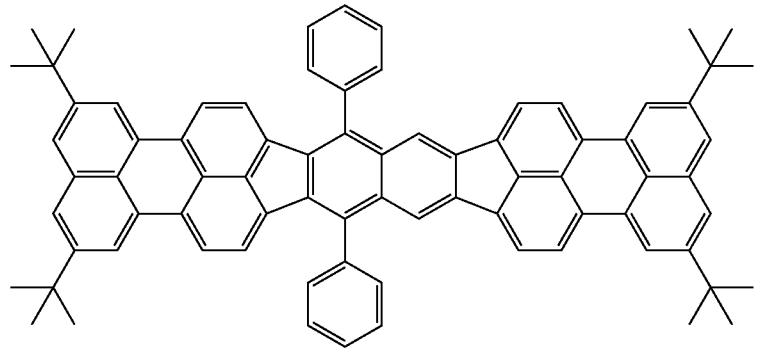
A19

The following synthesis is further performed.

(1) Synthesis of Compound E23

The following reagents and solvent were charged in a 500 ml eggplant flask.
Compound E22: 10.6 g (20 mmol)
Bromine: 3.14 g (20 mmol)
Methylene chloride: 300 ml Next, the reaction solution was stirred at room temperature for 1 hour. After the end of the reaction, ethanol was added to precipitate crystals, the crystals were filtered off, the crystals were washed with heptane, and then the crystals were collected by filtration, thereby obtaining 15.4 g (Yield: 89%) of a compound E23.

(2) Synthesis of Compound E25

The following reagents and solvent were charged in a 500 ml eggplant flask.
Compound E23: 6.84 g (10 mmol)
Compound E24: 5.03 g (21 mmol)
Pd(PPh$_3$)$_4$: 0.4 g
Toluene: 100 ml
Ethanol: 50 ml
2 M aqueous cesium carbonate solution: 100 ml Next, the reaction solution was heated to 80° C. under nitrogen flow, and stirred at this temperature (80° C.) for 8 hours. After the end of the reaction, ethanol was added to precipitate crystals, the crystals were filtered off, and then the crystals were successively washed with water, ethanol, and heptane. Next, the obtained crystals were dissolved in toluene by heating, purified by column chromatography (toluene/heptane=1:1), and then re-crystallized with toluene/methanol, thereby obtaining 7.1 g (Yield: 71%) of a yellow compound E25.

(3) Synthesis of Compound A19

The following reagent and solvent were charged in a 500 ml reactor.
Compound E25: 5.02 g (5 mmol)
Trifluoroacetic acid: 220 ml Next, the following reagent was put in the reactor under water bathing.
BF$_3$.OEt: 18 ml Next, the reaction solution was stirred for about 10 minutes, and then, 3.4 g (15 mmol) of DDQ was put in the solution under ice bathing. Next, the reaction solution was stirred for 20 minutes, and then 2.8 g (15 mmol) of ferrocene was put in the solution. After stirring for about 5 minutes, 200 ml of methanol was added. By filtering a red precipitate formed during this process, a red solid was obtained. Next, the solid was dissolved in toluene, purified by silica gel column chromatography (toluene), and then condensed to thereby obtain red crystals. Then, the red crystals were dispersed in 200 ml of trifluoroacetic acid. Next, the following reagent was put in the reactor under water bathing.
BF$_3$.OEt: 18 ml Next, the reaction solution was stirred for about 10 minutes, and heated to 50° C. Then, 3.4 g (15 mmol) of DDQ was put in the solution. Next, the reaction solution was stirred for 20 minutes, and then 2.8 g (15 mmol) of ferrocene was put in under 20° C. water bathing. After stirring for about 5 minutes, 200 ml of methanol was added. By filtering a red precipitate formed during this process, a red solid was obtained. Next, the solid was dissolved in toluene, purified by silica gel chromatography (toluene/heptane=1:2), and then re-crystallized with chloroform/methanol, thereby obtaining 0.6 g (Yield: 12%) of a purple exemplary compound A19.

The purity of the obtained compound was confirmed to be 99% or more as evaluated by HPLC.

The emission spectrum in the toluene solution (Concentration: 1×10$^{-5}$ mol/L) of the exemplary compound A19 was measured in the same manner as in Example 1. As a result, a spectrum having the maximum intensity at 594 nm was obtained.

The mass spectrometry was performed using MALDI-TOF-MS (Autoflex LRF manufactured by Bruker).
[MALDI-TOF-MS]
Actual measurement value: m/z=1000.03, Calculated value: C$_{78}$H$_{64}$=1000.50

Example 10

Synthesis of Exemplary Compound A21

An exemplary compound A21 was obtained in the same manner as in Example 9, except using the compound E26 shown below in place of the compound E24 in Example 9(1).

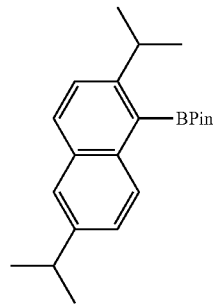

E26

The purity of the obtained compound was confirmed to be 99% or more as evaluated by HPLC.

The emission spectrum in the toluene solution (Concentration: 1×10$^{-5}$ mol/L) of the exemplary compound A21 was measured in the same manner as in Example 1. As a result, a spectrum having the maximum intensity at 590 nm was obtained.

The mass spectrometry was performed using MALDI-TOF-MS (Autoflex LRF manufactured by Bruker).
[MALDI-TOF-MS]
Actual measurement value: m/z=1155.78, Calculated value: C$_{90}$H$_{75}$=1155.59

Example 11

Synthesis of Exemplary Compound A27

An exemplary compound A27 was obtained in the same manner as in Example 1, except using the compound E27 shown below in place of 1-naphthalene boronic acid in Example 1(1) and the compound E28 shown below in place of the compound E6 in Example 1(4).

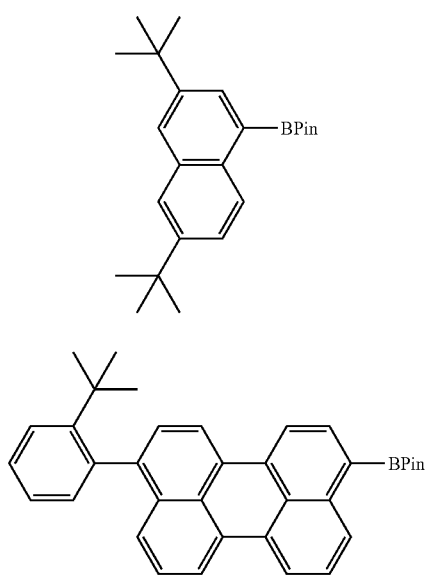

E27

E28

The purity of the obtained compound was confirmed to be 99% or more as evaluated by HPLC.

The emission spectrum in the toluene solution (Concentration: $1\times10^{-5}$ mol/L) of the exemplary compound A27 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1020.87, Calculated value: $C_{80}H_{60}$=1020.47

Example 12

Synthesis of Exemplary Compound A30

An exemplary compound A30 was obtained in the same manner as in Example 1, except using the compound E29 shown below in place of 1-naphthalene boronic acid in Example 1(1) and the compound E30 shown below in place of the compound E6 in Example 1(4).

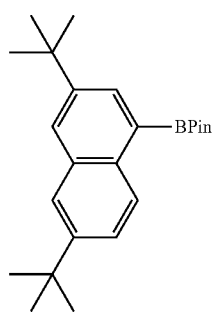

E29

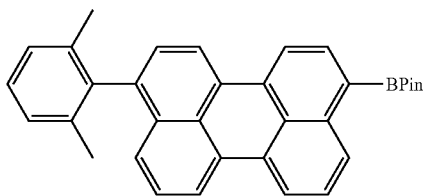

E30

The purity of the obtained compound was confirmed to be 99% or more as evaluated by HPLC.

The emission spectrum in the toluene solution (Concentration: $1\times10^{-5}$ mol/L) of the exemplary compound A30 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=992.11, Calculated value: $C_{78}H_{56}$=992.44

Example 13

Synthesis of Exemplary Compound A31

An exemplary compound A31 was obtained in the same manner as in Example 1, except using the compound E31 shown below in place of 1-naphthalene boronic acid in Example 1(1) and the compound E32 shown below in place of the compound E6 in Example 1(4).

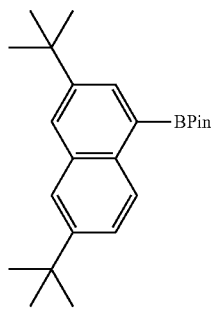

E31

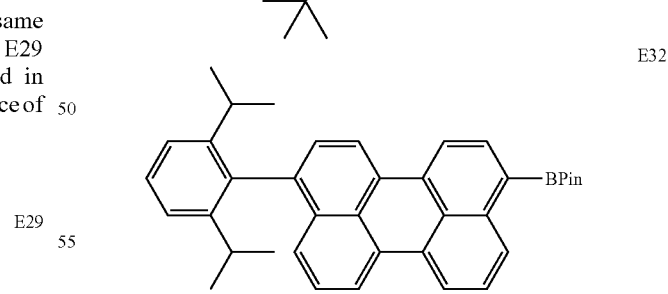

E32

The purity of the obtained compound was confirmed to be 99% or more as evaluated by HPLC as evaluated by HPLC.

The emission spectrum in the toluene solution (Concentration: $1\times10^{-5}$ mol/L) of the exemplary compound A31 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).

[MALDI-TOF-MS]
Actual measurement value: m/z=1048.91, Calculated value: $C_{82}H_{64}$=1048.50

Example 14

Synthesis of Exemplary Compound A33

An exemplary compound A33 was obtained in the same manner as in Example 9, except using the compound E33 shown below in place of the compound E20 in Example 9(1).

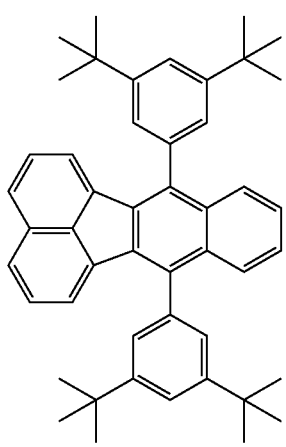

E33

The purity of the obtained compound was confirmed to be 99% or more as evaluated by HPLC.

The emission spectrum in the toluene solution (Concentration: 1×10$^{-5}$ mol/L) of the exemplary compound A33 was measured in the same manner as in Example 1. As a result, a spectrum having the maximum intensity at 593 nm was obtained.

Further, the mass spectrometry was performed using MALDI-TOF-MS (Autoflex LRF manufactured by Bruker).
[MALDI-TOF-MS]
Actual measurement value: m/z=1224.22, Calculated value: $C_{94}H_{96}$=1224.75

Example 15

Synthesis of Exemplary Compound A43

An exemplary compound A43 was obtained in the same manner as in Example 1, except using the compound E34 shown below in place of the compound E20 in Example 9(1) and the compound E35 shown below in place of the compound E24 in Example 9(2).

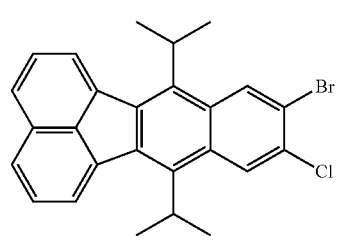

E34

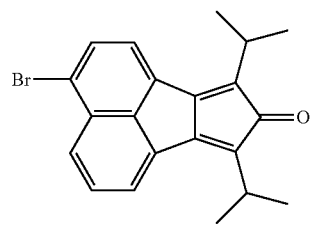

E35

The purity of the obtained compound was confirmed to be 99% or more as evaluated by HPLC.

The emission spectrum in the toluene solution (Concentration: 1×10$^{-5}$ mol/L) of the exemplary compound A43 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=792.88, Calculated value: $C_{62}H_{48}$=792.38

Example 16

Synthesis of Exemplary Compound A46

An exemplary compound A46 was obtained in the same manner as in Example 1, except using the compound E36 shown below in place of the compound E1 and the compound E37 shown below in place of 1-naphthalene boronic acid in Example 1(1) and the compound E38 shown below in place of the compound E6 in Example 1(4).

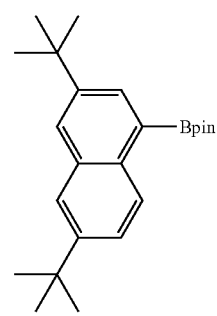

E36

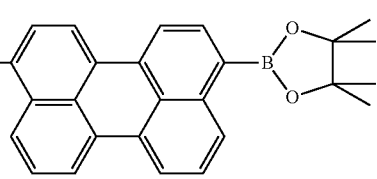

E37

E38

The purity of the obtained compound was confirmed to be 99% or more as evaluated by HPLC.

The emission spectrum in the toluene solution (Concentration: 1×10$^{-5}$ mol/L) of the exemplary compound A46 was measured in the same manner as in Example 1. As a result, a spectrum having the maximum intensity at 593 nm was obtained.

Further, the mass spectrometry was performed using MALDI-TOF-MS (Autoflex LRF manufactured by Bruker).
[MALDI-TOF-MS]
Actual measurement value: m/z=862.22, Calculated value: $C_{62}H_{58}$=862.45

Example 17

Synthesis of Exemplary Compound A47

An exemplary compound A47 was obtained in the same manner as in Example 1, except using the compound E39 shown below in place of the compound E1 and the compound E40 shown below in place of 1-naphthalene boronic acid in Example 1(1) and the compound E41 shown below in place of the compound E6 in Example 1(4).

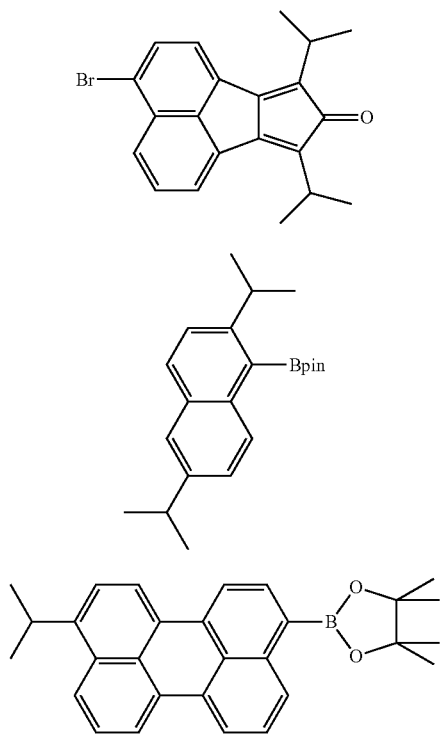

The purity of the obtained compound was confirmed to be 99% or more as evaluated by HPLC.

The emission spectrum in the toluene solution (Concentration: 1×10$^{-5}$ mol/L) of the exemplary compound A47 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=834.88, Calculated value: $C_{65}H_{54}$=834.42

Example 18

Synthesis of Exemplary Compound A50

An exemplary compound A50 was obtained in the same manner as in Example 1, except using the compound E42 shown below in place of the compound E1 and the compound E43 shown below in place of 1-naphthalene boronic acid in Example 1(1) and the compound E44 shown below in place of the compound E6 in Example 1(4).

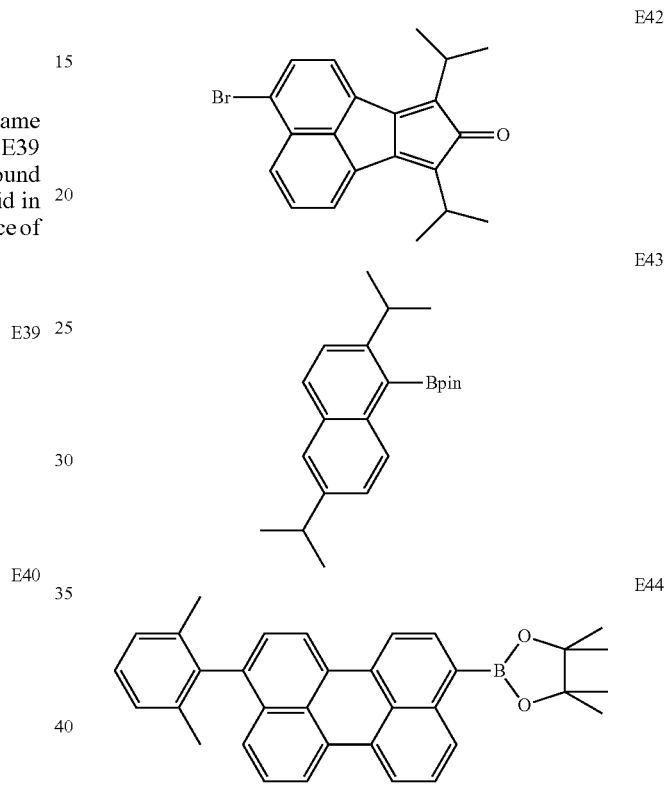

The purity of the obtained compound was confirmed to be 99% or more as evaluated by HPLC.

The emission spectrum in the toluene solution (Concentration: 1×10$^{-5}$ mol/L) of the exemplary compound A50 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=896.02, Calculated value: $C_{70}H_{56}$=896.44

Example 19

Synthesis of Exemplary Compound A52

An exemplary compound A52 was obtained in the same manner as in Example 1, except using the compound E45 shown below in place of the compound E1 and the compound E46 shown below in place of 1-naphthalene boronic acid in Example 1(1) and the compound E47 shown below in place of the compound E6 in Example 1(4).

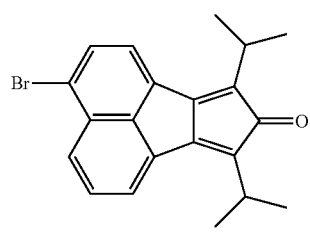

E45

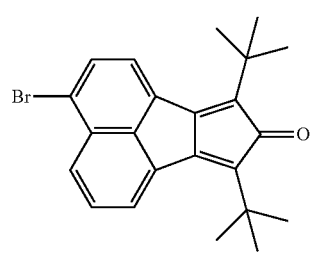

E48

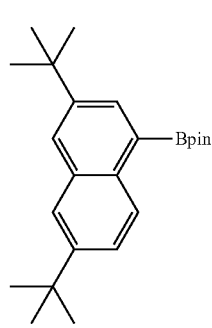

E46

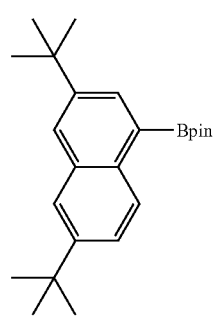

E49

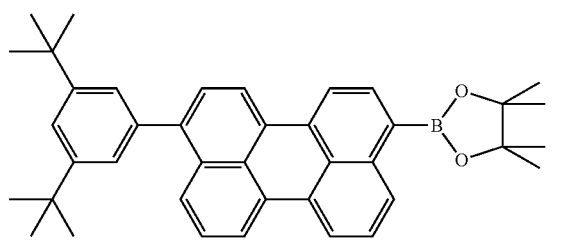

E47

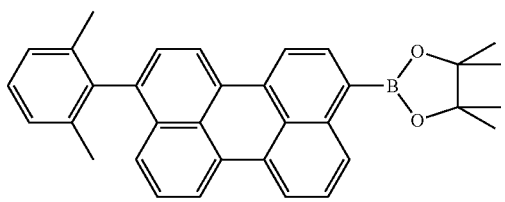

E50

The purity of the obtained compound was confirmed to be 99% or more as evaluated by HPLC.

The emission spectrum in the toluene solution (Concentration: $1 \times 10^{-5}$ mol/L) of the exemplary compound A52 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1008.26, Calculated value: $C_{78}H_{72}$=1008.56

Example 20

Synthesis of Exemplary Compound A55

An exemplary compound A55 was obtained in the same manner as in Example 1, except using the compound E48 shown below in place of the compound E1 and the compound E49 shown below in place of 1-naphthalene boronic acid in Example 1(1) and the compound E50 shown below in place of the compound E6 in Example 1(4).

The purity of the obtained compound was confirmed to be 99% or more as evaluated by HPLC.

The emission spectrum in the toluene solution (Concentration: $1 \times 10^{-5}$ mol/L) of the exemplary compound A55 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=952.18, Calculated value: $C_{74}H_{64}$=952.50

Example 21

Synthesis of Exemplary Compound A56

An exemplary compound A56 was obtained in the same manner as in Example 2, except using the compound E51 shown below in place of the compound E2 in Example 2(1).

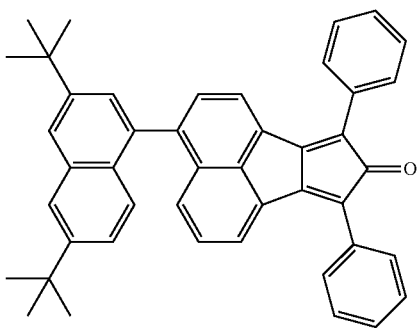

E51

The purity of the obtained compound was confirmed to be 99% or more as evaluated by HPLC.

The emission spectrum in the toluene solution (Concentration: $1\times10^{-5}$ mol/L) of the exemplary compound A56 was measured in the same manner as in Example 1. As a result, a spectrum having the maximum intensity at 599 nm was obtained.

Further, the mass spectrometry was performed using MALDI-TOF-MS (Autoflex LRF manufactured by Bruker).
[MALDI-TOF-MS]
Actual measurement value: m/z=1152.23, Calculated value: $C_{90}H_{72}$=1152.56

Example 22

Synthesis of Exemplary Compound A70

An exemplary compound A70 was obtained in the same manner as in Example 2, except using the compound E52 shown below in place of the compound E2 in Example 2(1).

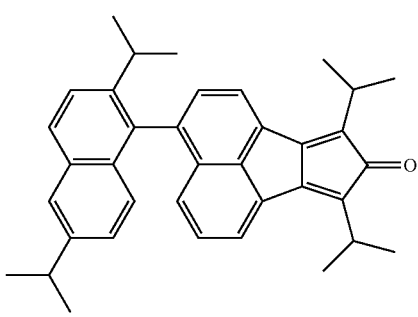

E52

The purity of the obtained compound was confirmed to be 99% or more as evaluated by HPLC.

The emission spectrum in the toluene solution (Concentration: $1\times10^{-5}$ mol/L) of the exemplary compound A70 was measured in the same manner as in Example 1. As a result, a spectrum having the maximum intensity at 600 nm was obtained.

Further, the mass spectrometry was performed using MALDI-TOF-MS (Autoflex LRF manufactured by Bruker).
[MALDI-TOF-MS]
Actual measurement value: m/z=960.55, Calculated value: $C_{74}H_{72}$=960.56

Example 23

Synthesis of Exemplary Compound B6

An exemplary compound B6 was obtained in the same manner as in Example 1, except using the compound E53 shown below in place of the compound E1 and the compound E54 shown below in place of 1-naphthalene boronic acid in Example 1(1) and the compound E55 shown below in place of the compound E6 in Example 1(4).

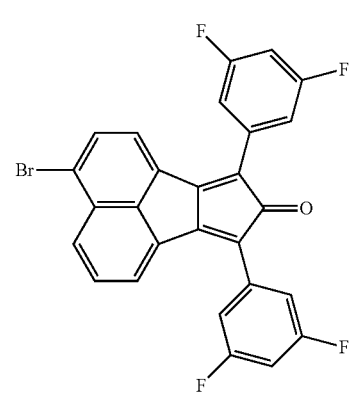

E53

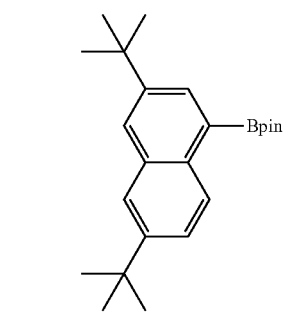

E54

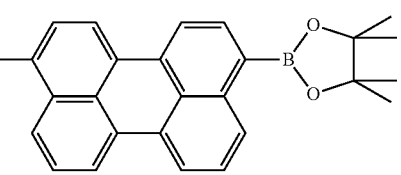

E55

The purity of the obtained compound was confirmed to be 99% or more as evaluated by HPLC.

The emission spectrum in the toluene solution (Concentration: $1\times10^{-5}$ mol/L) of the exemplary compound B6 was measured in the same manner as in Example 1. As a result, a spectrum having the maximum intensity at 593 nm was obtained.

Further, the mass spectrometry was performed using MALDI-TOF-MS (Autoflex LRF manufactured by Bruker).
[MALDI-TOF-MS]
Actual measurement value: m/z=1002.56, Calculated value: $C_{73}H_{60}F_4$=1002.38

Example 24

Synthesis of Exemplary Compound B7

An exemplary compound B7 was obtained in the same manner as in Example 1, except using the compound E56 shown below in place of the compound E1 and the compound E57 shown below in place of 1-naphthalene boronic acid in Example 1(1) and the compound E58 shown below in place of the compound E6 in Example 1(4).

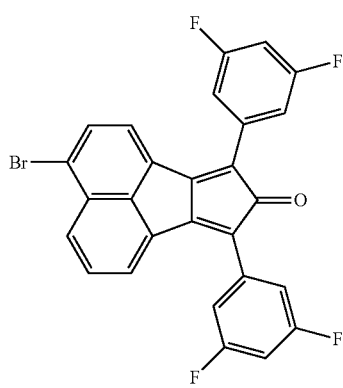

E56

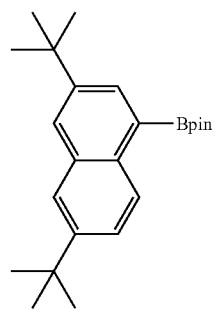

E57

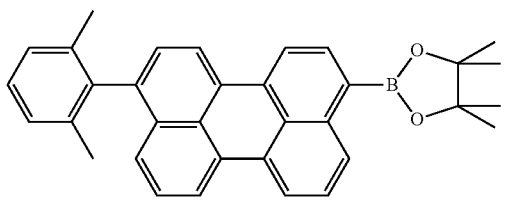

E58

The purity of the obtained compound was confirmed to be 99% or more as evaluated by HPLC.

The emission spectrum in the toluene solution (Concentration: $1\times10^{-5}$ mol/L) of the exemplary compound B7 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1064.33, Calculated value: $C_{78}H_{52}F_4$=1064.40

Example 25

Synthesis of Exemplary Compound B9

An exemplary compound B9 was obtained in the same manner as in Example 1, except using the compound E59 shown below in place of the compound E15 in Example 6(1).

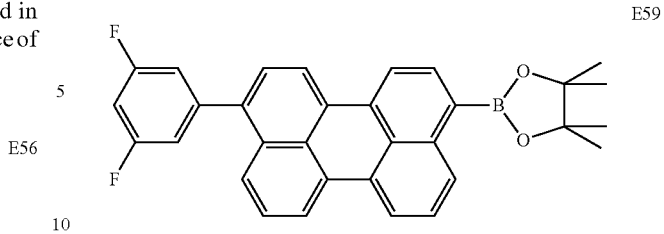

E59

The purity of the obtained compound was confirmed to be 99% or more as evaluated by HPLC.

The emission spectrum in the toluene solution (Concentration: $1\times10^{-5}$ mol/L) of the exemplary compound B9 was measured in the same manner as in Example 1. As a result, a spectrum having the maximum intensity at 594 nm was obtained.

Further, the mass spectrometry was performed using MALDI-TOF-MS (Autoflex LRF manufactured by Bruker).
[MALDI-TOF-MS]
Actual measurement value: m/z=848.88, Calculated value: $C_{62}H_{28}F_4$=848.88

Example 26

Synthesis of Exemplary Compound B12

An exemplary compound B12 was obtained in the same manner as in Example 9, except using the compound E60 shown below in place of the compound E24 in Example 9(1).

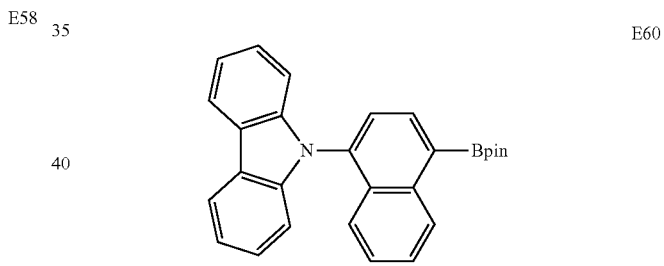

E60

The purity of the obtained compound was confirmed to be 99% or more as evaluated by HPLC.

The emission spectrum in the toluene solution (Concentration: $1\times10^{-5}$ mol/L) of the exemplary compound B12 was measured in the same manner as in Example 1. As a result, a spectrum having the maximum intensity at 602 nm was obtained.

Further, the mass spectrometry was performed using MALDI-TOF-MS (Autoflex LRF manufactured by Bruker).
[MALDI-TOF-MS]
Actual measurement value: m/z=1106.65, Calculated value: $C_{86}H_{46}N_2$=1106.37

Example 27

In this example, an organic light emitting device was produced in which an anode, a hole transporting layer, an electron blocking layer, a light emitting layer, a hole/exciton blocking layer, an electron transporting layer, and a cathode were successively formed on a substrate. Some of the materials used in this example are shown below.

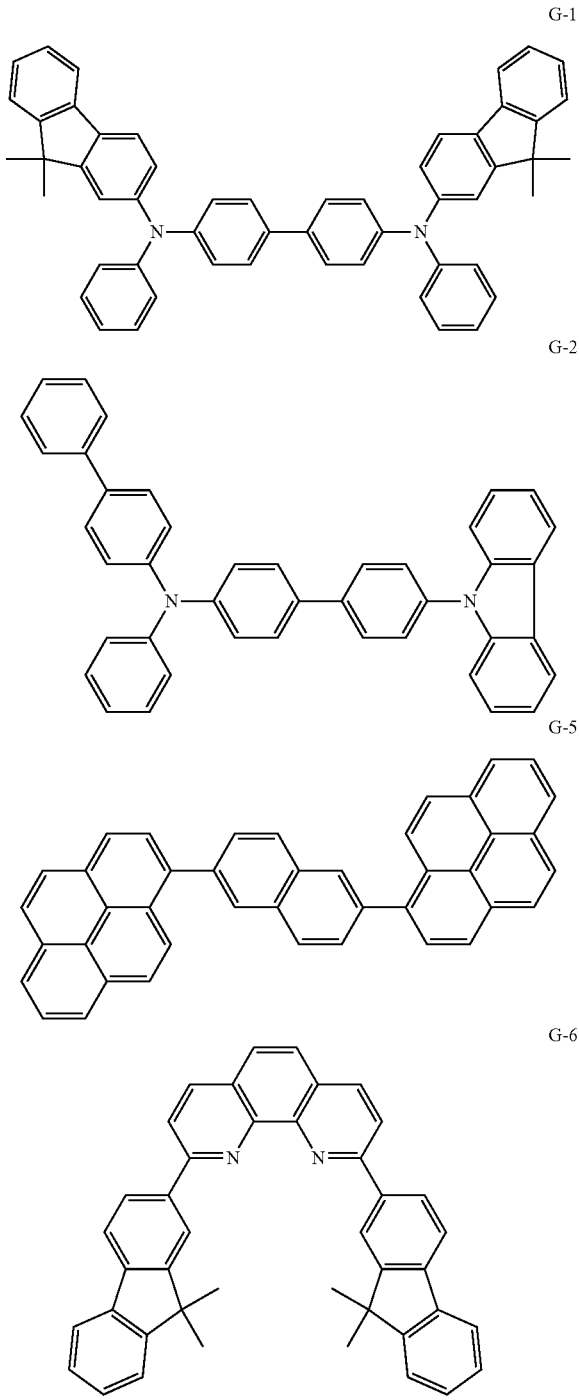

TABLE 3

| | Material | Film thickness (nm) |
|---|---|---|
| Hole transporting layer | G-1 | 30 |
| Electron blocking layer | G-2 | 10 |
| Light emitting layer | G-3 (Host) G-4 (Assist) Exemplary compound A7 (Guest) (G-3:G-4:A7 = 60:39.5:0.5 (Weight ratio)) | 30 |
| Hole blocking layer | G-5 | 10 |
| Electron transporting layer | G-6 | 30 |
| First metal electrode layer | LiF | 1 |
| Second metal electrode layer | Al | 100 |

In this Example, G-3 and G-4 are H6 and H22 shown in Table 2, respectively.

The obtained device was measured and evaluated for the characteristics of the device. Specifically, the current-voltage characteristics were measured with a microammeter 4140B manufactured by Hewlett-Packard Company and the light emission luminosity was measured with BM7 manufactured by TOPCON CORPORATION. The measurements results are shown in Table 4.

Examples 28 to 39

Organic light emitting devices were produced in the same manner as in Example 27, except changing, as appropriate, G-3, G-4, and the guest in Example 27 to the compounds shown in Table 4. The obtained devices were measured and evaluated for the characteristics of the devices in the same manner as in Example 27. The measurement results are shown in Table 4. In Table 4, when the materials of G-3 and G-4 are the same, the materials of the host and the assist are the same and the hosts shown in Table 2 were used.

TABLE 4

| | Guest | G-3 | G-4 | Light emission efficiency (cd/A) | Voltage (V) | Chromaticity (X, Y) |
|---|---|---|---|---|---|---|
| Example 27 | A7 | H6 | H22 | 4.5 | 4.4 | (0.65, 0.36) |
| Example 28 | A13 | H7 | H21 | 3.0 | 4.3 | (0.65, 0.35) |
| Example 29 | A16 | H12 | H23 | 4.5 | 4.5 | (0.65, 0.36) |
| Example 30 | A19 | H19 | H24 | 4.3 | 4.3 | (0.66, 0.36) |
| Example 31 | A30 | H23 | H22 | 3.5 | 4.4 | (0.65, 0.35) |
| Example 32 | A31 | H22 | H24 | 4.6 | 4.2 | (0.65, 0.35) |
| Example 33 | A43 | H12 | H21 | 5.1 | 4.5 | (0.65, 0.36) |
| Example 34 | A47 | H19 | H19 | 4.8 | 4.6 | (0.66, 0.34) |
| Example 35 | A52 | H24 | H21 | 4.3 | 4.2 | (0.66, 0.35) |
| Example 36 | A56 | H20 | H21 | 5.2 | 4.2 | (0.67, 0.33) |
| Example 37 | A70 | H10 | H19 | 3.2 | 4.1 | (0.67, 0.34) |
| Example 38 | B6 | H17 | H22 | 4.9 | 4.6 | (0.65, 0.35) |
| Example 39 | B9 | H6 | H21 | 4.5 | 4.7 | (0.65, 0.36) |

First, ITO was formed into a film, and then subjected to desired patterning processing to thereby form an ITO electrode (anode) on a glass substrate. In this case, the film thickness of the ITO electrode was set to 100 nm. The substrate on which the ITO electrode was formed thus obtained was used as an ITO substrate in the following processes.

Organic compound layers and electrode layers shown in the following Table 3 were successively formed on the ITO substrate. In this case, the electrode area of the electrodes (the metal electrode layers and the cathode) facing each other was set to 3 mm².

Example 40

In this example, an organic light emitting device was produced in which an anode, a hole injecting layer, a hole transporting layer, a light emitting layer, an electron transporting layer, an electron injecting layer, and a cathode were successively formed on a substrate. The organic light emitting device produced in this example has a resonance structure. Some of the materials used in this example are shown below.

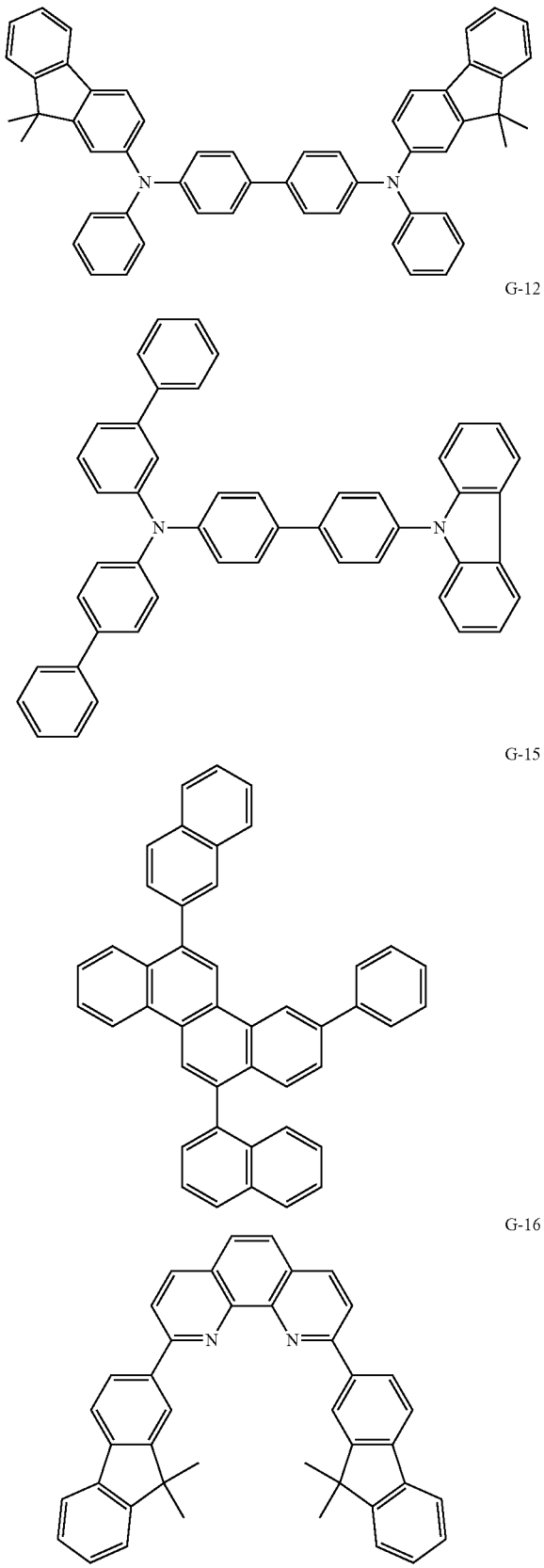

First, an aluminum alloy (AlNd) was formed into a film by a sputtering method to form a reflective anode on a glass substrate (support). In this case, the film thickness of the reflective anode was set to 100 nm. Next, ITO was formed into a film by a sputtering method to form a transparent anode on the reflective anode. In this case, the film thickness of the transparent anode was set to 80 nm. Next, an acrylic element isolation film was formed around the anode with a film thickness of 1.5 μm, and then subjected to desired patterning to thereby provide an opening portion having a radius of 3 mm. Next, the substrate on which the anode was formed was successively ultrasonically cleaned with acetone and isopropyl alcohol (IPA). Next, the substrate was cleaned by boiling with IPA, and then dried. Next, the substrate surface was subjected to UV/ozone cleaning.

Next, vacuum evaporation by resistance heating in a vacuum chamber of $1 \times 10^{-5}$ Pa was performed to successively form the organic compound layers shown in the following Table 5 on the ITO substrate.

TABLE 5

| | Material | Film thickness (nm) |
|---|---|---|
| Hole transporting layer | G-11 | 135 |
| Electron blocking layer | G-12 | 10 |
| Light emitting layer | G-13 (Host) | 30 |
| | G-14 (Assist) | |
| | Exemplary compound A17 (Guest) | |
| | (G-13:G-14:A:17 = 60:39.5:0.5 (Weight ratio)) | |
| Electron transporting layer | G-15 | 10 |
| Electron injecting layer | G-16 | 70 |
| | Li | |
| | (G-16:Li = 80:20 (Weight ratio)) | |

In this Example, G-13 and G-14 are H23 and H23 shown in Table 2, respectively.

Next, ITO was formed into a film by a sputtering method to form a cathode on the electron injecting layer. In this case, the film thickness of the cathode was set to 30 nm. Finally, sealing was performed under a nitrogen atmosphere. Thus, an organic light emitting device was produced.

The obtained device was measured and evaluated for the characteristics of the device. Specifically, the current-voltage characteristics were measured with a microammeter 4140B manufactured by Hewlett-Packard Company and the light emission luminosity was measured with BM7 manufactured by TOPCON CORPORATION. The measurements results are shown in Table 6.

Examples 41 to 47

Organic light emitting devices were produced in the same manner as in Example 42, except changing, as appropriate, G-13, G-14, and the guest in Example 40 to the compounds shown in Table 4. The obtained devices were measured and evaluated for the characteristics of the devices in the same manner as in Example 40. The measurement results are shown in Table 6. In Table 6, when the materials of G-13 and G-14 are the same, the materials of the host and the assist are the same and the hosts shown in Table 2 were used.

TABLE 6

|  | Guest | G-13 | G-14 | Light emission efficiency (cd/A) | Voltage (V) | Chromaticity (X, Y) |
|---|---|---|---|---|---|---|
| Example 40 | A17 | H23 | H23 | 8.5 | 4.5 | (0.67, 0.33) |
| Example 41 | A18 | H19 | H22 | 9.1 | 4.5 | (0.67, 0.33) |
| Example 42 | A21 | H24 | H24 | 7.5 | 4.7 | (0.66, 0.34) |
| Example 43 | A27 | H12 | H19 | 8.5 | 4.3 | (0.67, 0.33) |
| Example 44 | A46 | H18 | H22 | 9.0 | 4.5 | (0.66, 0.34) |
| Example 45 | A50 | H14 | H21 | 9.5 | 4.5 | (0.67, 0.33) |
| Example 46 | A55 | H20 | H20 | 6.9 | 4.9 | (0.67, 0.33) |
| Example 47 | B9 | H22 | H22 | 7.0 | 5.0 | (0.65, 0.35) |

Example 48

In this Example, an organic light emitting device was produced in which an anode, a hole transporting layer, a first light emitting layer, a second light emitting layer, a hole/exciton blocking layer, an electron transporting layer, and a cathode were successively formed on a substrate and in which the first light emitting layer emits red light and white light is emitted by mixing the light with light emitted from the second light emitting layer. The organic light emitting device of this example is an aspect in which a plurality of light emitting layers are provided. Some of the materials used in this example are shown below.

G-21

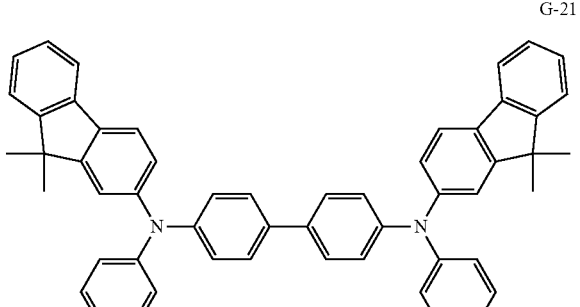

G-22

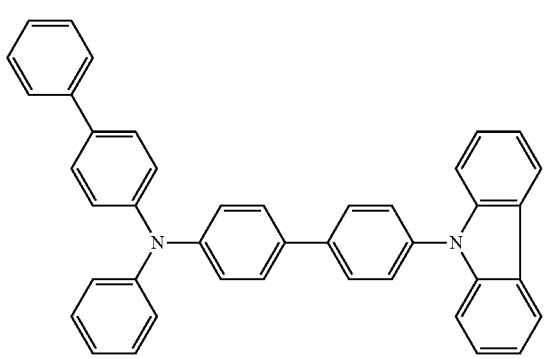

G-24

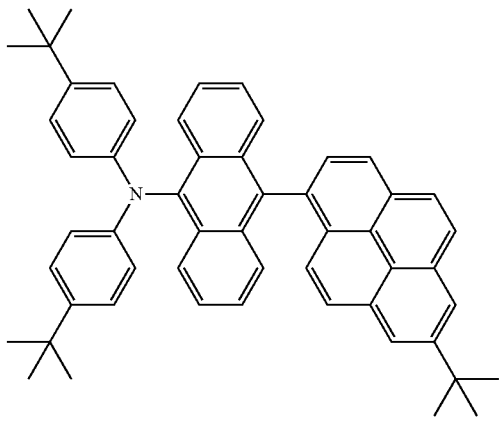

G-27

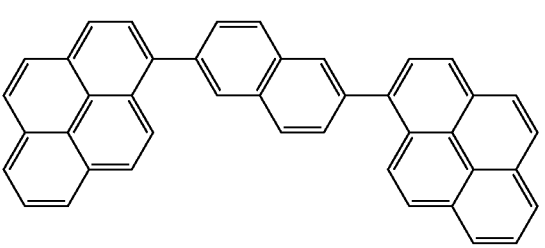

G-28

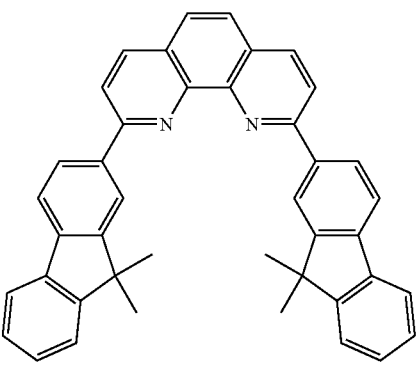

First, ITO was formed into a film, and then subjected to desired patterning processing to thereby form an ITO electrode (anode) on a glass substrate. In this case, the film thickness of the ITO electrode was set to 100 nm. The substrate on which the ITO electrode was formed thus obtained was used as an ITO substrate in the following process.

Next, vacuum evaporation by resistance heating in a vacuum chamber of $1\times10^{-5}$ Pa was performed to successively form the organic compound layers and the electrode layers shown in the following table on the ITO substrate. In this case, the electrode area of the electrodes (the metal electrode layers and the cathode) facing each other was set to 3 mm².

TABLE 7

|  | Material | Film thickness (nm) |
|---|---|---|
| Hole transporting layer | G-21 | 30 |
| Electron blocking layer | G-22 | 10 |
| First light emitting layer | G-23 (First host) | 20 |
|  | G-24 (First guest) |  |

TABLE 7-continued

| | Material | Film thickness (nm) |
|---|---|---|
| Second light emitting layer | Exemplary compound A18 (Second guest) (G-23:G-24:A18 = 90:4.5:0.5 (Weight ratio)) G-25 (Second host) G-26 (Third host) (G-25:G-26 = 96:4 (Weight ratio)) | 20 |
| Hole blocking layer | G-27 | 10 |
| Electron transporting layer | G-28 | 30 |
| First metal electrode layer | LiF | 1 |
| Second metal electrode layer | Al | 100 |

In this Example, G-23 and G-25 are H11, H22, and H11 shown in Table 2, respectively.

The obtained device was measured and evaluated for the characteristics of the device. Specifically, the current-voltage characteristics were measured with a microammeter 4140B manufactured by Hewlett-Packard Company and the light emission luminosity was measured with BM7 manufactured by TOPCON CORPORATION. The measurements results are shown in Table 8.

Examples 49 to 51

In Example 48, organic light emitting devices in which white light is emitted by mixing colors were produced in the same manner as in Example 48, except changing, as appropriate, G-23, G-25, and the guest in Example 48 to the compounds shown in Table 8. The obtained device was measured and evaluated for the characteristics of the devices in the same manner as in Example 48. The measurements results are shown in Table 8. G-23 and G25 used in Table 8 are the hosts shown in Table 2.

TABLE 8

| | Guest | G-23 | G-25 | Light emission efficiency (cd/A) | Voltage (V) | Chromaticity (X, Y) |
|---|---|---|---|---|---|---|
| Example 48 | A18 | H18 | H4 | 12.5 | 5.8 | (0.33, 0.33) |
| Example 49 | A30 | H19 | H7 | 11.6 | 5.5 | (0.31, 0.35) |
| Example 50 | A46 | H22 | H8 | 13.0 | 5.7 | (0.33, 0.34) |
| Example 51 | A66 | H24 | H4 | 10.0 | 5.3 | (0.30, 0.32) |

Thus, as described above with reference to examples, when the organic compound according to aspects of the invention is applied to a light emitting device, the organic compound according to aspects of the invention is suitable as a red light emitting material because a chromaticity suitable for pure red light emission is demonstrated by increasing the wavelength by about 10 nm to the wavelength of the solution. As the light emission efficiency, a high value, 9.5 cd/A at the maximum, is indicated when only the compound according to aspects of the invention was used for the light emitting material.

Example 52

Synthesis of Exemplary Compound A72

An exemplary compound A72 was obtained in the same manner as in Example 1, except using the compound E61 shown below in place of 1-naphthalene boronic acid in Example 1(1) and the compound E62 shown below in place of the compound E6 in Example 1(4).

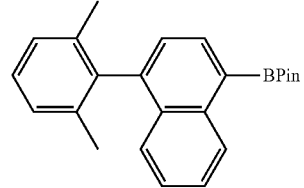

E61

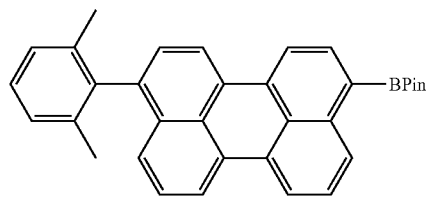

E62

The purity of the obtained compound was confirmed to be 98% or more as evaluated by HPLC.

The emission spectrum in the toluene solution (Concentration: $1 \times 10^{-5}$ mol/L) of the exemplary compound A72 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).

[MALDI-TOF-MS]

Actual measurement value: m/z=984.56, Calculated value: $C_{78}H_{48}$=984.38

Example 53

Synthesis of Exemplary Compound A76

An exemplary compound A76 was obtained in the same manner as in Example 1, except using the compound E63 shown below in place of 1-naphthalene boronic acid in Example 1(1) and the compound E64 shown below in place of the compound E6 in Example 1(4).

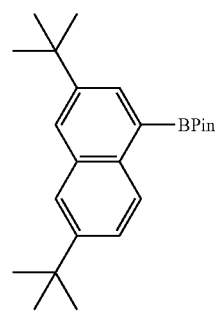

E63

-continued

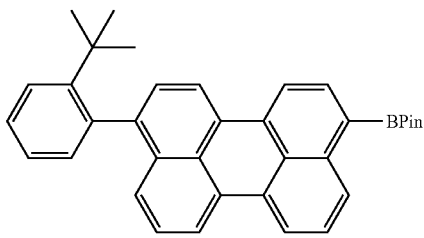

E64

The purity of the obtained compound was confirmed to be 98% or more as evaluated by HPLC.

The emission spectrum in the toluene solution (Concentration: $1\times10^{-5}$ mol/L) of the exemplary compound A76 was measured in the same manner as in Example 1. As a result, a spectrum having the maximum intensity at 591 nm was obtained.

Further, the mass spectrometry was performed using MALDI-TOF-MS (Autoflex LRF manufactured by Bruker).
[MALDI-TOF-MS]
Actual measurement value: m/z=1020.88, Calculated value: $C_{80}H_{60}$=1020.47

Example 54

Synthesis of Exemplary Compound A77

An exemplary compound A77 was obtained in the same manner as in Example 1, except using the compound E65 shown below in place of 1-naphthalene boronic acid in Example 1(1) and the compound E66 shown below in place of the compound E6 in Example 1(4).

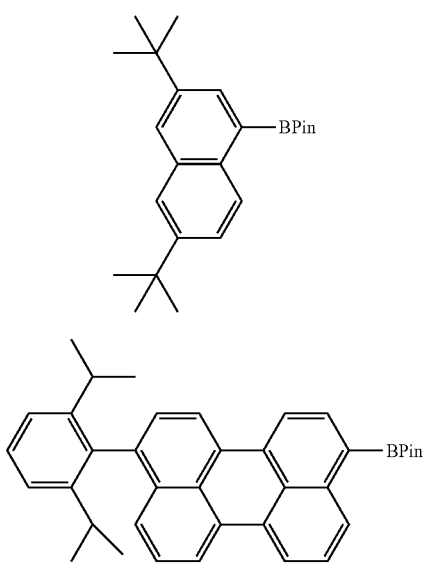

The purity of the obtained compound was confirmed to be 98% or more as evaluated by HPLC.

The emission spectrum in the toluene solution (Concentration: $1\times10^{-5}$ mol/L) of the exemplary compound A77 was measured in the same manner as in Example 1. As a result, a spectrum having the maximum intensity at 591 nm was obtained.

Further, the mass spectrometry was performed using MALDI-TOF-MS (Autoflex LRF manufactured by Bruker).
[MALDI-TOF-MS]
Actual measurement value: m/z=1048.68, Calculated value: $C_{82}H_{64}$=1048.50

Example 55

Synthesis of Exemplary Compound A79

An exemplary compound A79 was obtained in the same manner as in Example 1, except using the compound E68 shown below in place of 1-naphthalene boronic acid in Example 1(1) and the compound E69 shown below in place of the compound E6 in Example 1(4).

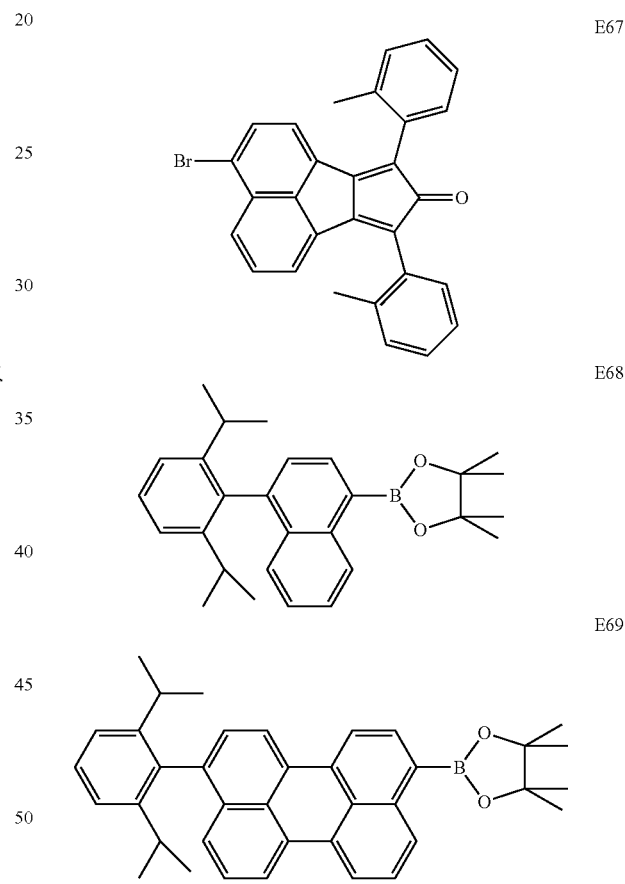

The purity of the obtained compound was confirmed to be 98% or more as evaluated by HPLC.

The emission spectrum in the toluene solution (Concentration: $1\times10^{-5}$ mol/L) of the exemplary compound A79 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1125.1, Calculated value: $C_{88}H_{68}$=1124.53

Example 56

Synthesis of Exemplary Compound A80

An exemplary compound A80 was obtained in the same manner as in Example 1, except using the compound E71 shown below in place of 1-naphthalene boronic acid in Example 1(1) and the compound E72 shown below in place of the compound E6 in Example 1(4).

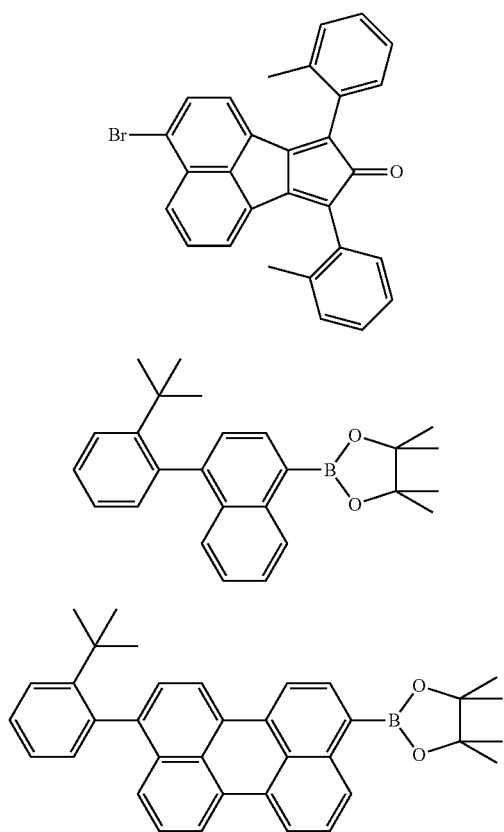

The purity of the obtained compound was confirmed to be 98% or more as evaluated by HPLC.

The emission spectrum in the toluene solution (Concentration: $1 \times 10^{-5}$ mol/L) of the exemplary compound A80 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1068.60, Calculated value: $C_{84}H_{60}$=1068.47

Example 57

Synthesis of Exemplary Compound A81

An exemplary compound A81 was obtained in the same manner as in Example 1, except using the compound E73 shown below in place of the compound E1 and the compound E74 shown below in place of 1-naphthalene boronic acid in Example 1(1) and the compound E75 shown below in place of the compound E6 in Example 1(4).

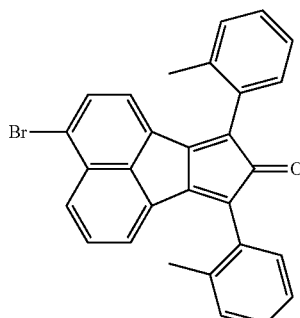

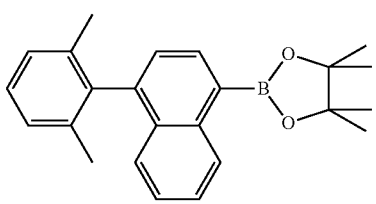

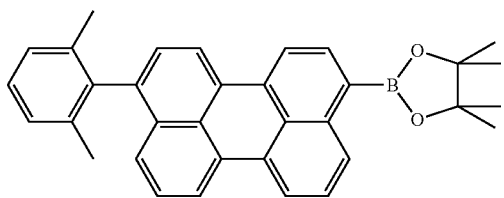

The purity of the obtained compound was confirmed to be 99% or more as evaluated by HPLC.

The emission spectrum in the toluene solution (Concentration: $1 \times 10^{-5}$ mol/L) of the exemplary compound A81 was measured in the same manner as in Example 1. As a result, a spectrum having the maximum intensity at 593 nm was obtained.

Further, the mass spectrometry was performed using MALDI-TOF-MS (Autoflex LRF manufactured by Bruker).
[MALDI-TOF-MS]
Actual measurement value: m/z=1012.45, Calculated value: $C_{80}H_{52}$=1012.41

Example 58

Synthesis of Exemplary Compound A82

An exemplary compound A82 was obtained in the same manner as in Example 1, except using the compound E76 shown below in place of the compound E1 and the compound E77 shown below in place of 1-naphthalene boronic acid in Example 1(1) and the compound E78 shown below in place of the compound E6 in Example 1(4).

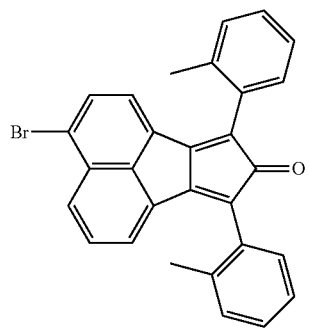
E76

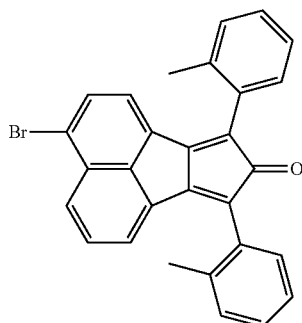
E79

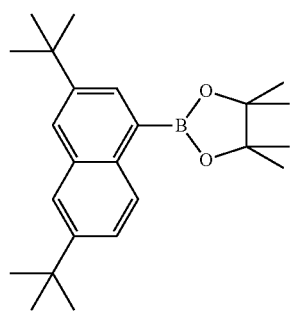
E77

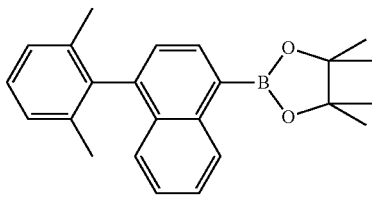
E80

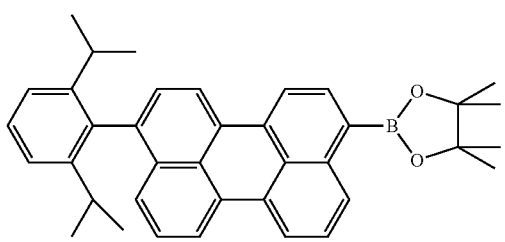
E78

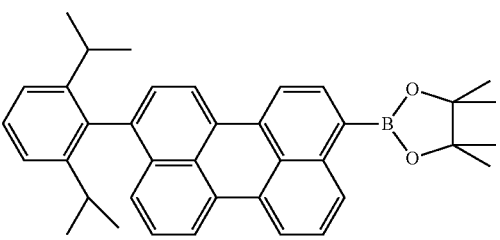
E81

The purity of the obtained compound was confirmed to be 99% or more as evaluated by HPLC.

The emission spectrum in the toluene solution (Concentration: $1\times10^{-5}$ mol/L) of the exemplary compound A82 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1076.88, Calculated value: $C_{84}H_{68}$=1076.53

Example 59

Synthesis of Exemplary Compound A84

An exemplary compound A84 was obtained in the same manner as in Example 1, except using the compound E79 shown below in place of the compound E1 and the compound E80 shown below in place of 1-naphthalene boronic acid in Example 1(1) and the compound E81 shown below in place of the compound E6 in Example 1(4).

The purity of the obtained compound was confirmed to be 98% or more as evaluated by HPLC.

The emission spectrum in the toluene solution (Concentration: $1\times10^{-5}$ mol/L) of the exemplary compound A84 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1068.67, Calculated value: $C_{84}H_{60}$=1068.47

Example 60

Synthesis of Exemplary Compound A89

An exemplary compound A89 was obtained in the same manner as in Example 1, except using the compound E82 shown below in place of the compound E1 and the compound E83 shown below in place of 1-naphthalene boronic acid in Example 1(1) and the compound E84 shown below in place of the compound E6 in Example 1(4).

E82

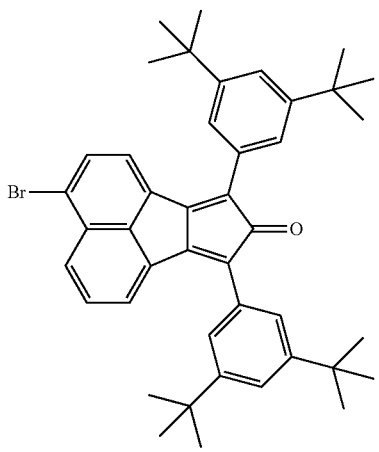

E83

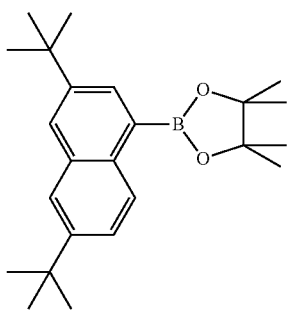

E84

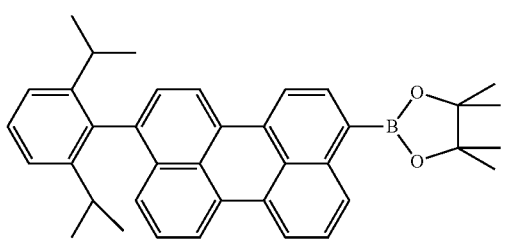

The purity of the obtained compound was confirmed to be 98% or more as evaluated by HPLC.

The emission spectrum in the toluene solution (Concentration: $1\times10^{-5}$ mol/L) of the exemplary compound A89 was measured in the same manner as in Example 1. As a result, a spectrum having the maximum intensity at 592 nm was obtained.

Further, the mass spectrometry was performed using MALDI-TOF-MS (Autoflex LRF manufactured by Bruker).
[MALDI-TOF-MS]
Actual measurement value: m/z=1272.59, Calculated value: $C_{98}H_{96}$=1272.75

Examples 61 to 69

Organic light emitting devices were produced in the same manner as in Example 29, except changing, as appropriate, G-3, G-4, and the guest in Example 29 to the compounds shown in Table 9. The obtained devices were measured and evaluated for the characteristics of the devices in the same manner as in Example 29. The measurement results are shown in Table 9. In Table 9, when the materials of G-3 and G-4 are the same, the materials of the host and the assist are the same and the hosts shown in Table 3 were used.

TABLE 9

| | Guest | G-3 | G-4 | Light emission efficiency (cd/A) | Voltage (V) | Chromaticity (X, Y) |
|---|---|---|---|---|---|---|
| Example 61 | A72 | H10 | H21 | 4.6 | 4.3 | (0.65, 0.35) |
| Example 62 | A73 | H27 | H21 | 4.1 | 4.3 | (0.66, 0.34) |
| Example 63 | A76 | H10 | H18 | 4.2 | 4.2 | (0.65, 0.35) |
| Example 64 | A79 | H26 | H26 | 3.8 | 4.0 | (0.65, 0.35) |
| Example 65 | A80 | H25 | H19 | 4.2 | 4.6 | (0.65, 0.35) |
| Example 66 | A81 | H18 | H18 | 4.5 | 4.2 | (0.66, 0.35) |
| Example 67 | A82 | H12 | H21 | 4.9 | 4.3 | (0.65, 0.35) |
| Example 68 | A84 | H10 | H20 | 4.2 | 4.4 | (0.65, 0.35) |
| Example 69 | A89 | H28 | H28 | 4.0 | 4.0 | (0.65, 0.35) |

As described above with reference to the embodiments and the examples, the organic compound according to aspects of the invention can emit light in the red region by the basic skeleton itself.

Furthermore, the organic compound according to aspects of the invention has red light emission with high color purity by the basic skeleton itself, and, therefore, can also provide an organic light emitting device with high light emission efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-171131 filed Aug. 4, 2011 and No. 2012-124503 filed May 31, 2012, which is hereby incorporated by reference herein in its entirety.

What is claimed is:

1. An organic compound represented by the following Formula (1),

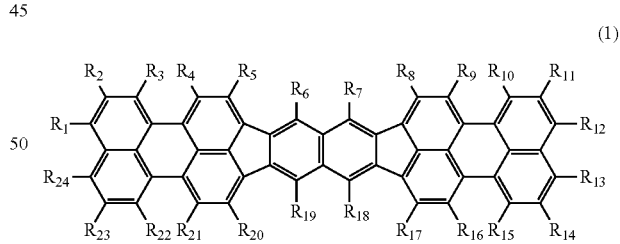

(1)

wherein, in Formula (1), $R_1$ to $R_{24}$ each are independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted arylocxy group, a silyl group, and a cyano group.

2. The organic compound according to claim 1, wherein $R_1$ to $R_{24}$ each are independently selected from a hydrogen atom, a halogen atom, a substituted or unsubstituted alkyl group, and a substituted or unsubstituted aryl group.

3. An organic light emitting device, comprising:
an anode and a cathode; and
organic compound layers disposed between the anode and the cathode, wherein
the organic compound according to claim 1 is contained at least one of the organic compound layers.

4. The organic light emitting device according to claim 3, wherein at least one of the organic compound layers is a light emitting layer.

5. The organic light emitting device according to claim 4, which emits red light.

6. The organic light emitting device according to claim 5, further comprising another light emitting layer disposed in such a manner as to be laminated on the light emitting layer, wherein the other light emitting layer emits a different color of light from the color of the light emitted from the light emitting layer.

7. The organic light emitting device according to claim 6, which emits white light.

8. A display device, comprising:
a plurality of pixels, wherein
the plurality of pixels have the organic light emitting device according to claim 3 and a TFT element which is electrically connected to the organic light emitting device.

9. A display device, comprising:
a plurality of pixels, wherein
the plurality of pixels have the organic light emitting device according to claim 6, a TFT element which is electrically connected to the organic light emitting device, and a color filter.

10. An image display device, comprising:
an input portion for inputting image information; and
a display portion for outputting an image, wherein
the display portion has the display device according to claim 8.

11. A lighting device, comprising:
the organic light emitting device according to claim 3; and
an inverter circuit which is connected to the organic light emitting device.

12. The lighting device according to claim 11, comprising a color filter.

13. An image forming device, comprising:
a plurality of the organic light emitting devices according to claim 3, wherein
a photoconductor drum is provided which obtains an electrostatic latent image by light emitted from the organic light emitting devices.

* * * * *